(12) United States Patent
Lee et al.

(10) Patent No.: US 11,066,412 B2
(45) Date of Patent: Jul. 20, 2021

(54) SUBSTITUTED PYRROLO[2,1-A]PHTHALAZINES AND BENZO[G]PYRROLO[2,1-A]PHTHALAZINES FOR THE TREATMENT OF CANCER

(71) Applicant: Academia Sinica, Taipei (TW)

(72) Inventors: Te-Chang Lee, Taipei (TW);
Tsann-Long Su, Amawalk, NY (US);
Tai-Lin Chen, New Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 16/764,873

(22) PCT Filed: Nov. 16, 2018

(86) PCT No.: PCT/US2018/061400
§ 371 (c)(1),
(2) Date: May 17, 2020

(87) PCT Pub. No.: WO2019/099755
PCT Pub. Date: May 23, 2019

(65) Prior Publication Data
US 2020/0339584 A1    Oct. 29, 2020

Related U.S. Application Data

(60) Provisional application No. 62/587,484, filed on Nov. 17, 2017.

(51) Int. Cl.
C07D 487/14    (2006.01)
C07D 487/22    (2006.01)
(Continued)

(52) U.S. Cl.
CPC ............ C07D 487/04 (2013.01); A61P 35/02 (2018.01); A61K 45/06 (2013.01)

(58) Field of Classification Search
CPC .......................... C07D 487/14; C07D 487/22
(Continued)

(56) References Cited

FOREIGN PATENT DOCUMENTS

WO    WO-2019099755 A1 *  5/2019    ........... A61P 35/02

OTHER PUBLICATIONS

Jordan, V. C. Nature Reviews: Drug Discovery, 2, 2003, 205.*
(Continued)

*Primary Examiner* — Douglas M Willis
(74) *Attorney, Agent, or Firm* — NZ Carr Law Office PLLC

(57) ABSTRACT

Disclosed herein are novel bifunctional compounds and their uses for the treatment and/or prophylaxis of cancers. The bifunctional compound disclosed herein has the structure of formula (I),

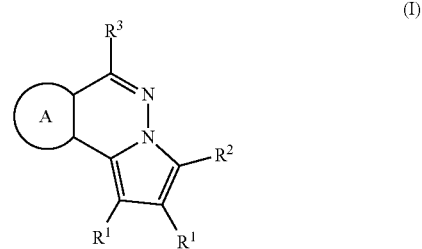

wherein,

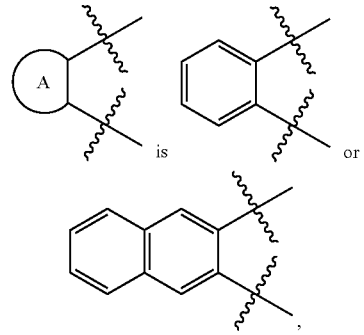

optionally substituted with one or more substituents independently selected from the group consisting of halo, alkyl, haloalkyl, alkenyl, C(O)H, OH, O(alkyl), O(CO)alkyl, O(aryl), aryl, and —O(CH$_2$)$_x$N(R$_b$)$_2$;

$R^1$ is an alkyl optionally substituted with one or more substituents independently selected from the group consisting of halo, —OR, —O(CO)CH$_3$, —OSO$_2$R, and —OCONHR;

R is hydrogen, alkyl, cycloalkyl, or aryl;

$R^2$ is hydrogen, alkyl, cycloalkyl, aryl or heteroaryl, in which the aryl or heteroaryl is optionally substituted with one or more substituents independently selected from the group consisting of C$_{1-6}$ alkyl, O(alkyl), halo, cyano, nitro, —N(R$_c$)$_2$, OCH$_2$O—, O(CH$_2$)$_2$O—, pyrrolidinyl, piperidinyl, piperazinyl, morpholino, and 4—(piperido) piperidinyl;

$R^3$ is -NR$^A$R$^B$, or -NHPhR$^C$, or -NR$^A$R$^B$ are taken together to form pyrrolidin-1-yl, piperidin-1-yl, piperazin-1-yl, morpholin-4-yl, 4-(piperidin-1-y)piperidin-1-yl, or 4-(piperidin-4-yl)piperidin-1-yl, wherein the piperazin-1-yl or 4-(piperidin-4-yl) piperidin-1-yl is optionally substituted with one or more substituents independently selected from the group consisting of alky, and —(CH$_2$)$_n$CONH(CH$_2$)$_m$NR$^A$R$^B$;

$R^A$ and $R^B$ are independently H or C$_1$-C$_6$ alkyl;

$R^C$ is hydrogen, halo, alkyl, alkenyl, alknyl, O(alkyl), —NHCOR$_a$, —NHC(O)OR$_a$, heterocyclyl or aryl, in which the alkyl is optionally substituted with one or more substituents independently selected from the group consisting of halo, alkyl, haloalkyl, alkenyl C(O)H, OC(O) alkyl, O(aryl), and aryl, in which the aryl is optionally substituted with one or more substituents independently selected from the group consisting of halo, CN, C$_{1-6}$ alkyl, (Continued)

$N(R_c)_2$, $NO_2$, $O(alkyl)$, —$OCH_2O$—, —$O(CH_2)_2O$—, pyrrolidinyl, pepiridinyl, piperazinyl, morpholino, and 4-(piperido)piperidinyl;

$R_a$ is $C_{1-6}$ alkyl or aryl;

$R_b$ is $C_{1-10}$ alkyl, pyrrolidin-1-yl, piperidin-1-yl, piperazin-1-yl, morpholin-4-yl, 4-(piperidin-1-yl)piperidin-1-yl, or 4-(piperidin-4-yl)piperidin-1-yl;

$R_c$, is hydrogen or $C_{1-10}$ alkyl; and.

x, n and m are independently an integral between 1 to 5.

25 Claims, 18 Drawing Sheets

(51) Int. Cl.
C07D 487/04 (2006.01)
A61P 35/02 (2006.01)
A61K 45/06 (2006.01)

(58) Field of Classification Search
USPC .................................. 544/233, 234
See application file for complete search history.

(56) References Cited

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*

Vippagunta, et al. Advanced Drug Delivery Reviews, 48, 2001, 18.*

* cited by examiner (A)

(B)

(C)

(A)

(B)

(A)

(B)

SUBSTITUTED PYRROLO[2,1-A]PHTHALAZINES AND BENZO[G]PYRROLO[2,1-A]PHTHALAZINES FOR THE TREATMENT OF CANCER

CROSS REFERENCES TO RELATED APPLICATION

This application claims priority under 35 U.S.C. § 119(e) to U.S. Provisional Application, U.S. Ser. No. 62/587,484, filed Nov. 17, 2017, which is incorporated by reference herein in its entirety.

BACKGROUND OF THE INVENTION

1. Field of the Invention

The present disclosure in general relates to the field of treatment of cancers; more particularly to novel bi-functional compounds that exhibit both anti-angiogenesis and DNA cross-linking activities, and their uses in the treatment and/or prophylaxis of cancers.

2. Description of Related Art

Cancer has been the leading causes of death worldwide. Treatment of cancer commonly involves surgical removal and/or administering a chemotherapeutic agent or radiation therapy. Numerous compounds have been developed as anti-cancer agents, and, most drug developers design anti-cancer agents by targeting to one specific cellular mechanism that leads to uncontrolled cell proliferation. Instead of focusing on suppressing or inhibiting enzymes in one particular metabolic pathway, inventors of the present disclosure have created a compound with dual modes of actions by conjugating two active moieties into one molecular, specifically, one moiety bears anti-angiogenesis activity while the other moiety bears DNA crosslinking activity. Accordingly, one would expect the hybrid molecular to be a much potent anti-cancer agent as it possesses two functional groups that attack cancer cells from two distinct pathways.

SUMMARY

Inventors of the present disclosure designed and synthesized new classes of compounds formed by conjugating a VEGF and aurora kinase inhibitory moiety and a DNA crosslinking moiety. The newly produced hybrid compounds exhibit significant anti-proliferative activity in various human cancer cells, thus, they are potential candidates for the development of medicaments suitable for the treatment and/or prophylaxis of cancers.

Accordingly, one aspect of the present disclosure is to provide a novel compound having the structure of formula (I), a pharmaceutically acceptable solvate or a stereoisomer thereof,

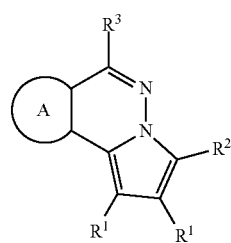

(I)

wherein,

A is an optionally substituted 6-10 membered unsaturated carbon cycle;

$R^1$ is an alkyl optionally substituted with halo, —OR, —OAc, —OSO$_2$R, or —OCONHR, wherein R is hydrogen, alkyl, cycloalkyl, or aryl;

$R^2$ is hydrogen, alkyl, cycloalkyl, aryl or heteroaryl;

$R^3$ is —NR$^A$R$^B$, —NHPhR$^C$, mono- or bis-saccharide(s) group, or an amino acid group, or —NR$^A$R$^B$ are taken together to form an optionally substituted aniline or cycloalkylamine selected from the group consisting of morpholine, pyrrolidine, piperidine, 1-substituted piperazine, 1,4'-bipiperidine, 4'-substituted 4,4'-bipiperidine; wherein the substituent on piperazine and 4,4'-bipiperidine is alky, —(CH$_2$)$_n$CONH(CH$_2$)$_m$NR$^A$R$^B$, in which n and m are independently an integral between 1 to 5, $R^A$ and $R^B$ are independently H or C$_1$-C$_6$ alkyl; and $R^C$ is hydrogen, halo, alkoxy, —CH$_2$OH, —NHCOR$_a$, —NHC(O)OR$_a$, or optionally substituted alkyl, alkenyl, alkynyl, herocyclyl, or aryl, and R$_a$ is C$_{1-6}$ alkyl or aryl; and the aryl or heteroaryl is optionally substituted with at least one substituent selected from the group consisting of C$_{1-6}$ alkyl, alkoxy, halo, cyano, nitro, —NH$_2$, —NHR$_c$, —N(R$_c$)$_2$, cyclolkylamino, methylenedioxy or ethylenedioxy group, in which It, is independently hydrogen or C$_{1-10}$ alkyl.

According to some embodiments of the present disclosure, in the formula (I), R$^3$ is 1H-pyrazol-3-amino, 1H-imidazol-2-amino, or pyrimidine-amino.

According to some embodiments of the present disclosure, in the formula (I), the cycloalkylamino group is selected from the group consisting of, pyrrolidinyl, piperidinyl, morpholino, piperazinyl, and 4-piperidopiperidinyl.

According to some embodiments of the present disclosure, particular compounds are of formula (1-A),

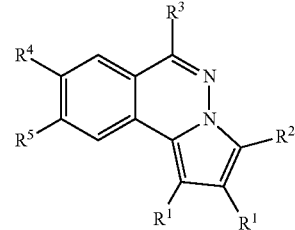

(I-A)

wherein, $R^1$ is an alkyl optionally substituted with halo, —OR, —OAc, -OSO$_2$R, or —OCONHR, wherein R is hydrogen, alkyl, cycloalkyl, or aryl;

$R^2$ is hydrogen, alkyl, cycloalkyl, aryl or heteroaryl;

$R^3$ is —NR$^A$R$^B$, —NHPhR$^C$, mono- or bis-saccharide(s) group, or an amino acid group, or —NR$^A$R$^B$ are taken together to form an optionally substituted aniline or cycloalkylamine selected from the group consisting of morpholine, pyrrolidine, piperidine, 1-substituted piperazine, 1,4'-bipiperidine, 4'-substituted 4,4'-bipiperidine; wherein the substituent on piperazine and 4,4'-bipiperidine is alky, —(CH$_2$)$_n$CONH(CH$_2$)$_m$NR$^A$R$^B$, in which n and m are independently an integral between 1 to 5, $R^A$ and $R^B$ are independently H or C$_{1-6}$ alkyl; and $R^C$ is hydrogen, halo, alkoxy, —CH$_2$OH, —NHCOR$_a$, —NHC(O)OR$_a$, or optionally substituted alkyl, alkenyl, alkynyl, herocyclyl, or aryl, and R$_a$ is C$_{1-6}$ alkyl or aryl;

R[4] and R[5] are independently hydrogen, —OH, alkoxy, or —O(CH$_2$)$_x$N(R$_b$)$_2$, in which x is an integral between 1 to 5; and R$_b$ is C$_{1-10}$ alkyl, or a cycloalkylamino group; and the aryl or heteroaryl is optionally substituted with at least one substituent selected from the group consisting of C$_{1-6}$ alkyl, alkoxy, halo, cyano, nitro, —NH$_2$, —NHR$_c$, —N(R$_c$)$_2$, cyclolkylamino, methylenedioxy or ethylenedioxy group, in which R$_c$ is independently hydrogen or C$_{1-10}$ alkyl.

According to one preferred embodiment, in the formula (I-A), R[1] is methyl substituted with —OH, R[2] is ethyl, R[3] is morpholine, and R[4] and R[5] are independently hydrogen.

According to one preferred embodiment, in the formula (I-A), R[1] is methyl substituted with —OH, R[2] is methyl, R[3] is pyrrolidine, and R[4] and R[5] are independently hydrogen.

According to another preferred embodiment, in the formula (I-A), R[1] is methyl substituted with OH, R[2] is methyl, R[3] is 1,4'-bipiperidine, and R[4] and R[5] are independently hydrogen.

According to a further embodiment, in the formula (I-A), R[1] is methyl substituted with —OCONH(C$_2$H$_5$), R[2] is methyl, R[3] is pyrrolidin, and R[4] and R[5] are independently hydrogen.

According to some embodiments of the present disclosure, particular compounds are of formula (I-B),

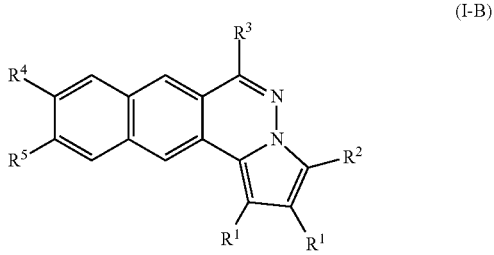

(I-B)

wherein,

R[1] is an alkyl optionally substituted with halo, —OR, —OAc, —OSO$_2$R, or —OCONHR, wherein R is hydrogen, alkyl, cycloalkyl, or aryl;

R[2] is hydrogen, alkyl, cycloalkyl, aryl or heteroaryl;

R[3] is —NR$^A$R$^B$, —NHPhR$^C$, mono- or bis-saccharide(s) group, or an amino acid group, or —NR$^A$R$^B$ are taken together to form an optionally substituted aniline or cycloalkylamine selected from the group consisting of morpholine, pyrrolidine, piperidine, 1-substituted piperazine, 1,4'-bipiperidine, 4'-substituted 4,4'-bipiperidine; wherein the substituent on piperazine and 4,4'-bipiperidine is alky, —(CH$_2$)$_n$CONH(CH$_2$)$_m$NR$^A$R$^B$, in which n and m are independently an integral between 1 to 5, R$^A$ and R$^B$ are independently H or C$_{1-6}$ alkyl; and R$^C$ is hydrogen, halo, alkoxy, CH$_2$OH, —NHCOR$_a$, NHC(O)OR$_a$, or optionally substituted alkyl, alkenyl, alkynyl, herocyclyl, or aryl, and R$_a$ is C$_{1-6}$ alkyl or aryl;

R[4] and R[5] are independently hydrogen, —OH, alkoxy, or —O(CH$_2$)$_x$N(R$_b$)$_2$, in which x is an integral between 1 to 5; and R$_b$ is C$_{1-10}$ alkyl, or a cycloalkylamino group; and the aryl or heteroaryl is optionally substituted with at least one substituent selected from the group consisting of C$_{1-6}$ alkyl, alkoxy, halo, cyano, nitro, —NH$_2$, —NHR$_c$, —N(R$_c$)$_2$, cyclolkylamino, methylenedioxy or ethylenedioxy group, in which R$_c$ is independently hydrogen or C$_{1-10}$ alkyl.

According to one preferred embodiment, in the formula (I-B), R[1] is methyl substituted with —OH, R[2] is methyl, R[3] is dimethylamine, and R[4] and R[5] are independently hydrogen.

According to another embodiment, in the formula (I-B), R[1] is methyl substituted with —OCONH(C$_2$H$_5$), R[2] is methyl, R[3] is dimethylamine, and R[4] and R[5] are independently hydrogen.

According to a further embodiment, in the formula (I-B), R[1] is methyl substituted with —OCONH(C$_2$H$_5$), R[2] is methyl, R[3] is pyrrolidine, and R[4] and R[5] are independently hydrogen.

The second aspect of the present disclosure is to provide a pharmaceutical composition for the treatment or prophylaxis of a subject having or suspected of having cancer. The pharmaceutical composition comprises a therapeutically or prophylactically effective amount of the compound of formula (I); and a pharmaceutically acceptable carrier.

The compound of formula (I) is present at a level of about 0.1% to 99% by weight, based on the total weight of the pharmaceutical composition. In some embodiments, the compound of formula (I) is present at a level of at least 1% by weight, based on the total weight of the pharmaceutical composition. In certain embodiments, the compound of formula (I) is present at a level of at least 5% by weight, based on the total weight of the pharmaceutical composition. In still other embodiments, the compound of formula (I) is present at a level of at least 10% by weight, based on the total weight of the pharmaceutical composition. In still yet other embodiments, the compound of formula (I) is present at a level of at least 25% by weight, based on the total weight of the pharmaceutical composition.

Preferably, the compound has the structure of formula (I-A)

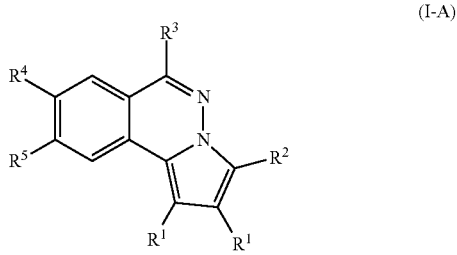

(I-A)

wherein,

R[1] is an alkyl optionally substituted with halo, —OR, —OAc, —OSO$_2$R, or —OCONHR, wherein R is hydrogen, alkyl, cycloalkyl, or aryl;

R[2] is hydrogen, alkyl, cycloalkyl, aryl or heteroaryl;

R[3] is —NR$^A$R$^B$, NHPhR$^C$, mono- or bis-saccharide(s) group, or an amino acid group, or —NR$^A$R$^B$ are taken together to form an optionally substituted aniline orcycloalkylamine selected from the group consisting of morpholine, pyrrolidine, piperidine, 1-substituted piperazine, 1,4'-bipiperidine, 4'-substituted 4,4'-bipiperidine; wherein the substituent on piperazine and 4,4'-bipiperidine is alky, —(CH$_2$)$_n$CONH(CH$_2$)$_m$NR$^A$R$^B$, in which n and m are independently an integral between 1 to 5, R$^A$ and R$^B$ are independently H or C$_{1-6}$ alkyl; and R$^C$ is hydrogen, halo, alkoxy, —CH$_2$OH, —NHCOR$_a$, —NHC(O)OR$_a$, or optionally substituted alkyl, alkenyl, alkynyl, herocyclyl, or aryl, and R$_a$ is C$_{1-6}$ alkyl or aryl;

$R^4$ and $R^5$ are independently hydrogen, —OH, alkoxy, or —O(CH$_2$)$_x$N(R$_b$)$_2$, in which
x is an integral between 1 to 5; and
R$_b$ is C$_{1-10}$ alkyl, or a cycloalkylamino group; and
the aryl or heteroaryl is optionally substituted with at least one substituent selected from the group consisting of C$_{1-6}$ alkyl, alkoxy, halo, cyano, nitro, —NH$_2$, —NHR$_c$, —N(R$_c$)$_2$, cyclolkylamino, methylenedioxy or ethylenedioxy group, in which R$_c$ is independently hydrogen or C$_{1-10}$ alkyl.

Optionally or in addition, the compound of formula (I-A) is formulated into a liposome.

According to one preferred embodiment, in the formula (I-A), $R^1$ is methyl substituted with —OH, $R^2$ is ethyl, $R^3$ is morpholine, and $R^4$ and $R^5$ are independently hydrogen.

According to another preferred embodiment, in the formula (I-A), $R^1$ is methyl substituted with —OH, $R^2$ is methyl, $R^3$ is pyrrolidine, and $R^4$ and $R^5$ are independently hydrogen.

According to a further embodiment, in the formula (I-A), $R^1$ is methyl substituted with —OH, $R^2$ is methyl, $R^3$ is 1,4'-bipiperidine, and $R^4$ and $R^5$ are independently hydrogen.

According to still a further embodiment, $R^1$ is methyl substituted with —OCONH(C$_2$H$_5$), $R^2$ is methyl, $R^3$ is pyrrolidin, and $R^4$ and $R^5$ are independently hydrogen.

According to other preferred embodiments of the present disclosure, the compound has the structure of formula (I-B)

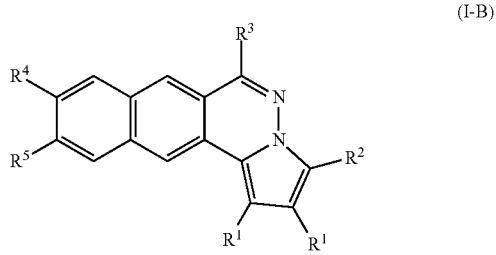

(I-B)

wherein,
$R^1$ is an alkyl optionally substituted with halo, —OR, —OAc, —OSO$_2$R, or —OCONHR, wherein R is hydrogen, alkyl, cycloalkyl, or aryl;
$R^2$ is hydrogen, alkyl, cycloalkyl, aryl or heteroaryl;
$R^3$ is —NR$^A$R$^B$, —NHPhR$^C$, mono- or bis-saccharide(s) group, or an amino acid group, or —NR$^A$R$^B$ are taken together to form an optionally substituted aniline or cycloalkylamine selected from the group consisting of morpholine, pyrrolidine, piperidine, 1-substituted piperazine, 1,4'-bipiperidine, 4'-substituted 4,4'-bipiperidine; wherein the substituent on piperazine and 4,4'-bipiperidine is alky, —(CH$_2$)$_n$CONH(CH$_2$)$_m$NR$^A$R$^B$, in which
n and m are independently an integral between 1 to 5,
R$^A$ and R$^B$ are independently H or C$_{1-6}$ alkyl; and
R$^C$ is hydrogen, halo, alkoxy, —CH$_2$OH, —NHCOR$_a$, —NHC(O)OR$_a$, or optionally substituted alkyl, alkenyl, alkynyl, herocyclyl, or aryl, and R$_a$ is C$_{1-6}$ alkyl or aryl;
$R^4$ and $R^5$ are independently hydrogen, —OH, alkoxy, or —O(CH$_2$)$_x$N(R$_b$)$_2$, in which
x is an integral between 1 to 5; and
R$_b$ is C$_{1-10}$ alkyl, or a cycloalkylamino group; and
the aryl or heteroaryl is optionally substituted with at least one substituent selected from the group consisting of C$_{1-6}$ alkyl, alkoxy, halo, cyano, nitro, —NH$_2$, —NHR$_c$, —N(R$_c$)$_2$, cyclolkylamino, methylenedioxy or ethylenedioxy group, in which R$_c$ is independently hydrogen or C$_{1-10}$ alkyl.

According to one preferred embodiment, in the formula (I-B), $R^1$ is methyl substituted with —OH, $R^2$ is methyl, $R^3$ is dimethylamine, and $R^4$ and $R^5$ are independently hydrogen.

According to another preferred embodiment, in the formula (I-B), $R^1$ is methyl substituted with —OCONH(C$_2$H$_5$), $R^2$ is methyl, $R^3$ is dimethylamine, and $R^4$ and $R^5$ are independently hydrogen.

According to a further preferred embodiment, in the formula (I-B), $R^1$ is methyl substituted with —OCONH (C$_2$H$_5$), $R^2$ is methyl, $R^3$ is pyrrolidine, and $R^4$ and $R^5$ are independently hydrogen.

The present disclosure also encompasses a method for the treatment or prophylaxis of a subject having or suspected of having a cancer. The method comprises the step of administering to the subject the present pharmaceutical composition.

Optionally or in addition, the method further comprises administering to the subject a chemotherapeutic agent before, together with, or after the administration of present pharmaceutical composition.

Exemplary chemotherapeutic agent that may be used in the present method includes, but is not limited to, DET, PLX4032, docetaxel, paclitaxel, cisplatin, oxaliplatin, betulinic acid, 4-S-cysteaminyl catechol, 4-S-cysteaminyl phenol, everolimus, bortezomib, carboplatin, dacarbazine, celecoxib, temozolomide, sorafenib, thalidomide, lenalidomide, valproic acid, vinblastine, imatinib mesylate, bosentan, apomine, arsenic trioxide, carmustine, lambrolizuma, anti-CTLA-4 drug, anti-programmed death receptor-1 (PD-1) drug, ipilimumab, tremelimumab, doxorubicin, MEK inhibitor, capecitabine, poly (ADP-ribose) polymerase (PARP) inhibitor, phosphoinositide 3-kinase (PI3K) inhibitor, mammalian target of rapamycin (mTOR) inhibitor, and tamoxifen.

Exemplary cancer that may be treated by the present method includes, but is not limited to, Hodgkin's disease, Non-Hodgkin's lymphomas, Acute Myelogenous Leukemia, Acute lymphoblastic leukemia, Chronic Myelogenous Leukemia, Ewing's sarcoma, multiple myeloma, Wilms' tumor, bone tumors, neuroblastoma, retinoblastoma, testicular cancer, thyroid cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small-cell lung cancer, brain cancer, melanoma, a non-melanoma skin cancer, and a CNS neoplasm.

The present disclosure also encompasses kits useful for the treatment or prophylaxis of a subject having a cancer. The kit include, at least, a first container containing the compound of formula (I); and a second container containing a chemotherapeutic agent.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where, FIG. 1 are photographs illustrating the effects of the compounds of formula (I) on the formation of DNA interstrand crosslinks in accordance with one embodiment of the present disclosure.

DETAILED DESCRIPTION OF THE INVENTION

Figure 1:
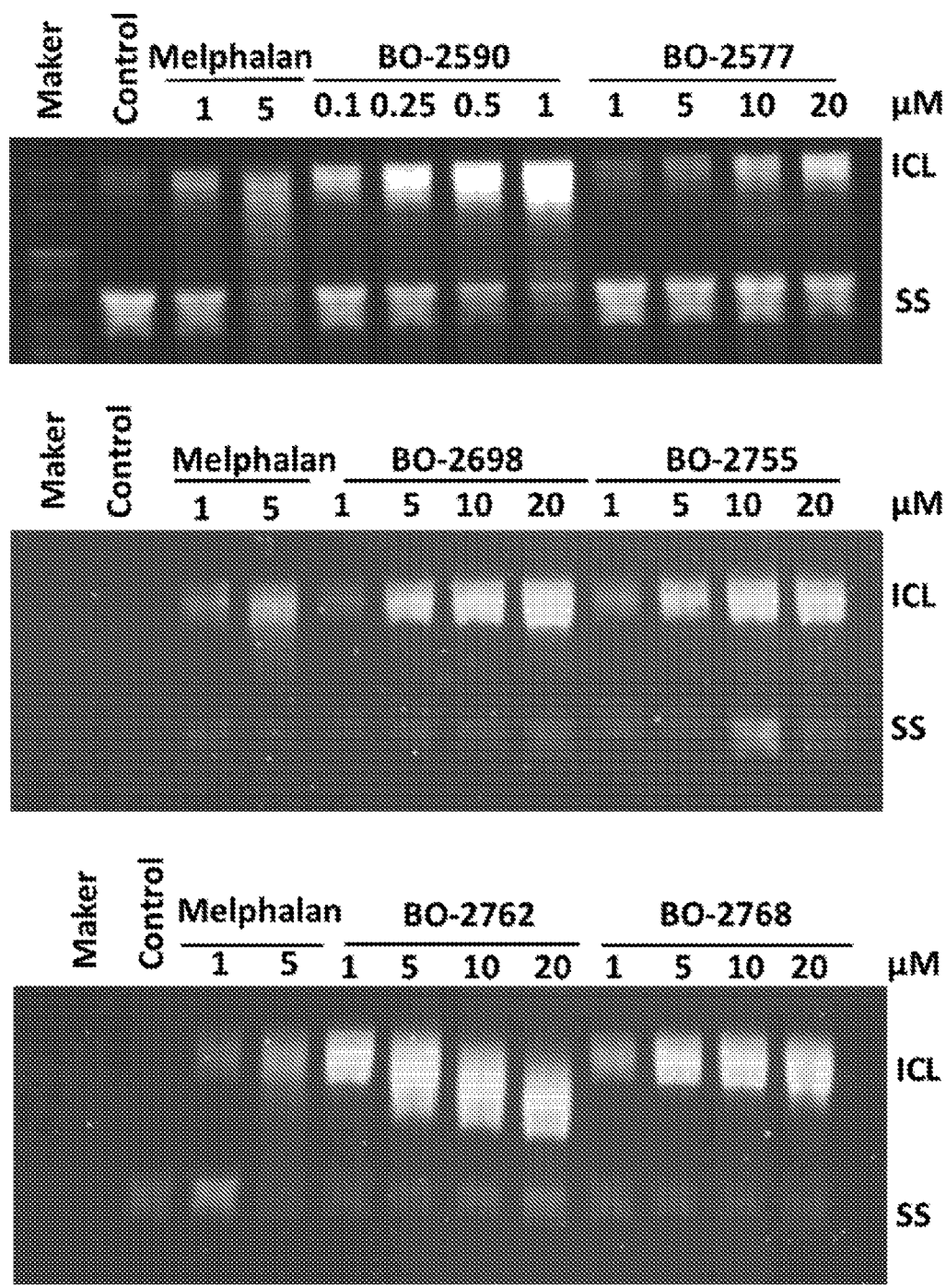

The detailed description provided below in connection with the appended drawings is intended as a description of the present disclosure and is not intended to represent the only forms in which the present disclosure may be constructed or utilized.

1. Definitions

When a range of values is listed, it is intended to encompass each value and sub-range within the range. For example "$C_{1-10}$" is intended to encompass, $C_1$, $C_2$, $C_3$, $C_4$, $C_5$, $C_6$, $C_7$, $C_8$, $C_9$, $C_{10}$, $C_{1-10}$, $C_{1-9}$, $C_{1-8}$, $C_{1-7}$, $C_{1-6}$, $C_{1-5}$, $C_{1-4}$, $C_{1-3}$, $C_{1-2}$, $C_{2-10}$, $C_{2-9}$, $C_{2-8}$, $C_{2-7}$, $C_{2-6}$, $C_{2-7}$, $C_{2-5}$, $C_{2-4}$, $C_{2-3}$, $C_{3-10}$, $C_{3-9}$, $C_{3-8}$, $C_{3-7}$, $C_{3-6}$, $C_{3-5}$, $C_{3-4}$, $C_{4-10}$, $C_{4-9}$, $C_{4-8}$, $C_{4-7}$, $C_{4-6}$, $C_{4-5}$, $C_{5-10}$, $C_{5-9}$, $C_{5-8}$, $C_{5-7}$, $C_{5-6}$, $C_{6-10}$, $C_{6-9}$, $C_{6-8}$, $C_{6-7}$, $C_{6-8}$, $C_{6-7}$, $C_{7-10}$, $C_{8-10}$, $C_{8-9}$, and $C_{9-10}$.

Unless otherwise indicated, the term "alkyl" means a straight chain, branched and/or cyclic ("cycloalkyl") hydrocarbon having from 1 to 20 (e.g., 1 to 10, 1 to 9, 1 to 8, 1 to 7, 1 to 6, 1 to 5, 1 to 4, 1 to 3, 1 to 2, or 1) carbon atoms. Alkyl moieties having from 1 to 4 carbons ($C_{1-4}$ alkyl) are referred to as "lower alkyl." Examples of alkyl groups include methyl, ethyl, propyl, isopropyl, n-butyl, t-butyl, isobutyl, 2-isopropyl-3-methyl butyl, pentyl, pentan-2-yl, hexyl, isohexyl, heptyl, heptan-2-yl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, and cyclohexyl. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is substituted $C_{2-10}$ alkyl. In some embodiments, cycloalkyl is a monocyclic, saturated carbocyclyl group having from 3 to 6 ring carbon atoms ("$C_{3-6}$ cycloalkyl"). In some embodiments, a cycloalkyl group has 5 to 6 ring carbon atoms ("$C_{5-6}$ cycloalkyl"). Examples of $C_{5-6}$ cycloalkyl groups include cyclopentyl ($C_5$) and cyclohexyl ($C_6$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocycloalkyl" refers to a radical of a 3- to 10-membered non-aromatic ring system having ring carbon atoms and 1 to 4 ring heteroatoms, wherein each heteroatom is independently selected from nitrogen, oxygen, sulfur, phosphorus, and silicon ("3-10 membered heterocycloalkyl"). In heterocyclyl groups that contain one or more nitrogen atoms, the point of attachment can be a carbon or nitrogen atom, as valency permits. Unless otherwise specified, each instance of heterocycloalkyl is independently optionally substituted, i.e., unsubstituted (an "unsubstituted heterocycloalkyl") or substituted (a "substituted heterocycloalkyl") with one or more substituents. In some embodiments, a heterocyclyl group is a 5-8 membered nonaromatic ring system having ring carbon atoms and 1-4 ring heteroatoms, wherein each heteroatom is independently selected from nitrogen, oxygen, and sulfur. In some embodiments, a heterocycloalkyl group is a 5-6 membered nonaromatic ring system having ring carbon atoms and 1-4 ring heteroatoms, wherein each heteroatom is independently selected from nitrogen, oxygen, and sulfur. In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocycloalkyl has one ring heteroatom selected from nitrogen, oxygen, and sulfur. Exemplary 5membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5dione. Exemplary 5membered heterocyclyl groups containing two heteroatoms include, without limitation, dioxolanyl, oxasulfuranyl, disulfuranyl, and oxazolidin-2-one. Exemplary 5membered heterocyclyl groups containing three heteroatoms include, without limitation, triazolinyl, oxadiazolinyl, and thiadiazolinyl. Exemplary 6membered heterocyclyl groups containing one heteroatom include, without limitation, piperidinyl, tetrahydropyranyl, dihydropyridinyl, and thianyl. Exemplary 6membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl.

Unless otherwise indicated, the term "aryl" means an aromatic ring or a partially aromatic ring system composed of carbon and hydrogen atoms. An aryl moiety may comprise multiple rings bound or fused together. Examples of aryl moieties include phenyl, naphthyl, pyrenyl, anthryl, and phenanthryl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is a substituted phenyl (e.g., benzyl).

Unless otherwise indicated, the term "heteroaryl" means an aryl moiety wherein at least one of its carbon atoms has been replaced with a heteroatom (e.g., N, O or S). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl. Exemplary 5membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 10-membered heteroaryl groups containing two heteroatoms include, without limitation, quinazolinyl.

Unless otherwise indicated, the term "alkylaryl" or "alkyl-aryl" means an alkyl moiety bound to an aryl moiety.

Unless otherwise indicated, the terms "halogen" and "halo" encompass fluoro, chloro, bromo, and iodo.

The term "amino" refers to a moiety of the formula: —N($R_c$)$_2$, wherein each instance of $R_c$ is independently a sub stituent described herein, or two instances of $R_c$ are connected to form substituted or unsubstituted heterocyclyl. In certain embodiments, the amino is unsubstituted amino (i.e., —NH$_2$). In certain embodiments, the amino is a substituted amino group, wherein at least one instance of $R_c$ is not hydrogen.

The term "saccharide group" refers to a saccharide monoradical covalently attached to another compound or atom via any atom of the saccharide moiety, for example, via the aglycone carbon atom. Representative saccharides include, by way of illustration, hexoses such as D-glucose, D-mannose, D-xylose, D-galactose, vancosamine, 3-desmethylvancosamine, 3-epi-vancosamine, 4-epi-vancosamine, a.cosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; bis-saccharides such as sucrose, lactose, maltose, 2-O-(α-L-vancosaminyl)-β-D-glucopyranose, or 2-O-(3-destnethyl-α-L-vancosaminyl)-β-D-glucopyranose; derivatives such as acetals, amines, acylated, sulfated and phosphorylated sugars. For the purposes of this definition, these saccharides are referenced using conventional three letter nomenclature and the saccharides can be either in their open or preferably in their pyranose form.

The term "amino acid group" refers to an amino acid monoradical attached to another compound or atom via any atom of the amino acid moiety, for example, via the amino or carboxyl function group, or any functional group on the side chain, such as the side chain amino group of lysine.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, —OH, —CHO, alkoxy, alkanoyloxy (e.g., —OAc), alkenyl, alkyl (e.g., methyl, ethyl, propyl, t-butyl), aryl, aryloxy, halo, or haloalkyl (e.g., —CCl$_3$, —CF$_3$, —C(CF$_3$)$_3$). Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$. The term "lower alkoxy" refers to —O-(lower alkyl), such as OCH$_3$ and —OCH$_2$CH$_3$.

Unless otherwise indicated, one or more adjectives immediately preceding a series of nouns is to be construed as applying to each of the nouns. For example, the phrase "optionally substituted alky, cycloalkyl, heterocycloalkyl, aryl, or heteroaryl" has the same meaning as "optionally substituted alky, optionally substituted cycloalkyl, optionally substituted heterocycloalkyl, optionally substituted aryl, or optionally substituted heteroaryl."

The present disclosure is not intended to be limited in any manner by the above exemplary listing of substituents.

The term "solvate" refers to forms of the compound that are associated with a solvent, usually by a solvolysis reaction. This physical association may include hydrogen bonding. Conventional solvents include water, methanol, ethanol, acetic acid, dimethyl sulfoxide (DMSO), tetrahydrofuran (THF), diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences.

For purpose of this invention, heteroatoms such as nitrogen may have hydrogen substituents and/or any suitable substituents as described herein which satisfy the valencies of the heteroatoms and result in the formation of a stable moiety.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound is an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the terms "treat," "treating" and "treatment" contemplate an action that occurs while a patient is suffering from the specified disease or disorder, which reduces the severity of the disease or disorder, or one or more of its symptoms, or retards or slows the progression of the disease or disorder.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. Novel Compounds of Formula (I)

This invention encompasses compounds of formula (I), a pharmaceutically acceptable solvate or a stereoisomer thereof,

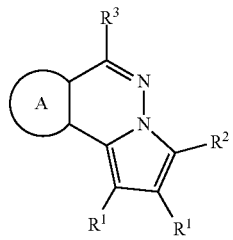

(I)

wherein,

A is an optionally substituted 6-10 membered unsaturated carbon cycle;

$R^1$ is an alkyl optionally substituted with halo, —OR, —OAc, —OSO$_2$R, or —OCONHR, wherein R is hydrogen, alkyl, cycloalkyl, or aryl;

$R^2$ is hydrogen, alkyl, cycloalkyl, aryl or heteroaryl;

$R^3$ is $NR^AR^B$, —NHPhR$^C$, mono- or bis-saccharide(s) group, or an amino acid group, or —NR$^A$R$^B$ are taken together to form an optionally substituted aniline or cycloalkylamine selected from the group consisting of morpholine, pyrrolidine, piperidine, 1-substituted piperazine, 1,4'-bipiperidine, 4'-substituted 4,4'-bipiperidine; wherein the substituent on piperazine and 4,4'-bipiperidine is alky, —(CH$_2$)$_n$CONH(CH$_2$)$_m$NR$^A$R$^B$, in which n and m are independently an integral between 1 to 5, $R^A$ and $R^B$ are independently H or C$_{1-6}$ alkyl; and $R^C$ is hydrogen, halo, alkoxy, —CH$_2$OH, —NHCOR$_a$, —NHC(O)OR$_a$, or optionally substituted alkyl, alkenyl, alkynyl, herocyclyl, or aryl, and R$_a$ is C$_{1-6}$ alkyl or aryl; and the aryl or heteroaryl is optionally substituted with at least one substituent selected from the group consisting of C$_{1-6}$ alkyl, alkoxy, halo, cyano, nitro, —NH$_2$, —NHR$_c$, —N(R$_c$)$_2$, cyclolkylamino, methylenedioxy or ethylenedioxy group, in which R$_c$ is independently hydrogen or C$_{1-10}$ alkyl.

According to some embodiments of the present disclosure, in the formula (I), $R^3$ is 1H-pyrazol-3-amino, 1H-imidazol-2-amino, or pyrimidine-amino.

According to further embodiments of the present disclosure, in the formula (I), the cycloalkylamino group is selected from the group consisting of, pyrrolidinyl, piperidinyl, morpholino, piperazinyl, and 4-piperidopiperidinyl.

According to some embodiments of the present disclosure, particular compounds are of formula (1-A),

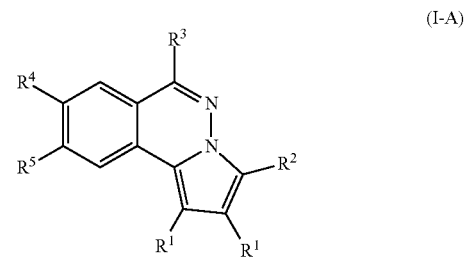

(I-A)

wherein, $R^1$ is an alkyl optionally substituted with halo, —OR, —OAc, —OSO$_2$R, or —OCONHR, wherein R is hydrogen, alkyl, cycloalkyl, or aryl;

$R^2$ is hydrogen, alkyl, cycloalkyl, aryl or heteroaryl;

$R^3$ is $NR^AR^B$, NHPhR$^C$, mono- or bis-saccharide(s) group, or an amino acid group, or —NR$^A$R$^B$ are taken together to form an optionally substituted aniline or cycloalkylamine selected from the group consisting of morpholine, pyrrolidine, piperidine, 1-substituted piperazine, 1,4'-bipiperidine, 4'-substituted 4,4'-bipiperidine; wherein the substituent on piperazine and 4,4'-bipiperidine is alky, —(CH$_2$)$_n$CONH(CH$_2$)$_m$NR$^A$R$^B$, in which n and m are independently an integral between 1 to 5, $R^A$ and $R^B$ are independently H or C$_{1-6}$ alkyl; and $R^C$ is hydrogen, halo, alkoxy, CH$_2$OH, NHCOR$_a$, NHC(O)OR$_a$, or optionally substituted alkyl, alkenyl, alkynyl, herocyclyl, or aryl, and R$_a$ is C$_{1-6}$ alkyl or aryl;

$R^4$ and $R^5$ are independently hydrogen, —OH, alkoxy, or —O(CH$_2$)$_x$N(R$_b$)$_2$, in which x is an integral between 1 to 5; and R$_b$ is C$_{1-10}$ alkyl, or a cycloalkylamino group; and the aryl or heteroaryl is optionally substituted with at least one substituent selected from the group consisting of C$_{1-6}$ alkyl, alkoxy, halo, cyano, nitro, —NH$_2$, —NHR$_c$, —N(R$_c$)$_2$, cyclolkylamino, methylenedioxy or ethylenedioxy group, in which It, is independently hydrogen or C$_{1-10}$ alkyl.

Exemplary compounds of formula (I-A) include, but not limited to, the followings:

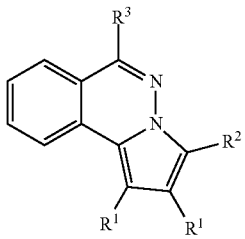

Formula I-A

| Compound No. | R³ | R² | R¹ |
|---|---|---|---|
| BO-2571 | morpholine | Me | —CH₂OH |
| BO-2577 | morpholine | Et | —CH₂OH |
| BO-2629 | morpholine | 4'-MeO—C₆H₄ | —CH₂OH |
| BO-2573 | morpholine | Me | —CH₂OCONHEt |
| BO-2625 | morpholine | Et | —CH₂OCONHEt |
| BO-2630 | morpholine | 4'-MeO—C₆H₄ | —CH₂OCONHEt |
| BO-2574 | morpholine | Me | —CH₂OCONH—i-Pr |
| BO-2626 | morpholine | Et | —CH₂OCONH—i-Pr |
| BO-2631 | morpholine | 4'-MeO—C₆H₄ | —CH₂OCONH—i-Pr |
| BO-2785 | dimethylamine | Me | —CH₂OH |
| BO-2686 | pyrrolidine | Me | —CH₂OH |
| BO-2720 | piperidine | Me | —CH₂OH |
| BO-2590 | 1,4'-bipiperidine | Me | —CH₂OH |
| BO-2786 | dimethylamine | Me | —CH₂OCONHEt |
| BO-2716 | pyrrolidine | Me | —CH₂OCONHEt |
| BO-2721 | piperidine | Me | —CH₂OCONHEt |
| BO-2742 | 1,4'-bipiperidine | Me | —CH₂OCONHEt |
| BO-2787 | dimethylamine | Me | —CH₂OCONH—i-Pr |
| BO-2717 | pyrrolidine | Me | —CH₂OCONH—i-Pr |
| BO-2722 | piperidine | Me | —CH₂OCONH—i-Pr |
| BO-2743 | 1,4'-bipiperidine | Me | —CH₂OCONH—i-Pr |

According to some embodiments of the present disclosure, particular compounds are of formula (I-B),

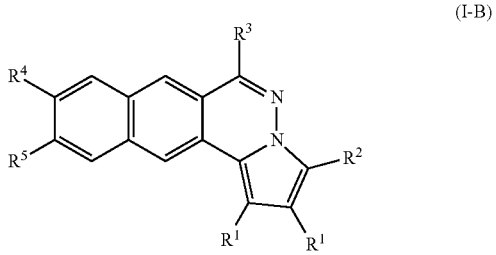

(I-B)

wherein,

R¹ is an alkyl optionally substituted with halo, —OR, —OAc, —OSO₂R, or —OCONHR, wherein R is hydrogen, alkyl, cycloalkyl, or aryl;

R² is hydrogen, alkyl, cycloalkyl, aryl or heteroaryl;

R³ is —NR$^A$R$^B$, NHPhR$^C$, mono- or bis-saccharide(s) group, or an amino acid group, or —NR$^A$R$^B$ are taken together to form an optionally substituted aniline or cycloalkylamine selected from the group consisting of morpholine, pyrrolidine, piperidine, 1-substituted piperazine, 1,4'-bipiperidine, 4'-substituted 4,4'-bipiperidine; wherein the substituent on piperazine and 4,4'-bipiperidine is alky, —(CH₂)$_n$CONH(CH₂)$_m$NR$^A$R$^B$, in which n and m are independently an integral between 1 to 5, R$^A$ and R$^B$ are independently H or C$_{1-6}$ alkyl; and R$^C$ is hydrogen, halo, alkoxy, —CH₂OH, —NHCOR$_a$, NHC(O)OR$_a$, or optionally substituted alkyl, alkenyl, alkynyl, herocyclyl, or aryl, and R$_a$ is C$_{1-6}$ alkyl or aryl;

R⁴ and R⁵ are independently hydrogen, —OH, alkoxy, or —O(CH₂)$_x$N(R$_b$)₂, in which x is an integral between 1 to 5; and R$_b$ is C$_{1-10}$ alkyl, or a cycloalkylamino group; and the aryl or heteroaryl is optionally substituted with at least one substituent selected from the group consisting of C$_{1-6}$ alkyl, alkoxy, halo, cyano, nitro, —NH₂, —NHR$_c$, —N(R$_c$)₂, cyclolkylamino, methylenedioxy or ethylenedioxy group, in which R$_c$ is independently hydrogen or C$_{1-10}$ alkyl.

Exemplary compounds of formula (I-B) include, but not limited to, the followings:

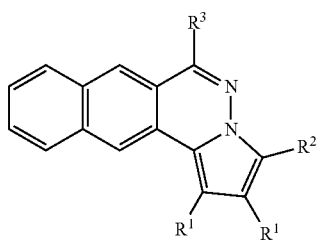

Formula I-B

| Compound No. | R³ | R² | R¹ |
|---|---|---|---|
| BO-2768 | dimethylamine | Me | —CH₂OH |
| BO-2762 | pyrrolidine | Me | —CH₂OH |
| BO-2755 | piperidine | Me | —CH₂OH |
| BO-2698 | morpholine | Me | —CH₂OH |
| BO-2792 | 1,4'-bipiperidine | Me | —CH₂OH |
| B0-2772 | dimethylamine | Me | —CH₂OCONHEt |
| BO-2763 | pyrrolidine | Me | —CH₂OCONHEt |
| BO-2757 | piperidine | Me | —CH₂OCONHEt |
| BO-2756 | morpholine | Me | —CH₂OCONHEt |
| BO-2793 | 1,4'-bipiperidine | Me | —CH₂OCONHEt |

Compounds of the invention contain one or more stereocenters, thus can exist as to racemic mixtures of enantiomers or mixtures of diastereomers. This invention thus encompasses stereomerically pure forms of such compounds, as well as mixtures of those forms. Stereoisomers may be asymmetrically synthesized or resolved using standard techniques such as crystallization, chromatography, and the use of a resolving agent. One preferred way of separating enantiomers from a racemic mixture is by use of preparative high performance liquid chromatography (HPLC). Alternatively, the racemic may be separated into its enantiomers by reacting with an optically active form of a resolving agent in the presence of a solvent. Depending on the optical form of the resolving agent, one of the two enantiomers is separated out as an insoluble salt with high yield and high optical purity, while the opposite enantiomer remains in the solution.

The present invention thus further encompasses stereoisomeric mixtures of compounds disclosed herein. It also encompasses configurational isomers of compounds disclosed herein (e.g., cis- and trans- isomers, whether or not involving double bonds), either in admixture or in pure or substantially pure form.

3. Method of Use

The present invention encompasses a method for the treatment or prophylaxis of a subject having a cancer. The method comprises the step of administering a therapeutically or prophylactically effective amount of the compound of formula (I) of the present disclosure to the subject, so as to suppress the growth of the cancer.

In some embodiments, the method further includes the step of administering to the subject a chemotherapeutic agent, before, together with, or after the administration of the compound of formula (I). The chemotherapeutic agent may be selected from the group consisting of, DET, PLX4032, docetaxel, paclitaxel, cisplatin, oxaliplatin, betulinic acid, 4-S-cysteaminyl catechol, 4-S-cysteaminyl phenol, everolimus, bortezomib, carboplatin, dacarbazine, celecoxib, temozolomide, sorafenib, thalidomide, lenalidomide, valproic acid, vinblastine, imatinib mesylate, bosentan, apomine, arsenic trioxide, carmustine, lambrolizuma, anti-CTLA-4 drug, anti-programmed death receptor-1 (PD-1) drug, ipilimumab, tremelimumab, doxorubicin, MEK inhibitor, capecitabine, poly (ADP-ribose) polymerase (PARP) inhibitor, phosphoinositide 3-kinase (PI3K) inhibitor, mammalian target of rapamycin (mTOR) inhibitor, and tamoxifen.

In the present disclosure, the cancer may be any of Hodgkin's disease, Non-Hodgkin's lymphomas, Acute Myelogenous Leukemia, Acute lymphoblastic leukemia, Chronic Myelogenous Leukemia, Ewing's sarcoma, multiple myeloma, Wilms' tumor, bone tumors, neuroblastoma, retinoblastoma, testicular cancer, thyroid cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small-cell lung cancer, brain cancer, melanoma, a non-melanoma skin cancer, or a CNS neoplasm. According to one preferred embodiment, the cancer treatable by the present compound of formula (I) is small-cell lung cancer. According to another preferred embodiment, the cancer treatable by the present compound of formula (1) is acute lymphoblastic leukemia.

The amount, route of administration and dosing schedule of the compound of formula (I) will depend upon factors such as the specific indication to be treated, prevented, or managed, and the age, sex and condition of the patient. The roles played by such factors are well known in the art, and may be accommodated by routine experimentation.

4. Pharmaceutical Formulation

This invention encompasses pharmaceutical compositions for the treatment or prophylaxis of a cancer. The pharmaceutical composition comprises a therapeutically or prophylactic effective amount of a compound of formula (I) of the present invention.

The compound of formula (I) is present at a level of about 0.1% to 99% by weight, based on the total weight of the pharmaceutical composition. In some embodiments, the compound of formula (I) is present at a level of at least 1% by weight, based on the total weight of the pharmaceutical composition. In certain embodiments, the compound of formula (I) is present at a level of at least 5% by weight, based on the total weight of the pharmaceutical composition. In still other embodiments, the compound of formula (I) is present at a level of at least 10% by weight, based on the total weight of the pharmaceutical composition. In still yet other embodiments, the compound of formula (I) is present at a level of at least 25% by weight, based on the total weight of the pharmaceutical composition.

In some preferred embodiments, the pharmaceutical composition further comprises a chemotherapeutic agent. The chemotherapeutic agent may be selected from the group consisting of, DET, PLX4032, docetaxel, paclitaxel, cisplatin, oxaliplatin, betulinic acid, 4-S-cysteaminyl catechol, 4-S-cysteaminyl phenol, everolimus, bortezomib, carboplatin, dacarbazine, celecoxib, temozolomide, sorafenib, thalidomide, lenalidomide, valproic acid, vinblastine, imatinib mesylate, bosentan, apomine, arsenic trioxide, carmustine, lambrolizuma, anti-CTLA-4 drug, anti-programmed death receptor-1 (PD-1) drug, ipilimumab, tremelimumab, doxorubicin, MEK inhibitor, capecitabine, poly (ADP-ribose) polymerase (PARP) inhibitor, phosphoinositide 3-kinase (PI3K) inhibitor, mammalian target of rapamycin (mTOR) inhibitor, and tamoxifen.

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intra-arterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., α-cyclodextrin or β-cyclodextrin), and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO:corn oil), lipids such as egg york phosphatidylcoline (EPC), soybean phosphatidylcholine (SPC), 1,2-dioleoyl-sn-glycero-3-phosphocholine (DOPC), 1,2-distearoyl-sn-glycero-3- phosphocholine (DSPC), cholesterol (CHO), dipalmitoylphosphatidylcholine (DPPC) and PEG-2000. According to one preferred embodiment, the compound of formula (I) (i.e., BO-2590) is incorporated into lipids to form liposomes suitable for oral or parenteral administration.

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

4.1 Oral Dosage Forms

Pharmaceutical compositions of the present invention suitable for oral administration can be presented as discrete dosage forms, such as, but are not limited to, tablets (e.g., chewable tablets), caplets, capsules, and liquids (e.g., flavored syrups).

Such dosage forms contain predetermined amounts of active ingredients, and may be prepared by methods of pharmacy well known to those skilled in the art. See, e.g., *Remington's Pharmaceutical Sciences,* 18th ed., Mack Publishing, Easton Pa. (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Dis-integrants may be incorporated in solid dosage forms to facility rapid dissolution. Lubricants may also be incorporated to facilitate the manufacture of dosage forms (e.g., tablets).

4.2 Parenteral Dosage Forms

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: water; aqueous vehicles such as, but not limited to, sodium chloride solution, Ringer's solution, and Dextrose; water-miscible vehicles such as, but not limited to, ethyl alcohol, polyethylene glycol, and polypropylene glycol; and non-aqueous vehicles such as, but not limited to, lipids, corn oil, cottonseed oil, peanut oil, sesame oil, ethyl oleate, isopropyl myristate, and benzyl benzoate.

4.3 Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 18th eds., Mack Publishing, Easton Pa. (1990). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition 5. Kits Also encompasses within the present disclosure are kits useful for treatment or prophylaxis of a cancer in a subject.

The Kit according to present disclosure include, at least, a first container containing the present compound of formula (1), a second container containing a chemotherapeutic agent as described above; and a legend associated with the kit for instructing a user how to use the kit. The legend may be in a form of pamphlet, tape, CD, VCD or DVD. Examples of the container include, but are not limited to, vials, tubes, and the like.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods
Cell Culture

Each type of cells used in the present study were grown in manufactures' suggested medium supplemented with 10% heat-inactivated fetal bovine serum, 100 units/mL penicillin, and 100 µg/mL streptomycin, at 37° C. in a humidified 5% $CO_2$ incubator.

Animals

Animal care was approved and handled by following the guidelines of the Academia Sinica Institutional Animal and Utilization Committee.

Athymic nude mice bearing the nu/nu gene were obtained from the National Laboratory Animal Center (Taipei, Taiwan). Male nude mice (6 weeks or older weighing 20-24 g or more) were used for all human tumor xenografts. The tested compounds were intravenously administered through tail vein. Tumor volume was determined by measuring the length x width x height (or width) with calipers. The vehicle used for the tested compounds was normal saline (0.9% NaCl isotonic solution). For tumor-bearing nude mice during the course of the experiment, the % body weight changes refer to: (the total weight on reading day/the total weight on day treatment started)×100.

Example 1 Chemical Synthesis of 1,2-bis(hydroxymethyl)pyrrolo[2,1-a]-phthalazine phthalazine Derivatives (Formula (I-A)) (Scheme 1)

Compounds of Formula (I-A) were synthesized in accordance with the procedures described in Scheme 1. The commercially available 1-pthalazinone 19 was treated with phosphorus oxychloride to give compound 20, which was further treated with various ω-N,N-dialkylalkylamines, cyclic amines, anilines, 1-methylpiperazine, 1-ethylpiperazine, 1-methyl-4,4'-bipiperidine, or 1-ethyl-4,4'-bipiperidine in ethanol to afford compound 21. Compound 21 could then react with trimethyl silylcyanide (TMSCN) and alkyl or aryl chloride in dichloromethane to yield compound 22, which was converted into hydrofluoroborate salt by treating with tetrafluoro boric acid (HBF4) in ether, followed by dimethyl acetylenedicarboxylate (DMAD), to give the diester derivative 23. The diester function of 23 was reduced to the corresponding bis(hydroxymethyl) derivative 24 by reacting with $LiAlH_4$ in a mixture of ether/$CH_2Cl_2$ in an ice bath. Similarly, the bis(hydroxymethyl) derivatives 24 were converted into their corresponding bis(alkylcarbamates) congeners by reacting with various isocyanates to give compound 25 (wherein $R^1$ is —$CH_2$OCONHR, R is alkyl or aryl), or treating with acid anhydride in pyridine to give compound 25 (wherein $R^1$ is —$CH_2$OCOR), or by reacting with toluene- or methanesulfonyl chloride/$Et_3$N to give compound 25 (wherein $R^1$ is —$CH_2$OSO$_2$R, R is Me or 4-MePh), and other good leaving group.

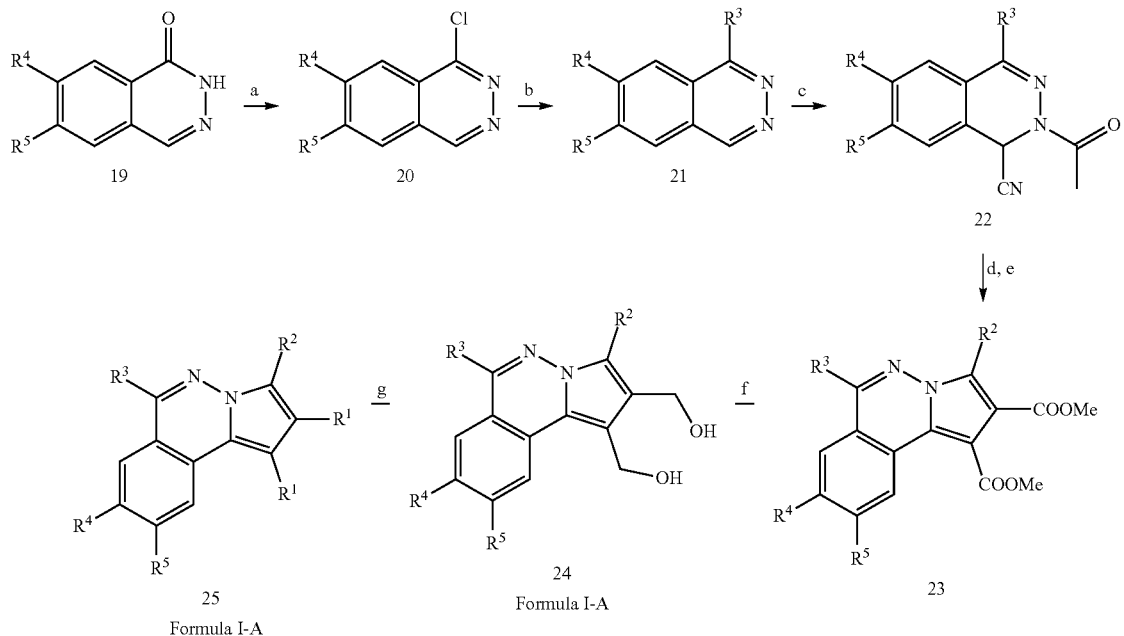

Scheme 1

Reagent and conditions: a) $POCl_3$, reflux; b) $R^3NH_2$, Ethanol, reflux;, c) TMSCN, $AlCl_3$, $R^2$COCl, DCM; d) $HBF_4$, AcOH; e) DMAD, DMF, reflux; f) $LiAlH_4$, THF; g) RNCO, THF Exemplary compounds of formula (I-A) thus obtained include the followings:

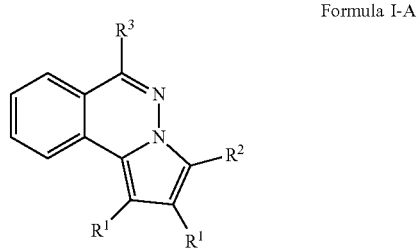

Formula I-A

| Compound No. | $R^3$ | $R^2$ | $R^1$ | mp ° C. |
|---|---|---|---|---|
| BO-2571 | morpholine | Me | —$CH_2$OH | 184-182 |
| BO-2577 | morpholine | Et | —$CH_2$OH | 180-182 |
| BO-2629 | morpholine | 4'-MeO—$C_6H_4$ | —$CH_2$OH | 190-192 |
| BO-2573 | morpholine | Me | —$CH_2$OCONHEt | 171-173 |
| BO-2625 | morpholine | Et | —$CH_2$OCONHEt | 165-167 |

-continued

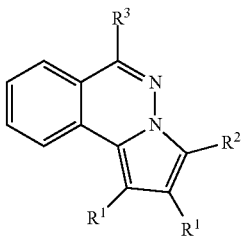

Formula I-A

| Compound No. | R³ | R² | R¹ | mp °C. |
|---|---|---|---|---|
| BO-2630 | morpholine | 4'-MeO—C₆H₄ | —CH₂OCONHEt | 168-170 |
| BO-2574 | morpholine | Me | —CH₂OCONH—i-Pr | 159-161 |
| BO-2626 | morpholine | Et | —CH₂OCONH—i-Pr | 147-149 |
| BO-2631 | morpholine | 4'-MeO—C₆H₄ | —CH₂OCONH—i-Pr | 152-154 |
| BO-2785 | dimethylamine | Me | —CH₂OH | 164-166 |
| BO-2686 | pyrrolidine | Me | —CH₂OH | 160-162 |
| BO-2720 | piperidine | Me | —CH₂OH | 159-161 |
| BO-2590 | 1,4'-bipiperidine | Me | —CH₂OH | 183-185 |
| BO-2786 | dimethylamine | Me | —CH₂OCONHEt | 149-151 |
| BO-2716 | pyrrolidine | Me | —CH₂OCONHEt | 140-142 |
| BO-2721 | piperidine | Me | —CH₂OCONHEt | 158-152 |
| BO-2742 | 1,4'-bipiperidine | Me | —CH₂OCONHEt | 154-156 |
| BO-2787 | dimethylamine | Me | —CH₂OCONH—i-Pr | 154-156 |
| BO-2717 | pyrrolidine | Me | —CH₂OCONH—i-Pr | 160-162 |
| BO-2722 | piperidine | Me | —CH₂OCONH—i-Pr | 141-142 |
| BO-2743 | 1,4'-bipiperidine | Me | —CH₂OCONH—i-Pr | 161-163 |

1.1 (3-methyl-6-morpholinopyrrolo[2,1]-alphthalazine-1,2-diyl)-dimethanol (BO-2571) and (3-Methyl-6-morpholinopyrrolo[2,1-a]-phthalazine-1,2-diyl)bis(methylene) bis(ethylcarbamate) (BO-2573)

(1) 1-Chlorophthalazine

A mixture of the commercially available phthalazin-1(2H)-one (5.0 g, 34.0 mmol) and phosphorus oxychloride (POCl₃) (25 mL) was heated with stirring at 100° C. for 2 h. After cooling to room temperature, the excess POCl₃ was completely distilled out under reduced pressure. The residue was triturated with toluene (2×25 mL) and followed with THF (100 mL), and the solid product was collected by filtration and washed with THF. The product was then dissolved in DCM, washed with saturated aqueous NaHCO₃ solution, dried over sodium sulfate and evaporated under reduced pressure to give 1-chlorophthalazine. Yield 4.6 g (82%); mp 119-121° C. (lit.[33] mp 132-134° C.).

¹H NMR (DMSO-d₆) δ 8.20 (2H, t, J=7.2 Hz, ArH), 8.33 (2H, t, J=7.6 Hz, ArH), 9.73 (1H, s, ArH).

¹³C NMR (DMSO-d₆) δ 126.1, 128.4, 128.7, 155.3. HRMS [ESI⁺]: calculated for C₈H₅ClN₂, 165.0220 [M+H]⁺, found 165.0212.

(2) 4-(Phthalazin-1-yl)morpholine

To a solution of 1-chlorophthalazine (3.64 g, 20.0 mmol) in ethanol (120 mL) containing triethylamine (6.96 mL, 50.0 mmol) was added dropwise morpholine (1.89 mL, 22.0 mmol). The reaction mixture was heated at reflux for 18 h and the solvent was removed under reduced pressure to dryness. The reaction was cooled to rt and solvent was evaporated. The crude product obtained was diluted with water and was extracted with DCM twice. The separated organic layer was dried over sodium sulfate and evaporated under vacuo to give 4-(phthalazin-1-yl)morpholine. Brown solid; Yield 3.8 g (80%); mp 125-127° C. (lit.' mp 82° C.).

¹H NMR (DMSO-d₆) δ 3.40 (4H, t, J=4.8 Hz, 2×CH₂), 3.88 (4H, t, J=4.4 Hz, 2×CH₂), 7.94-7.97 (2H, m, ArH), 8.09-8.14 (2H, m, ArH), 9.31 (1H, s, ArH).

¹³C NMR (DMSO-d₆) δ 51.4, 51.7, 66.5, 120.7, 124.4, 124.5, 127.5, 128.5, 132.4, 132.5, 148.4, 159.7. HRMS [ESI⁺]: calculated for C₁₂H₁₃N₃O, 216.1137[M+H]⁺, found 216.1094.

(3) 2-Acetyl-4-morpholino-1,2-dihydrophthalazine-1-carbonitrile

To a solution of 4-(phthalazin-1-yl)morpholine (2.0 g, 9.3 mmol) in DCM (30 mL) containing catalytic amount of AlCl₃ was added dropwise Me₃SiCN (2.32 mL, 18.6 mmol). Acetyl chloride (1.0 mL, 14.0 mmol) was then added dropwise to the above mixture and stirred for 4 h at rt. The reaction mixture was poured into ice-water and the organic layer was washed successfully with water, 5% NaOH solution and water. The solution was drid over sodium sulfate and concentrated in vacuo to give 2-acetyl-4-morpholino-1,2-dihydrophthalazine-1-carbonitrile. Yield 2.36 g (89%); mp 140-142° C.

¹H NMR (CDCl₃) δ 2.32 (3H, s, CH₃), 3.13-3.18 (2H, m, CH₂), 3.44-3.49 (2H, m, CH₂), 3.81-3.86 (2H, m, CH₂), 3.94-3.99 (2H, m, CH₂), 6.70 (1H, s, CH), 7.43 (1H, d, J=7.6 Hz, ArH), 7.51-7.59 (3H, m, ArH).

¹³C NMR (CDCl₃) δ 16.9, 49.8, 55.8, 66.7, 116.4, 121.5, 124.0, 123.7, 129.2, 130.3, 132.8, 155.5, 169.6. HRMS [ESI⁺]: calculated for C₁₅H₁₆N₄O₂, 285.1352[M+H]⁺, found 285.1341.

(4) Dimethyl-3-methyl-6-morpholinopyrrolo [2,1-α]phthalazine-1,2-dicarboxylate

To a solution of 2-acetyl-4-morpholino-1,2-dihydrophthalazine-1-carbonitrile (2.0 g, 7.0 mmol) in warm acetic acid (50 mL) was added dropwise HBF₄ (1.55 mL). The mixture was allowed to stir at 50-60° C. for 30 min. After cooling to rt, the yellow solid salt was collected by filtration and the filter cake was washed with dry ether. The solid salt was dissolved in DMF (20 mL) and DMAD (1.6 mL, 13 mmol) was added slowly to this solution. The reaction mixture was heated at 90-100° C. for 16 h. The solvent was removed by evaporation in vacuo. The residue was crystallized from MeOH to give dimethyl-3-methyl-6-morpholinopyrrolo [2,1-a]phthalazine-1,2-dicarboxylate. Yield 1.5 g (56%); mp 182-183° C.

¹H NMR (DMSO-d₆) δ 2.64 (3H, s, CH₃), 3.30-3.31 (4H, m, 2×CH₂), 3.80 (3H, s, COOCH3), 3.87 (3H, s, COOCH3), 3.87-3.88 (4H, m, 2×CH₂), 7.64 (1H, t, J=8.0 Hz, ArH), 7.81 (1H, t, J=7.5 Hz, ArH), 8.06 (1H, d, J=8.0 Hz, ArH), 8.25 (1H, d, J=8.5 Hz, ArH).

¹³C NMR (DMSO-d₆) δ 13.9, 52.4, 52.7, 55.6, 66.2, 106.7, 115.8, 117.7, 121.0, 124.6, 126.7, 128.9, 130.3, 133.0, 156.2, 159.7, 165.6, 165.9; HRMS [ESI⁺]: calculated for C₂₀H₂₁N₃O₅, 406.1379[M+Na]⁺, found 406.1385.

(5) Dimethyl-3-methyl-6-morpholinopyrrolo [2,1a]-cilphthalazine-1,2-dicarboxylate To a solution of dimethyl-3-methyl-6-morpholinopyrrolo[2,1-a]phthalazine-1,2-dicarboxylate (2.0 g, 7.0 mmol) in warm acetic acid (50 mL) was added dropwise $HBF_4$ (1.55 mL). The mixture was allowed to stir at 50-60° C. for 30 min. After cooling to rt, the yellow solid salt was collected by filtration and the filter cake was washed with dry ether. The solid salt was dissolved in DMF (20 mL) and DMAD (1.6 mL, 13 mmol) was added slowly to this solution. The reaction mixture was heated at 90-100° C. for 16 h. The solvent was removed by evaporation in vacuo. The residue was crystallized from MeOH to give dimethyl-3-methyl-6-morpholinopyrrolo[2,1-α]phthalazine-1,2-dicarboxylate. Yield 1.5 g (56%); mp 182-183° C.

$^1$H NMR (DMSO-$d_6$) δ 2.64 (3H, s, $CH_3$), 3.30-3.31 (4H, m, $2\times CH_2$), 3.80 (3H, s, $COOCH3$), 3.87 (3H, s, $COOCH3$), 3.87-3.88 (4H, m, $2\times CH_2$), 7.64 (1H, t, J=8.0 Hz, ArH), 7.81 (1H, t, J=7.5 Hz, ArH), 8.06 (1H, d, J=8.0 Hz, ArH), 8.25 (1H, d, J=8.5 Hz, ArH).

$^{13}$C NMR (DMSO-$d_6$) δ 13.9, 52.4, 52.7, 55.6, 66.2, 106.7, 115.8, 117.7, 121.0, 124.6, 126.7, 128.9, 130.3, 133.0, 156.2, 159.7, 165.6, 165.9; HRMS [ESI$^+$]: calculated for $C_{20}H_{21}N_3O_5$, 406.1379[M+Na]$^+$, found 406.1385.

(6) (3-Methyl-6-morpholinopyrrolo[2,1-α]phthalazine-1,2-diyl)dimethanol (BO-2571)

A solution of dimethyl-3-methyl-6-morpholinopyrrolo[2,1-a]phthalazine-1,2-dicarboxylate (1.5 g, 3.9 mmol) in DCM (50 mL) was added dropwise to a stirred suspension of LAH (0.37 g, 9.7 mmol) in diethyl ether (20 mL) at 0-5° C. After completion of the reaction in 2 h, the excess of LAH was decomposed by the addition of water (2 mL) and $NH_4OH$ (2 mL). The reaction mixture was filtered through a pad of Celite and washed well with DCM. The combined filtrate and washings were evaporated in vacuo to dryness. The residue was recrystallized from ethanol to give (3-methyl-6-morpholinopyrrolo[2,1-a]phthalazine-1,2-diyl)dimethanol (BO-2571). Yield 1.0 g, (80%), mp 184-186° C.

$^{13}$-H NMR (DMSO-$d_6$) δ 2.46 (3H, s, $CH_3$), 3.23 (4H, s, $2\times CH_2$), 3.87 (4H, s, $2\times CH_2$), 4.58 (3H, s, $1\times OCH_2$ and $1\times OH$), 4.78-4.83 (3H, m, $1\times OCH_2$ and $1\times OH$), 7.45 (1H, t, J=7.5 Hz, ArH), 7.73 (1H, t, J=7.5 Hz, ArH), 7.97 (1H, d, J=8.0 Hz, ArH), 8.29 (1H, d, J=7.5 Hz, ArH).

$^{13}$C NMR (DMSO-$d_6$) δ 9.3, 51.9, 53.8, 54.4, 66.5, 114.4, 115.7, 118.3, 121.6, 123.2, 123.6, 125.3, 126.0, 130.2, 132.3, 1541 HRMS [ESI$^+$]: calculated for $Ci8H2iN3O3$, 310.1556 [M+H–$H_2O$]$^+$, found 310.1569.

(7) (3-Methyl-6-morpholinopyrrolo[2, 1-a]phthalazine-1,2-diyl)bis(methylene)bis(ethylcarbamate) (BO-2573)

A mixture of 3-methyl-6-morpholinopyrrolo[2,1-a]phthalazine-1,2-diyl)-dimethanol (0.15 g, 0.5 mmol), TEA (0.25 mL, 2.0 mmol) and ethyl isocyanate (0.15 mL, 2.0 mmol) in dry DMF was stirred for 24-48 h at rt under argon. After completion of the reaction, the reaction mixture was evaporated to dryness in vacuo. The residue was triturated with ether and the desired product was collected by filtration to give (3-methyl-6-morpholinopyrrolo[2, 1-a]phthalazine-1,2-diyl)bis(methylene) bis(ethylcarbamate) (BO-2573). Yield 0.16 g (75%); mp 171-173° C.

$^1$H NMR (DMSO-$d_6$) δ 0.97 (6H, t, J=6.5 Hz, $2\times CH_3$), 2.46 (3H, s, $CH_3$), 2.97-2.98 (4H, m, $2\times CH_2$), 3.22 (4H, s, $2\times CH_2$), 3.85 (4H, s, $2\times CH_2$), 5.17 (2H, s, $OCH_2$), 5.38 (2H, s, $OCH_2$), 7.01 (2H, brs, $2\times NH$), 7.49 (1H, t, J=7.5 Hz, ArH), 7.76 (1H, t, J=7.0 Hz, ArH), 7.99 (1H, d, J=8.0 Hz, ArH), 8.10 (1H, d, J=7.0 Hz, ArH).

$^{13}$C NMR (DMSO-$d_6$) δ 9.35, 15.5, 35.4, 51.9, 56.5, 57.3, 66.4, 109.5, 116.1, 117.6, 119.2, 122.9, 125.2, 126.2, 129.6, 132.7, 154.6, 156.5, 156.6. HRMS [ESI$^+$]: calculated for $C_{24}H_{31}N_5O_5$, 294.1606[M+H–2($OCONHC_2H_5$)]$^+$, found 294.1602.

1.2 (3-methyl-6-(pyrrolidin-1-yl)pyrrolo[2,1-a]phthalazine-1,2 diyl)dimethanol (BO-2686) and (3-methyl-6-(pyrrolidin-1-yl)prolog- [2,1-a]phthalazine-1,2-diyl)bis(methylene) bis(ethylcarbamate) (BO-2716)

(1) 1-(Pyrrolidin-1-yl)phthalazine

Pyrrolidine (20.0 mL, 240.0 mmol) was added slowly to a solution of 1-chloropthalazine (10.0 g, 60.0 mmol) in ethanol (200 mL) containing TEA (30.0 mL, 200.0 mmol). The reaction mixture was stirred at rt for 48 h. After completion of reaction, the solvent was evaporated and the residue was diluted with water and then extracted with DCM (2×200 mL). The organic layer was dried over sodium sulfate and evaporated in vacuo to give the desired product 1-(pyrrolidin-1-yl)phthalazine. Yield 10.0 g (83%); mp 90-91° C.

$^1$H NMR (DMSO-d6) δ $^1$H NMR (DMSO-d6) δ 1.95-1.98 (4H, m, $2\times CH_2$), 3.82 (4H, t, J=6.5 Hz, $2\times CH_2$), 7.80-7.88 (2H, m, ArH), 7.94-7.95 (1H, m, ArH), 8.28 (1H, d, J=8.5 Hz, ArH), 8.97 (1H, s, ArH).

$^{13}$C NMR (DMSO-$d_6$) δ 25.8, 51.1, 119.2, 125.2, 126.5, 128.7, 130.9, 131.6, 144.1, 155.7. HRMS [ESI+]: calculated for $C_{12}H_{13}N_3$, 200.1188[M+H]$^+$, found 200.1209.

(2) 2-Acetyl-4-(pyrrolidin-1-yl)-1,2-dihydrophthalazine-1-carbonitrile

To a solution of 1-(pyrrolidin-1-yl)phthalazine (5.0 g, 25.0 mmol) in DCM (30 mL) containing catalytic amount of $AlCl_3$ was added dropwise Me3SiCN (6.3 mL, 50.0 mmol). Acetyl chloride (2.7 mL, 37.5 mmol) was then added dropwise to the above mixture and stirred for 4 h at rt. The reaction mixture was poured into ice-water and the organic layer was washed successfully with water, 5% NaOH solution and water. The solution was drid over sodium sulfate and concentrated in vacuo to give 2-acetyl-4-(pyrrolidin-1-yl)-1,2-dihydrophthalazine-1-carbonitrile. Yield 5.7 g (85%); mp 123-125° C.

$^1$H NMR (DMSO-$d_6$) δ 1.83 (2H, t, J=6.8 Hz, $CH_2$) 2.00 (2H, s, $CH_2$), 2.21 (3H, s, $CH_3$), 3.28-3.34 (2H, m, $CH_2$), 3.70-3.75 (2H, m, $CH_2$), 7.06 (1H, s, CH), 7.59-7.66 (2H, m, ArH), 7.81 (2H, d, J=7.4 Hz, ArH).

$^{13}$C NMR (DMSO-$d_6$) δ 20.8, 25.3,49.8, 116.9, 122.7, 126.7, 127.3, 129.7, 130.4, 132.3, 153.5, 170.8. HRMS [ESI$^+$]: calculated for $C_{15}H_{16}N_4O$, 269.1402[M+H]$^+$, found 269.1416.

(3) Dimethyl-3-methyl-6-(pyrrolidin-1-yl)pyrrolo[2,1-a]phthalazine-1,2-dicarboxylate To a solution of 2-acetyl-4-(pyrrolidin-1-yl)-1,2-dihydrophthalazine-1-carbonitrile (5.0 g, 18.6 mmol) in warm acetic acid (50 mL) was added dropwise HBF4 (3.6 mL). The mixture was allowed to stir at 50-60° C. for 30 min. After cooling to rt, the yellow solid salt was collected by filtration and the filter cake was washed with dry ether. The solid salt was dissolved in DMF (20 mL) and DMAD (4.5 mL, 37.0 mmol) was added slowly to this solution. The reaction mixture was heated at 90-100° C. for 16 h. The solvent was removed by evaporation in vacuo. The residue was crystallized from MeOH to give dimethyl-3-methyl-6-(pyrrolidin-1-yl)pyrrolo[2, 1-α]-phthalazine-1,2-dicarboxylate. Yield 2.5 g (48%); mp 176-178° C.

$^1$H NMR (DMSO-d6) 1.92 (4H, s, $2\times CH_2$), 2.57 (3H, s, $CH_3$), 3.65 (4H, s, $2\times CH_2$), 3.78 (3H, s, $COOCH_3$), 3.86 (3H, s, $COOCH_3$), 7.55 (1H, t, J=7.7 Hz, ArH), 7.73 (1H, t, J=7.7 Hz, ArH), 8.14 (1H, d, J=8.2 Hz, ArH), 8.20 (1H d, J=8.1 Hz, ArH).

$^{13}$C NMR (DMSO-d$_6$) δ 10.5, 25.7, 51.3, 51.9, 52.7, 106.7, 111.7, 117.8, 120.1, 123.0, 127.4, 127.7, 128.1, 129.4, 132.4, 153.7, 165.0, 167.3. HRMS [ESI$^+$]: calculated for C$_{20}$H$_{21}$N$_3$O$_4$, 368.1610[M+H]$^+$, found 368.1581.

(4) (3-Methyl-6-(pyrrolidin-1-yl)pyrrolo[2,1-a]phthalazine-1,2 diyl)dimethanol (BO-2686)

A solution of dimethyl-3-methyl-6-(pyrrolidin-1-yl)pyrrolo[2,1-α]-phthalazine-1,2-dicarboxylate (2.2 g, 6.23 mmol) in DCM (50 mL) was added dropwise to a stirred suspension of LAH (0.6 g, 15.5 mmol) in diethyl ether (50 mL) at 0-5° C. After completion of the reaction in 2 h, the excess of LAH was decomposed by the addition of water (2 mL) and NH$_4$OH (2 mL). The reaction mixture was filtered through a pad of Celite and washed well with DCM. The combined filtrate and washings were evaporated in vacuo to dryness. The residue was recrystallized from ethanol to give (3-methyl-6-(pyrrolidin-1-yl)pyrrolo[2, 1-α]phthalazine-1,2-diyl)dimethanol (BO-2686). Yield 1.6 g (83%), mp 160-162° C.

$^1$H NMR (DMSO-d$_6$) δ 1.94 (4H t, J=6.5 Hz, 2×CH$_2$), 2.42 (3H, s, CH$_3$), 3.58 (4H , t, J=6.4 Hz, 2×CH$_2$), 4.51-4.56 (3H, m, 1×OH and 1×OCH$_2$), 4.72 (1H, t, J=5.2 Hz, OH), 4.80 (2H, d, J=5.1 Hz, OCH$_2$), 7.38-7.41 (1H, m, ArH), 7.68-7.71 (1H, m, ArH), 8.05 (1H, d, J=8.1 Hz, ArH), 8.26 (1H, d, J=8.0 Hz, ArH).

$^{13}$C NMR (DMSO-d$_6$) δ 9.3, 25.3, 51.3, 53.8, 54.5, 113.8, 116.6, 117.9, 120.8, 122.4, 123.3, 124.7, 126.7, 130.3, 131.8, 152.5. HRMS [ESI$^+$]: calculated for C$_{18}$H$_{21}$N$_3$O$_2$ 294.1606[M+H–H$_2$O]$^+$, found 294.1627.

(5) (3-Methyl-6-(pyrrolidin-1-yl)pyrrolo[2, 1-a]phthalazine-1,2-diyl)-bis(methylene) bis(ethylcarbamate) (BO-2716)

A mixture of (3-methyl-6-(pyrrolidin-1-yl)pyrrolo[2,1-a]phthalazine-1,2-diyl)-dimethanol (0.15 g, 0.5 mmol), (0.16 g, 0.5 mmol), ethyl isocyanate (0.2 mL, 2.0 mmol) and TEA (0.3 mL, 2.0 mmol) in dry DMF was stirred for 24-48 h at rt under argon. After completion of the reaction, the reaction mixture was evaporated to dryness in vacuo. The residue was triturated with ether and the desired product was collected by filtration to give (3-methyl-6-(pyrrolidin-1-yl)pyrrolo[2, 1-a]phthalazine-1,2-diyl)bis(methylene) bis(ethylcarbamate) (BO-2716). Yield 0.13 g, (70%); mp 140-142° C.

$^1$H NMR (DMSO-d6) δ 0.96-0.99 (6H, m, 2×CH$_3$), 1.93 (4H, t, J=6.5 Hz, 2×CH$_2$), 2.43 (3H, s, CH$_3$), 2.96-3.00 (4H, m, 2×CH$_2$), 3.60 (4H, s, 2×CH$_2$), 5.15 (2H, s, OCH$_2$), 5.36 (2H, s, OCH$_2$), 6.98-7.03 (2H, m, 2×NH), 7.46 (1H, t, J=7.3 Hz, ArH), 7.72 (1H, t, J=7.3 Hz, ArH), 8.06 (1H, d, J=8.4 Hz, ArH), 8.10 (1H, d, J=8.2 Hz, ArH).

$^{13}$C NMR (DMSO-d$_6$) δ 9.3, 15.5, 25.4, 35.5, 51.3, 56.6, 57.5, 108.8, 116.8, 117.0, 118.8, 122.6, 125.6, 127.1, 129.7, 132.2, 152.9, 156.6, 156.7. HRMS [ESI$^+$]: calculated for C$_{24}$H$_{31}$N$_5$O$_4$, 278.1657[M+H–2(OCONHC$_2$H$_5$)]$^+$, found 278.1660.

1.3 (6-([1,4'-bipiperidin]-1'-yl)-3-methylpyrrolo[2,1-α]phthalazine-1,2-diyl)dimethanol (BO-2590)

(1) 1-([1,4'-Biperidin]-1'-yl)phthalazine 1,4'-Bipiperidine (20.0 g, 120.0 mmol) was added slowly to a solution of 1-chlorpthalazine (10.0 g, 60.0 mmol) in ethanol (200 mL) containing TEA (34 mL, 240.0 mmol). The reaction mixture was stirred at rt for 48 h. After completion of reaction, the solvent was evaporated and the residue was diluted with water and then extracted with DCM (2×200 mL). The organic layer was dried over sodium sulfate and evaporated in vacuo to give the desired product 1-([1,4'-bipiperidin]-1'-yl)phthalazine. Yield 10.2 g (57%); mp 140-142° C.

$^1$H NMR (DMSO-d$_6$) δ 1.37-1.42 (2H, m, CH$_2$), 1.48-1.53 (4H, m, CH$_2$), 1.75-1.81 (2H, m, CH$_2$), 1.88-1.91 (2H, m, CH$_2$), 2.43 (1H, s, CH), 2.57 (4H, s, 2×CH$_2$), 2.94-3.00 (2H, m, CH$_2$), 3.87-3.90 (2H, m, CH$_2$), 7.92-7.94 (2H, m, ArH), 8.04-8.06 (2H, m, ArH), 9.25 (1H, s, ArH). HRMS [ESI+]: calculated for C$_{18}$H$_{24}$N$_4$, 297.2079 [M+H]$^+$, found 297.2092.

(2) 4-([1,4'-Biperidin]-1'-yl)-2-acetyl-1,2-dihydrophthalazine-1-carbonitrile

To a solution of 1-([1,4'-bipiperidin]-1'-yl)phthalazine (2.0 g, 6.7 mmol) in DCM (30 mL) containing catalytic amount of AlCl$_3$ was added dropwise Me$_3$SiCN (1.69 mL, 13.5 mmol). Acetyl chloride (0.88 mL, 10.0 mmol) was then added dropwise to the above mixture and stirred for 4 h at rt. The reaction mixture was poured into ice-water and the organic layer was washed successively with water, 5% NaOH solution and water. The solution was dried over sodium sulfate and concentrated in vacuo to give 4-([1,4'-bipiperidin]-1'-yl)-2-acetyl-1,2-dihydrophthalazine-1-carbonitrile. Yield 1.45 g, (60%); mp 160-162° C.

$^1$H NMR (DMSO-d$_6$) δ 1.42-1.45 (1H, m, CH$_2$), 1.70-1.82 (6H, m, 3×CH$_2$), 2.10-2.26 (6H, m, 3×CH$_2$), 2.65 (3H, s, CH$_3$), 2.66-2.73 (1H, m, CH), 2.95-3.00 (3H, m, CH$_2$), 3.76 (1H, d, J=7.0 Hz, CH$_2$), 3.88 (1H, d, J=4.5 Hz, CH$_2$), 7.00 (1H, s, CH), 7.61-7.69 (3H, m, ArH), 7.82 (1H, d, J=7.2 Hz, ArH). HRMS [ESI$^+$]: calculated for C$_{21}$H$_{27}$N$_5$O, 366.2294[M+H]$^+$, found 366.2308.

(3) Dimethyl-6-([1,4'-bipiperidin]-1'-yl)-3-methylpyrrolo[2,1-α]phthalazine-1,2-dicarboxylate To a solution of 4-([1,4'-bipiperidin]-1'-yl)-2-acetyl-1,2-dihydrophthalazine-1-carbonitrile (1.3 g, 3.5 mmol) in warm acetic acid (50 mL) was added dropwise HBF4 (0.7 mL). The mixture was allowed to stir at 50-60° C. for 30 min. After cooling to rt, the yellow solid salt was collected by filtration and the filter cake was washed with dry ether. The solid salt was dissolved in DMF (20 mL) and DMAD (0.8 mL, 6.5 mmol) was added slowly to this solution. The reaction mixture was heated at 90-100° C. for 16 h. The solvent was removed by evaporation in vacuo. The residue was crystallized from MeOH to give dimethyl-6-([1,4'-bipiperidin]-1'-yl)-3-methylpyrrolo[2,1-α]- phthalazine-1,2-dicarboxylate. Yield 1.0 g (70%); mp 189-191° C.

$^1$H NMR (DMSO-d$_6$) δ 1.43-1.46 (3H, m, CH$_2$), 1.68-1.72 (2H, m, CH$_2$), 1.88 (2H, s, CH$_2$), 2.02-2.04 (2H, m, CH$_2$), 2.14-2.16 (2H, m, CH$_2$), 2.65 (3H, s, CH$_3$), 3.01 (4H, m, 2×CH$_2$), 3.17 (1H, s, CH), 3.49-3.51 (3H, m, CH$_2$), 3.81 (3H, s, COOCH$_3$), 3.86-3.88 (2H, m, CH$_2$), 3.89 (3H, s, COOCH$_3$), 7.66 (1H, t, J=8.0 Hz, ArH), 7.83 (1H, t, J=7.2 Hz, ArH), 8.00 (1H, d, J=8.4 Hz, ArH), 8.27 (1H, d, J=8.4 Hz, ArH).

$^{13}$C NMR (DMSO-d$_6$) δ 12.6, 24.5, 26.2, 28.1, 50.4, 51.5, 58.2, 58.9, 67.5, 70.4, 111.6, 118.1, 123.4, 127.6, 128.5, 129.8, 132.8, 133.5, 147.4, 165.9, 175.7. HRMS [ESI$^+$]: calculated for C$_{26}$H$_{32}$N$_4$O$_4$, 465.2502[M+H]$^+$, found 465.2501.

(4) (6-([1,4'-Bipiperidin]-1'-yl)-3-methylpyrrolo[2,1-α]phthalazine-1,2-diyl)dimethanol (BO-2590)

A solution of dimethyl-6-([1,4'-bipiperidin]-1'-yl)-3-methylpyrrolo[2,1-a]-phthalazine-1,2-dicarboxylate (0.65 g, 1.31 mmol) in DCM (50 mL) was added dropwise to a stirred suspension of LAH (0.10 g, 4.5 mmol) in diethyl ether (50 mL) at 0-5° C. After completion of the reaction in 2 h, the excess of LAH was decomposed by the addition of water (2 mL) and NH$_4$OH (2 mL). The reaction mixture was filtered through a pad of Celite and washed well with DCM. The combined filtrate and washings were evaporated in vacuo to dryness. The residue was recrystallized from ethanol to give (6-([1,4'-bipiperidin]-1'-yl)-3-methylpyrrolo-[2,1-α]phthalazine-1,2-diyl)dimethanol. Yield 0.42 g, (78%), mp 183-185° C.

$^1$H NMR (DMSO-d6) δ 1.41 (2H, s, CH$_2$), 1.52 (4H, s, 2×CH$_2$), 1.76-1.88 (4H, m, 2×CH$_2$), 2.43 (3H, s, CH$_3$), 2.50-2.53 (4H, m, 2×CH$_2$), 2.83 (2H, t, J=12.0 Hz, CH$_2$), 3.33 (1H, m, CH), 3.63 (2H, d, J=15.0 Hz, CH$_2$), 4.55 (3H, s, 1×OH and 1×OCH$_2$), 4.74 (1H, s, OH), 4.80 (2H, s, OCH$_2$), 7.43 (1H, t, J=7.2 Hz, ArH), 7.71 (1H, t, J=7.2 Hz, ArH), 7.89 (1H, d, J=8.4 Hz, ArH), 8.26 (1H, d, J=8.4 Hz, ArH).

$^{13}$C NMR (DMSO-d$_6$) δ 13.5, 16.5, 24.4, 25.9, 27.2, 49.6, 50.8, 53.0, 53.8, 61.7, 66.8, 113.6, 115.6, 117.5, 120.2, 123.0, 124.7, 125.4, 128.1, 129.6, 131.5, 153.8. HRMS [ESI$^+$]: calculated for C$_{24}$H$_{32}$N$_4$O$_2$, 409.2604[M+H]$^+$, found 409.2638.

1.4 (3-Ethyl-6-morpholinopyrrolo[2,1-a]phthalazine-1,2-diyl)-dimethanol (BO-2577)

(1) 4-(Phthalazin-1-yl)morpholine

To a solution of 11 (3.64 g, 20.0 mmol) in ethanol (120 mL) containing triethylamine (6.96 mL, 50.0 mmol) was added dropwise morpholine (1.89 mL, 22.0 mmol). The reaction mixture was heated at reflux for 18 h and the solvent was removed under reduced pressure to dryness. The reaction was cooled to rt and solvent was evaporated. The crude obtained was diluted with water and was extracted with DCM twice. The separated organic layer was dried over sodium sulfate and evaporated under vacuo to give 4-(phthalazin-1-yl)morpholine. Brown solid; Yield 3.8 g (80%); mp 125-127° C. (lit.$^{43}$ mp 82° C.).

$^1$H NMR (DMSO-d$_6$) δ 3.40 (4H, t, J=4.8 Hz, 2×CH$_2$), 3.88 (4H, t, J=4.4 Hz, 2×CH$_2$), 7.94-7.97 (2H, m, ArH), 8.09-8.14 (2H, m, ArH), 9.31 (1H, s, ArH).

$^{13}$C NMR (DMSO-d$_6$) δ 51.4, 51.7, 66.5, 120.7, 124.4, 124.5, 127.5, 128.5, 132.4, 132.5, 148.4, 159.7. HRMS [ESI$^+$]: calculated for C$_{12}$H$_{13}$N$_3$O, 216.1137[M+H]$^+$, found 216.1094.

(2) 4-Morpholino-2-propionyl-1,2-dihydrophthalazine-1-carbonitrile

To a solution of 4-(phthalazin-1-yl)morpholine (2.0 g, 9.3 mmol) in DCM (30 mL) containing catalytic amount of AlCl3 was added dropwise Me3SiCN (2.32 mL, 18.6 mmol). Propionyl chloride (1.2 mL, 14.0 mmol) was then added dropwise to the above mixture and stirred for 4 hr at room temperature. The reaction mixture was poured into ice-water and the organic layer was washed successively with water, 5% NaOH solution and water. The solution was dried over sodium sulfate and concentrated in vacuo to give 4-morpholino-2-propionyl-1,2-dihydrophthalazine-1-carbonitrile. Yield 2.46 g (89%); mp 146-148° C.

$^1$H NMR (DMSO-d6) δ 1.05 (3H, t, J=5.6 Hz, CH$_3$), 2.53-2.58 (1H, m, CH$_2$), 2.71-2.75 (1H, m, CH$_2$), 3.03 (2H, s, CH$_2$), 3.35 (2H, s, CH$_2$), 3.70 (2H, s, CH$_2$), 3.87 (2H, s, CH$_2$), 7.04 (1H, s, CH), 7.64 (3H, s, CH), 7.80 (1H, s, ArH).

$^{13}$C NMR (DMSO-d$_6$) δ 49.8, 51.8, 65.7, 116.4, 121.5, 124.0, 123.7, 129.2, 130.3, 132.8, 155.5, 169.6. HRMS [ESI$^+$]: calculated for C$_{16}$H$_{18}$N$_4$O$_2$, 299.1508[M+H]$^+$, found 299.1519.

(3) Dimethyl 3-ethyl-6-morpholinopyrrolo[2,1-α]phthalazine-1,2-dicarboxylate

To a solution of 4-morpholino-2-propionyl-1,2-dihydrophthalazine-1-carbonitrile (2.0 g, 7.0 mmol) in warm acetic acid (50 mL) was added dropwise HBF4 (1.30 mL). The mixture was allowed to stir at 50-60° C. for 30 min. After cooling to rt, the yellow solid salt was collected by filtration and the filter cake was washed with dry ether. The solid salt was dissolved in DMF (20 mL) and DMAD (1.5 mL, 12.0 mmol) was added slowly to this solution. The reaction mixture was heated at 90-100° C. for 16 h. The solvent was removed by evaporation in vacuo. The residue was crystallized from MeOH to give dimethyl-3-methyl-6-morpholinopyrrolo[2,1-a]-phthalazine-1,2-dicarboxylate. Yield 1.6 g (60%); mp 182-183° C.

$^1$H NMR (DMSO-d$_6$) δ 1.21 (3H, s, CH$_3$), 3.15 (2H, d, J=6.0 Hz, CH$_2$), 3.30 (4H, s, 2×CH$_2$), 3.80 (3H, s, COOCH$_3$), 3.89 (7H, s, 2×CH$_2$ and 1×COOCH$_3$), 7.63 (1H, s, ArH), 7.80 (1H, s, ArH), 8.06 (1H, d, J=7.0 Hz, ArH), 8.26 (1H, d, J=7.0 Hz, ArH).

$^{13}$C NMR (DMSO-d$_6$) δ 13.9, 23.0, 52.4, 52.7, 55.6, 66.2, 106.7, 115.8, 117.7, 121.0, 124.6, 126.7, 128.9, 130.3, 133.0, 156.2, 159.7, 165.6, 165.9. HRMS [ESI$^+$]: calculated for C$_{21}$H$_{23}$N$_3$O$_5$, 420.1535[M+Na]$^+$, found 420.1552.

(4) (3-Ethyl-6-morpholinopyrrolo[2,1-]phthalazine-1,2-diyl)dimethanol (BO-2577)

A solution of dimethyl 3-ethyl-6-morpholinopyrrolo[2,1-a]-phthalazine-1,2-dicarboxylate (1.4 g, 3.5 mmol) in DCM (50 mL) was added dropwise to a stirred suspension of LAH (0.43 g, 10.5 mmol) in diethyl ether (20 mL) at 0-5° C. After completion of the reaction in 2 h, the excess of LAH was decomposed by the addition of water (2 mL) and NH4OH (2 mL). The reaction mixture was filtered through a pad of Celite and washed well with DCM. The combined filtrate and washings were evaporated in vacuo to dryness. The residue was recrystallized from ethanol to give (3-ethyl-6-morpholinopyrrolo-[2,1-α]phthalazine-1,2-diyl)dimethanol (BO-2577). Yield 1.2 g (90%); mp 180-182° C.

$^1$H NMR (DMSO-d$_6$) δ 1.21 (3H, t, J=7.5 Hz, CH3), 2.93-2.98 (2H, m, CH2), 3.21 (4H, t, J=4.5 Hz, 2×CH$_2$), 3.86 (4H, t, J=4.5 Hz, 2×CH$_2$), 4.57 (3H, s, 1×OCH$_{2\ 1\ and}$ 1×OH), 4.76 (1H, t, J=5.5 Hz, OH), 4.82 (2H, d, J=5.0 Hz, OCH$_2$), 7.43 (1H, t, J=8.5 Hz, ArH), 7.72 (1H, t, J=8.0 Hz, ArH), 7.95 (1H, d, J=7.5 Hz, ArH), 8.29 (1H, d, J=8.0 Hz, ArH).

$^{13}$C NMR (DMSO-d6) δ 13.5, 16.5, 51.3, 53.1, 53.8, 65.8, 113.7, 115.2, 117.5, 120.4, 123.0, 124.7, 125.4, 128.3, 129.7, 131.7, 153.4. HRMS [ESI+]: calculated for C$_{19}$H$_{23}$N$_3$O$_3$, 364.1637[M+Na]+, found 364.1638.

Example 2 Chemical Synthesis of benzo[g]pyrrolo[2,1-α]phthalazine derivatives (Formula (I-B))
(Scheme 2)

Compounds of Formula (I-B) were synthesized as shown in Scheme 2. The commercially available 2,3-napthalene dicarboxylic acid anhydride 26 was treated with hydrazine hydrate in acetic acid to yield compound 27, which was reacted with phosphorus oxychloride to afford compound 28. Treatment of 28 with various ω-N,N-dialkylalkylamines, cyclic amines, anilines, 1-methylpiperazine, 1-ethylpiperazine, 1-methyl-4,4'-bipiperidine, or 1-ethyl-4,4'-bipiperidine and potassium carbonate in acetonitrile yielded compound 29, which was allowed to react with 10% Pd/C in methanol under H$_2$ atmosphere to give 30. Compound 30 was further reacted with trimethyl silylcyanide and alkyl or aryl chloride in dichloromethane to yield compounds 31. Similarly, compound 31 were converted into diester derivatives 32 by treating with tetrafluoro boric acid/ dimethyl acetylenedicarboxylate (DMAD) as described previously. The diester of 32 was reduced to the corresponding bis(hydroxymethyl) derivatives 33 (Formula I-B) by reacting with LiAlH$_4$ in a mixture of ether/CH$_2$Cl$_2$ in an ice bath. The bis(hydroxymethyl) derivatives 33 could then be converted into their corresponding bis(alkylcarbamates) congeners by treating with various isocyanate to give compound 34 (wherein R$^1$ is —CH$_2$OCONHR, R is alkyl or aryl), or treating with acid anhydride in pyridine to give compound 34 (wherein R$^1$ is —CH$_2$OCOR), or by reacting with toluene- or methane-sulfonyl chloride/Et$_3$N to give compound 34 (wherein R$^1$ is —CH$_2$OSO$_2$R, R is Me or 4-MePh), and other good leaving group.

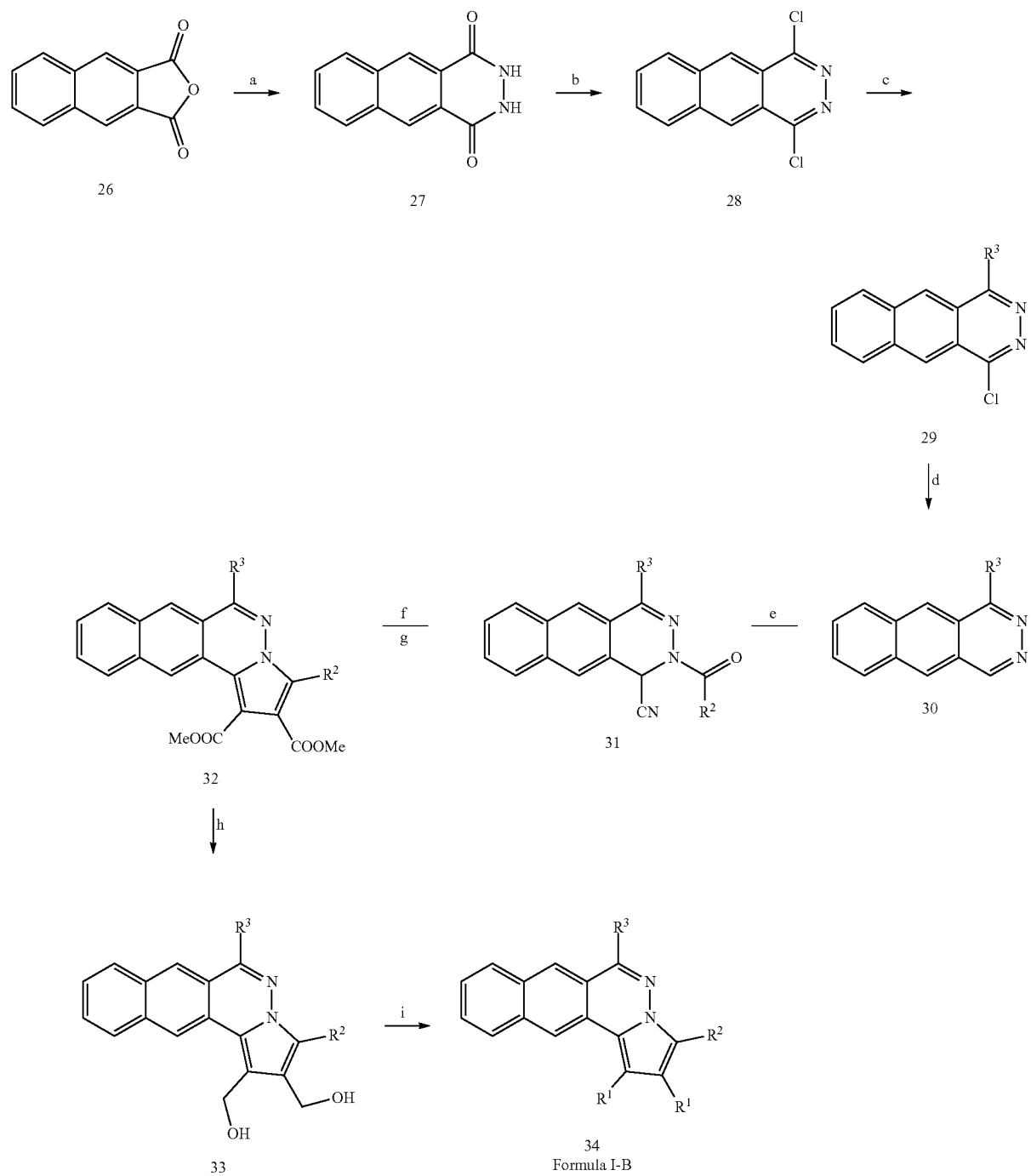

Scheme 2

Reagent and condition: a) Hydrazine hydrate/Acetic acid, 100° C.; b) POCl$_3$/Pyridine, reflux; c) R$^3$NH, K$_2$CO$_3$, ACN, reflux; d) Pd/C, Methanol, reflux; e) TMSCN, AlCl$_3$, R$^2$COCl, MDC, rt; f) HBF$_4$, AcOH, g) dimethyl acetylenedicarboxylate, DMF, 100° C.; h) LiAlH$_4$, Ether/MDC, 0-30° C.; i) RNCO, TEA, THF, reflux Exemplary compounds of formula (I-B) thus obtained included the following:

Formula I-B

| Compound No. | R³ | R² | R¹ | mp° C. |
|---|---|---|---|---|
| BO-2768 | dimethylamine | Me | —CH₂OH | 156-158 |
| BO-2762 | pyrrolidine | Me | —CH₂OH | 160-162 |
| BO-2755 | piperidine | Me | —CH₂OH | 173-175 |
| BO-2698 | morpholine | Me | —CH₂OH | 190-192 |
| BO-2792 | 1,4'-bipiperidine | Me | —CH₂OH | 181-183 |
| BO-2772 | dimethylamine | Me | —CH₂OCONHEt | 132-134 |
| BO-2763 | pyrrolidine | Me | —CH₂OCONHEt | 142-144 |
| BO-2757 | piperidine | Me | —CH₂OCONHEt | 160-162 |
| BO-2756 | morpholine | Me | —CH₂OCONHEt | 178-180 |
| BO-2793 | 1,4'-bipiperidine | Me | —CH₂OCONHEt | 169-171 |

2.1 (6-(dimethylamino)-3-methylbenzo[g]pyrrolo[2,1-α]phthalazine-1,2-diyl)dimethanol (BO-2768) and (6-(dimethylamino)-3-methylbenzoigl- prolog[2,1-α]phthalazine-1,2-diyl)-bis(methylene) bis(ethylcarbamate) (BO-2772)

(1) 2,3-Dihydrobenzo[g]phthalazine-1,4-dione

Hydrazine hydrate (80% solution, 63 mL) was added into a stirred suspension of the naphthalene-2,3-dicarboxylicacid anhydride (39.7 g, 200.0 mmol) in glacial acetic acid (600 mL). The mixture was heated at reflux for 6 h with stirring. After cooling, the solid product was collected by filtration, washed with water and dried to give 2,3-dihydrobenzo[g] phthalazine-1,4-dione. Yield: 40.2 g (94%); mp 344-346 (lit.⁴⁰ mp 344° C.

¹1-INMR (DMSO-d₆): δ 7.75-7.78 (2H, m, ArH), 8.29-8.31 (2H, m, ArH), 8.76 (2H, s, ArH), 11.52 (2H, s, 2×NH).

¹³C NMR (DMSO-d₆): δ 123.8, 126.2, 128.5, 129.1, 134.1. HRMS [ESI⁺]: calcd for $C_{12}H_8N_2O_2$, 213.0664[M+H]⁺, found 213.0681.

(2) 1, 4-Dichlorobenzo[g]phthalazine.

A suspension of 2,3-dihydrobenzo[g]phthalazine-1,4-dione (40.0 g, 188.0 mmol) in phosphorus oxychloride (400 mL) containing pyridine (24.0 mL) was heated at 100° C. for 5 h. The reaction mixture was allowed to cool to 40° C. and then concentrated under reduced pressure to dryness. The solid residue was triturated with ether, filtered, and washed with ether. The solid product was triturated and stirred with ice-water for 30 min and the solid product was collected by filtration, washed with water and dried to give 1,4-dichlorobenzo[g]phthalazine. Yield 40.8 g (85%); mp 217-219° C. mp 217-220° C.).

¹1-INMR (DMSO-d₆): δ 7.91-7.93 (2H, m, ArH), 8.50-8.52 (2H, m, ArH), 9.09 (2H, s, ArH).

¹³C NMR (DMSO-d₆) δ 124.3, 124.6, 126.2, 126.9, 128.0, 130.1, 137.4, 155.5. HRMS [ESI⁺]: calcd for $C_{12}H_6C_{12}N_2$, 248.9986[M+H]⁺, found 249.0000.

(3) 4-Chloro-N,N-dimethylbenzo[g]phthalazin-1-amine

Dimethylamine (30 mL, 60.0 mmol) was added slowly to a stirred suspension of 1,4-dichlorobenzo[g]phthalazine (10 g, 40.0 mmol) and anhydrous potassium carbonate (55 g, 400.0 mmol) in anhydrous acetonitrile (400 mL) at rt. The reaction mixture was allowed to stir for 72 h at rt and then filtered to remove potassium carbonate. The filtrate was evaporated under reduced pressure and the solid residue recrystallized from ether to give 4-chloro-N,N-dimethylbenzo[g]phthalazin-1-amine. Yield 9.3 g (90%); mp 90-92° C.

¹1-INMR (DMSO-d₆) δ 3.25 (6H, s, 2×NCH₃), 7.79-7.83 (2H, m, ArH), 8.37-8.40 (2H, m, ArH), 8.84 (1H, s, ArH), 8.93 (1H, s, ArH).

¹³C NMR (DMSO-d₆) δ 42.5, 118.9, 123.2, 125.0, 126.6, 128.6, 128.9, 129.0, 129.3, 133.9, 134.0, 147.8, 159.8. HRMS [ESI⁺]: calcd for $C_{14}H_{12}ClN_3$, 258.0798 [M+H³⁰], found 258.0791.

(4) N,N-Dimethylbenzo[g]phthalazin-1-amine

To a solution of 4-chloro-N,N-dimethylbenzo[g]phthalazin-1-amine (5.15 g, 20.0 mmol) in MeOH (200 mL) was added 10% Pd/C (1.03 g). The reaction mixture was hydrogenated at 35 psi for 4 h at rt and then filtered through pad of Celite. The filte cake was washed well with MeOH. The combined filtrate and washings were concentrated under reduced pressure and the residue was dissolved in DCM (200 mL) and washed with saturated aqueous NaHCO₃ solution, dried anhydrous sodium sulfate, and evaporated in vacuo to dryness. The product was purified by chromatography (SiO₂, elution gradient 0-40% ethyl acetate in hexane) to give N,N-dimethylbenzo[g]phthalazin-1-amine. Yield 2.8 g (64%); mp 115-117° C.

¹1-1 NMR (DMSO-d₆) δ 3.23 (6H, s, 2×NCH₃), 7.72-7.76 (2H, m, ArH), 8.24 (1H, dd, J=6.8 and 2.2 Hz, ArH), 8.35 (1H, dd, J=6.8 and 2.2 Hz, ArH), 8.69 (1H, s, ArH), 8.85 (1H, s, ArH), 9.26 (1H, s, ArH).

¹³C NMR (DMSO-d₆) δ 42.4, 117.4, 125.1, 125.2, 126.3, 127.7, 128.2, 128.4, 129.4, 133.7, 133.8, 146.8, 159.0. HRMS [ESI⁺]: calcd for $C_{14}H_{13}N_3$, 224.1188[M+H⁺], found 224.1198.

(5) 2-Acetyl-4-(dimethylamino)-1,2-dihydrobenzo[g]phthalazine-1-carbonitrile

To a solution of N,N-dimethylbenzo[g]phthalazin-1-amine (2.22 g, 10.0 mmol) in DCM (30 mL) containing catalytic amount of AlCl₃ was added dropwise Me₃SiCN (2.5 mL, 20.0 mmol). Acetyl chloride (1.1 mL, 15.0 mmol) was then added dropwise to the above mixture and stirred for 4 h at rt. The reaction mixture was poured into ice-water and the organic layer was washed successfully with water, 5% NaOH solution and water. The solution was drid over sodium sulfate and concentrated in vacuo to give 2-acetyl-4-(dimethylamino)-1,2-dihydrobenzo[g]phthalazine-1-carbonitrile. Yield 2.7 g (92%); mp 125-127° C.

¹H NMR (DMSO-d6) δ 2.29 (3H, s, COCH3), 2.99 (6H, s, 2×NCH₃), 7.23 (1H, s, CH), 7.67-7.73 (2H, m, ArH), 8.01 (1H, d, J=7.7 Hz, ArH), 8.20 (1H, d, J=7.6 Hz, ArH), 8.34 (1H, s, ArH), 8.35 (1H, s, ArH).

¹³C NMR (DMSO-d₆) δ 20.6, 40.9, 116.4, 118.2, 125.8, 126.3, 127.3, 127.7, 127.8, 128.8, 129.4, 132.8, 133.7, 155.7, 170.9. HRMS [ESI⁺]: calcd for $C_{17}H_{16}N_4O$, 293.1402[M+H]⁺, found 293.1407.

(6) Dimethyl 6-(dimethylamino)-3-methylbenzo[g]pyrrolo[2,1-α]phthalazine-1,2-dicarboxylate To a solution of 2-acetyl-4-(dimethylamino)-1,2-dihydrobenzo[g]phthalazine-1-carbonitrile (2.95 g, 10.0 mmol) in warm acetic acid (80 mL) was added dropwise HBF4 (2.2 mL, 12.0 mmol). The mixture was allowed to stir at 50-60°

C. for 30 min. After cooling to rt, the yellow solid salt was collected by filtration and the filter cake was washed with dry ether. The solid salt was dissolved in DMF (20 mL) and DMAD (3.1 mL, 25.0 mmol) was added slowly to this solution. The reaction mixture was heated at 90-100° C. for 16 h. The solvent was removed by evaporation in vacuo. The residue was crystallized from MeOH to give dimethyl 6-(dimethylamino)-3-methylbenzo[g]pyrrolo[2,1-α]phthalazine-1,2-dicarboxylate. Yield 1.7 g (43%); mp 180-182° C.

$^1$H NMR (DMSOd6) δ 2.66 (3H, s, CH$_3$), 3.08 (6H, s, 2×NCH$_3$), 3.81 (3H, s, COOCH3), 3.97 (3H, s, COOCH$_3$), 7.64 (1H, t, J=7.8 Hz, ArH), 7.71 (1H, t, J=7.2 Hz, ArH), 8.06 (1H, d, J=8.2 Hz, ArH), 8.24 (1H, d, J=8.3 Hz, ArH), 8.65 (1H, s, ArH), 8.73 (1H, s, ArH).

$^{13}$C NMR (DMSO-d$_6$) δ 10.2, 42.6, 51.6, 52.5, 107.9, 111.2, 115.6, 119.9, 121.0, 123.9, 127.0, 127.9, 128.0, 129.0, 129.4, 130.9, 131.3, 134.0, 156.8, 164.4, 166.9. HRMS [ESI$^+$]: calcd for C$_{22}$H$_{12}$N$_3$O$_4$, 392.1610[M+H]$^+$, found 392.1590.

(8) (6-(Dimethylamino)-3-methylbenzo[g]pyrrolo[2,1-α]phthalazine-1,2-diyl)dimethanol (BO-2768)

A solution of dimethyl 6-(dimethylamino)-3-methylbenzo[g]pyrrolo[2,1-α]-phthalazine-1,2-dicarboxylate (1.6 g, 4.0 mmol) in DCM (50 mL) was added dropwise to a stirred suspension of LAH (0.39 g, 10.0 mmol) in diethyl ether (100 mL) at 0-5° C. After completion of the reaction in 2 h, the excess of LAH was decomposed by the addition of water (2 mL) and NH$_4$OH (2 mL). The reaction mixture was filtered through a pad of Celite and washed well with DCM. The combined filtrate and washings were evaporated in vacuo to dryness. The residue was recrystallized from ethanol to give (6-(dimethylamino)-3-methylb enzo[g]-pyrrolo[2,1-α]phthalazine-1,2-diyl)dimethanol (BO-2768). Yield 1.1 g (80%); mp 156-158° C.

$^1$H NMR (DMSO-d6) δ 2.46 (3H, s, CH$_3$), 2.99 (6H, s, 2×NCH$_3$), 4.56 (2H, d, J=5.1 Hz, OCH$_2$), 4.62 (1H, t, J=5.4 Hz, OH), 4.90-4.91 (3H, m, OCH2 and OH), 7.52 (1H, t, J=7.5 Hz, ArH), 7.63 (1H, t, J=7.3 Hz, ArH), 8.00 (1H, d, J=8.3 Hz, ArH), 8.14 (1H, d, J=8.2 Hz, ArH), 8.58 (1H, s, ArH), 8.66 (1H, s, ArH).

$^{13}$C NMR (DMSO-d$_6$) δ 8.9, 42.8, 53.4, 54.2, 115.6, 115.7, 117.5, 120.4, 120.4, 123.6, 125.5, 126.3, 126.6, 127.5, 128.1, 129.3, 130.1, 134.6, 154.7. HRMS [ESI$^+$]: calcd for C$_{20}$H$_{21}$N$_3$O$_2$, 318.1606[M+H–H$_2$O]$^+$, found 318.1620.

(8) (6-(Dimethylamino)-3-methylbenzo[g]pyrrolo[2,1-α]phthalazine-1,2-diyl)-bis(methylene) bis(ethylcarbamate) (B0-2772).

A mixture of (6-(dimethylamino)-3-methylbenzo[g]pyrrolo[2,1-α]phthalazine-1,2-diyl)dimethanol (0.2 g, 0.6 mmol), (0.16 g, 0.5 mmol), ethyl isocyanate (0.2 mL, 2.4 mmol) and and TEA (0.55 mL, 4.0 mmol) in dry DMF was stirred for 24-48 h at rt under argon. After completion of the reaction, the reaction mixture was evaporated to dryness in vacuo. The residue was triturated with ether and the desired product was collected by filtration to give (6-(Dimethylamino)-3-methylbenzo[g]prolog- [2,1-a]phthalazine-1,2-diyl)-bis(methylene) bis(ethylcarbamate) (BO-2772). Yield 0.15 g (53%); mp 132-134° C.

$^1$H NMR (DMSO-d$_6$) δ 0.98-1.01 (6H, m, 2×CH$_3$), 2.48 (3H, s, CH$_3$), 2.98-3.04 (10H, m, 2×CH$_2$ and 2×NCH$_3$), 5.18 (2H, s, OCH$_2$), 5.49 (2H, s, OCH$_2$), 7.06 (1H, t, J=5.2 Hz, NH), 7.10 (1H, t, J=5.5 Hz, NH), 7.56 (1H, t, J=7.9 Hz, ArH), 7.66 (1H, t, J=7.4 Hz, ArH), 7.97 (1H, d, J=8.3 Hz, ArH), 8.17 (1H, d, J=8.3 Hz, ArH), 8.51 (1H, s, ArH), 8.64 (1H, s, ArH).

$^{13}$C NMR (DMSO-d$_6$). δ 8.9, 15.1, 15.2, 35.0, 35.1, 42.8, 56.2, 57.0, 110.6, 115.5, 116.2, 118.5, 120.3, 125.5, 125.6, 126.0, 127.0, 127.6, 128.4, 129.3, 130.3, 134.5, 155.3, 156.1, 156.3. HRMS [ESI$^+$]: calcd for C$_{26}$H$_{31}$N$_5$O$_4$, 302.1657[M+H–2(OCONHC$_2$H$_5$)]$^+$, found 302.1667.

2.2 (3-methyl-6-(pyrrolidin-1-yl)benzo[g]pyrrolo[2,1-α]- phthalazine-1,2-diyl)dimethanol (BO-2762) and (3-methyl-6-(pyrrolidin-1-yl)- benzo[g]pyrrolo [2,1-α]phthalazine-1,2-diyl)-bis(methylene) bis(ethylcarbamate) (BO-2763)

(1) 1-Chloro-4-(pyrrolidin-1-yl)benzo[g]phthalazine

Pyrrolidine (3.5 mL, 42.0 mmol) was added slowly to a stirred suspension of 1,4-dichlorobenzo[g]phthalazine (7.0 g, 28.0 mmol) and anhydrous potassium carbonate (55 g, 400.0 mmol) in anhydrous acetonitrile (400 mL). The reaction mixture was allowed to stir for 72 h at rt and then filtered to remove potassium carbonate. The filtrate was evaporated under reduced pressure and the solid residue recrystallized from ether to give 1-chloro-4-(pyrrolidin-1-yl)benzo[g]phthalazine. Yield 6.8 g (85%); mp 112-114° C.

$^1$H NMR (DMSO-d6) δ 2.02 (4H, brs, 2×CH$_2$), 3.96 (4H, brs, 2×CH$_2$), 7.76-7.79 (2H, m, ArH), 8.33-8.38 (2H, m, ArH), 8.75 (1H, s, ArH), 9.06 (1H, s, ArH).

$^{13}$C NMR (DMSO-d$_6$) δ 25.4, 51.1, 118.7, 123.1, 124.0, 126.8, 128.1, 128.6, 128.9, 129.5, 133.7, 144.6, 155.5. HRMS [ESI$^+$]: calcd for C$_{16}$H$_{14}$ClN$_{13}$, 284.0955 [M+H]$^+$, found 284.0948.

(2) 1-(Pyrrolidin-1-yl)benzo[g]phthalazine

To a solution of 1-chloro-4-(pyrrolidin-1-yl)benzo[g] phthalazine (5.1 g, 18.0 mmol) in MeOH (200 mL) was added 10% Pd/C (1.03 g). The reaction mixture was hydrogenated at 35 psi for 4 h at rt and then filtered through pad of Celite. The filte cake was washed well with MeOH. The combined filtrate and washings were concentrated under reduced pressure and the residue was dissolved in DCM (200 mL) and washed with saturated aqueous NaHCO$_3$ solution, dried anhydrous sodium sulfate, and evaporated in vacuo to dryness. The product was purified by chromatography (SiO$_2$, elution gradient 0-40% ethyl acetate in hexane) to give 1-(pyrrolidin-1-yl)benzo[g]phthalazine. Yield 3.3 g (73%); mp 150-152° C.

$^1$H NMR (DMSO-d6) δ 2.00-2.03 (4H, m, 2×CH$_2$), 3.94-3.97 (4H, m, 2×CH$_2$), 7.66-7.73 (2H, m, ArH), 8.18 (1H, d, J=8.2 Hz, ArH), 8.31 (1H, d, J=8.3 Hz, ArH), 8.55 (1H, s, ArH), 8.97 (1H, s, ArH), 9.04 (1H, s, ArH).

$^{13}$C NMR (DMSO-d$_6$) δ 25.5, 50.8, 117.2, 125.3, 125.4, 127.2, 128.0, 128.1, 129.6, 133.5, 144.1, 154.8. HRMS [ESI$^+$]: calcd for C$_{16}$H$_{15}$N$_3$, 250.1344[M+H]$^+$, found 250.1362.

(3) 2-Acetyl-4-(pyrrolidin-1-yl)-1,2-dihydrobenzo[g] phthalazine-1-carbonitrile

To a solution of 1-(pyrrolidin-1-yl)benzo[g]phthalazine (3.25 g, 13.0 mmol) in DCM (50 mL) containing catalytic amount of AlCl$_3$ was added dropwise Me$_3$SiCN (3.26 mL, 26.0 mmol). Acetyl chloride (1.4 mL, 19.6 mmol) was then added dropwise to the above mixture and stirred for 4 hrs at room temperature. The reaction mixture was poured into ice-water and the organic layer was washed successfully with water, 5% NaOH solution and water. The solution was drid over sodium sulfate and concentrated in vacuo to give 2-acetyl-4-(pyrrolidin-1-yl)-1,2-dihydrobenzo[g]phthalazine-1-carbonitrile (33b) (BO-2760). Yield 3.2 g (77%); mp 162-164° C.

$^1$H NMR (CDCl$_3$) δ 1.92-2.00 (2H, m, CH$_2$), 2.08-2.10 (2H, m, CH$_2$), 2.31 (3H, s, COCH$_3$), 3.44-3.47 (2H, m, $CH_2$), 3.83-3.89 (2H, m, $CH_2$), 6.90 (1H, s, CH), 7.58-7.64 (2H, m, ArH), 7.85 (1H, s, ArH), 7.90 (1H, d, J=7.9 Hz, ArH), 7.93 (1H, d, J=7.9 Hz, ArH), 8.17 (1H, s, ArH).

$^{13}$C NMR (CDCl$_3$) δ 20.7, 15.4, 41.5, 50.1, 115.8, 120.1, 125.7, 126.3, 127.0, 127.7, 127.9, 128.5, 129.0, 133.1, 133.8, 154.1. 171.1. HRMS [ESI$^+$]: calcd for $C_{19}H_{18}N_4O$, 319.1559[M+H]$^+$, found 319.1557.

(4) Dimethyl 3-methyl-6-(pyrrolidin-1-yl)benzo[g]pyrrolo[2,1-α]phthalazine-1,2-dicarboxylate To a solution of 2-acetyl-4-(pyrrolidin-1-yl)-1,2-dihydrobenzo[g]phthalazine-1-carbonitrile (3.2 g, 10.0 mmol) in warm acetic acid (90 mL) was added dropwise HBF4 (2.2 mL, 12.0 mmol). The mixture was allowed to stir at 50-60° C. for 30 min. After cooling to rt, the yellow solid salt was collected by filtration and the filter cake was washed with dry ether. The solid salt was dissolved in DMF (20 mL) and DMAD (3.1 mL, 25.0 mmol) was added slowly to this solution. The reaction mixture was heated at 90-100° C. for 16 h. The solvent was removed by evaporation in vacuo. The residue was crystallized from MeOH to give dimethyl 3-methyl-6-(pyrrolidin-1-yl)benzo[g]pyrrolo[2,1-α]phthalazine-1,2-dicarboxylate. Yield 2.0 g (48%); mp 190-192 °C.

$^1$H NMR (CDCl$_3$) δ 2.02-2.05 (4H, m, 2×$CH_2$), 2.68 (3H, s, $CH_3$), 3.76-3.78 (4H, m, 2×$CH_2$), 3.89 (3H, s, COOCH$_3$), 4.04 (3H, s, COOCH$_3$), 7.49 (1H, t, J=7.1 Hz, ArH), 7.57 (1H, t, J=6.9 Hz, ArH), 7.90 (1H, d, J=8.5 Hz, ArH), 7.92 (1H, d, J=8.4 Hz, ArH), 8.52 (1H, s, ArH), 8.77 (1H, s, ArH).

$^{13}$C NMR (CDCl$_3$) δ 10.4, 25.6, 51.4, 51.5, 52.4, 107.6, 111.2, 117.1, 120.7, 121.9, 124.8, 126.3, 127.1, 128.1, 128.1, 128.8, 131.2, 131.4, 134.3, 153.8, 165.6, 168.1. HRMS [ESI$^+$]: calcd for $C_{24}H_{23}N_3O_4$, 440.1586[M+Na]$^+$, found 440.1569.

(5) (3-Methyl-6-(pyrrolidin-1-yl)benzo[g]pyrrolo[2,1-α] phthalazine-1,2-diyl)dimethanol (BO-2762)

A solution of dimethyl 3-methyl-6-(pyrrolidin-1-yl)benzo[g] pyrrolo[2,1-a]-phthalazine-1,2-dicarboxylate (1.7 g, 4.0 mmol) in DCM (50 mL) was added dropwise to a stirred suspension of LAH (0.39 g, 10.0 mmol) in diethyl ether (100 mL) at 0-5° C. After completion of the reaction in 2 h, the excess of LAH was decomposed by the addition of water (2 mL) and NH$_4$OH (2 mL). The reaction mixture was filtered through a pad of Celite and washed well with DCM. The combined filtrate and washings were evaporated in vacuo to dryness. The residue was recrystallized from ethanol to give (3-methyl-6-(pyrrolidin-1-yl)benzo [g]prolog-[2, 1-a]phthalazine-1,2-diyl)dimethanol (BO-2762). Yield 1.1 g (82%); mp 160-162° C.

$^1$H NMR (DMSO-d6) δ 1.98-1.99 (4H, m, 2×$CH_2$), 2.43 (3H, s, $CH_3$), 3.68-3.70 (4H, m, 2×$CH_2$), 4.52-4.55 (3H, m, $OCH_2$ and OH), 4.82 (1H, t, J=5.0 Hz, OH), 4.90 (2H, d, J=5.1 Hz, $OCH_2$), 7.50 (1H, t, J=7.4 Hz, ArH), 7.61 (1H, t, J=7.3 Hz, ArH), 7.98 (1H, d, J=8.3 Hz, ArH), 8.14 (1H, d, J=8.3 Hz, ArH), 8.64 (1H, s, ArH), 8.67 (1H, s, ArH).

$^{13}$C NMR (DMSO-d$_6$) δ 8.9, 25.0, 50.9, 53.4, 54.2, 115.2, 116.4, 117.2, 119.9, 120.0, 123.0, 125.3, 126.4, 126.7, 127.3, 128.1, 129.3, 129.9, 134.3, 152.2. HRMS [ESI$^+$]: calcd for $C_{22}H_{23}N_3$; $O_2$, 344.1763[M+H–$H_2O$]$^+$, found 344.1754.

(6) (3-Methyl-6-(pyrrolidin-1-yl)benzo[g]pyrrolo[2,1-α] phthalazine-1,2-diyl)-bis(methylene) bis(ethylcarbamate) (BO-2763)

A mixture of (3-methyl-6-(pyrrolidin-1-yl)benzo[g]pyrrolo[2,1-a]phthalazine-1,2-diyl)dimethanol (0.36 g, 1.0 mmol), ethyl isocyanate (0.32 mL, 4.0 mmol) and TEA (0.55 mL, 4.0 mmol) in dry DMF was stirred for 24-48 hrs at room temperature under argon. After completion of the reaction, the reaction mixture was evaporated to dryness in vacuo. The residue was triturated with ether and the desired product was collected by filtration to give (3-methyl-6-(pyrrolidin-1-yl)benzo- [g]pyrrolo[2,1-a]phthalazine-1,2-diyl)-bis(methylene) bis(ethylcarbamate) (BO-2763). Yield 0.28 g (56%); mp 142-144° C.

$^1$H NMR (DMSO-d6) δ 0.95-1.02 (6H, m, 2×$CH_3$), 1.98 (4H, brs, 2×$CH_2$), 2.45 (3H, s, CH3), 2.97-3.05 (4H, m, 2×$CH_2$), 3.72 (4H, brs, 2×$CH_2$), 5.16 (2H, s, $OCH_2$), 5.48 (2H, s, $OCH_2$), 7.02 (1H, t, J=5.7 Hz, NH), 7.07 (1H, t, J=5.2 Hz, NH), 7.54 (1H, t, J=7.7 Hz, ArH), 7.65 (1H, t, J=7.4 Hz, ArH), 7.94 (1H, d, J=8.1 Hz, ArH), 8.17 (1H, d, J=8.3 Hz, ArH), 8.47 (1H, s, ArH), 8.72 (1H, s, ArH).

$^{13}$C NMR (DMSO-d$_6$) δ 8.9, 15.1, 15.2, 25.1, 35.0, 35.1, 51.0, 56.2, 57.1, 110.0, 115.7, 116.3, 118.2, 119.8, 124.8, 125.7, 127.1, 127.3, 128.3, 129.3, 130.1, 134.2, 152.6, 156.1, 156.3. HRMS [ESI$^+$]: calcd for $C_{28}H_{33}N_5O_4$, 328.1814[M+H–2(OCONHC$_2$H$_5$)]$^+$, found 328.1816.

Example 3 Preparation of Liposomal Encapsulation of the Compound of Formula (I)

The compounds of formula (I) are generally hydrophobic. To deliver the active compound in high drug concentrations and to the target of specific tumor cells or organs, the compounds of formula (I), particularly, BO-2590, was encapsulated in liposomes to generate liposomal drug by a modified dehydration-rehydration method and repeated extrusion in accordance with procedures described below.

(1) Liposomal encapsulation

The liposomal encapsulation of BO-2590 was prepared by mixing Soybean phosphatidylcholine (SPC), 1,2-distearoyl-sn-glycero-3-phosphocholine (DSPC), cholesterol (CHO) and PEG-2000 (a molar ratio of 50:45:4:1) in the CHCl$_3$. The mixture was placed in a round-bottomed flask, and BO-2590 was then added into the reaction mixture (4 mg/mL). The organic solvent was removed by rotary evaporation under reduced pressure. The resulting dry lipid film was hydrated in phosphate-buffered saline (137 mM NaCl, 2.7 mM KCl, 10 mM Na$_2$HPO$_4$ and 1.8 mM KH$_2$PO$_4$) and dispersed by hand shaking. The suspension was frozen and thawed several times, followed by repeated extrusion through polycarbonate membrane filters (Costar, Cambridge, Mass.) of 0.8, 0.6, 0.4, 0.2μm pore size using high-pressure extrusion equipment (Lipex Biomembranes, Vancouver, Canada) at 60° C. The product solution was stored at 4° C.

(2) HPLC Analysis

The liposomal BO-2590 (BO-2590L) was quantified by high pressure liquid chromatography (Agilent Technologies) with RP-18 column under mobile phase condition [Acetonitrile/MeOH/$H_2O$ (0.5%TFA) (45/50/5), (Retention time 4.6 min, Flow rate 0.5mL/min)]. The liposomal BO-2590 (100 ul) was added the mobile phase (100 ul), mixed completely with vortex, and incubated 10 min. The resulting milky sample was centrifuge, and the clear supernatant was taken into HPLC quantified analysis. In our preparations (n>5), BO-2590 liposomes contained 3.12 to 2.94 mg/mL (encapsulation 76 to 70% with starting material at the concentration of 4 mg/mL).

(3) Stability Analysis

The liposomal encapsulated BO-2590L was stored at 4° C. for three weeks. It exhibited about 10% decay from the encapsulation 76% to 66.3% by HPLC analysis.

Example 4 In Vitro Characterization of the Compounds of Formula (I)

4.1 Compound of formula (I) possessed cytotoxicity toward cancer cells

All representative compounds of Formulae (I-A) and (I-B) were first evaluated for their in vitro cytotoxicity to human lymphoblastic leukemia cell line (CCRF-CEM) and its vinblastine-resistant sub-cell line (CCRF-CEM/VBL) (see Table 1). The selected compounds with significant cytotoxic were further evaluated to a panel of solid tumor cell lines, i.e., colon cancer HCT-116, non-small cell lung cancer H460, small cell lung cancer H526, and pancreatic cancer PacaS1 (Table 2).

Briefly, the tested cells were cultured at an initial density $3\times10^3$ cells per milliliter in a 5% $CO_2$-humidified atmosphere at 37° C. in RPMI medium 1640 (GIBCO/BRL) containing penicillin (100 units/mL), streptomycin (100μg/mL, GIBCO/BRL), and 5% heat-inactivated FBS. After a 72-hr incubation in various concentrations of the newly synthesized compounds, the cytotoxic effects of them to all cell lines were determined by the PrestoBlue®(Invitrogen) assay using a microplate spectrophotometer. Briefly, at the end of treatment, an aliquot of PrestoBlue® solution was added and then cells were incubated at 37° C. for 1-2 hr. The absorbance at 570 and 600 nm was measured with a microplate reader. Dose-effect relationship at 6 or 7 concentrations of each compound was used to calculate ICso values by aid of median-effect principle (CompuSyn software, version 1.0.1; CompuSyn, Inc., Paramus, N.J.) developed by Chou and Martin (Pharmacol Rev 2006, 58:621-681). The ICso is defined by the concentration required to inhibit tumor cell growth by 50%. Data represent the mean±STDEV of three to six independent experiments for each compound.

Table 1 summarized the in vitro cytotoxicity of 1,2-bis (hydroxymethyl)pyrrolo[2,1-a] phthal azine derivatives (Formula I-A) and benzo[g]pyrrolo[2,1-a]phthalazine derivatives (Formula I-B) to human lymphoblastic leukemia CCRF-CEM and its vinblastine resistant subline CCRF-CEM/VBL. The data revealed that these compounds exhibited significant cytotoxicity against CCRF-CEM and no cross-resistance to vinblastine. The selected compounds were evaluated their cytotoxicity against various types of solid tumors (i.e., colon cancer HCT-116, non-small cell lung cancer H460, small cell lung cancer H526, and pancreatic cancer PacaS1). Notably, the tested compounds were generally actively inhibited the cell growth of all solid tumor cell lines (Table 2). Among them, small cell lung cancer H526 cells were the most susceptible to the tested compounds.

Further, the cytotoxicity of the compound of Formula (I-B) with that of a known anti-proliferation agent (e.g., irinotecan, etoposide, cisplatin and carboplatin) in human small cell lung cancer cells (SCLC) was compared, and results are summarized in Table 3. As the data in Table 3 indicated, the compound of Formula (I-B) of the present disclosure, in general, was more potent than that of irinotecan, etoposide, cisplatin and carboplatin.

TABLE 1

The cytotoxicity of compounds of Formulae (I-A) and (I-B) to human lymphoblastic leukemia (CCRF) and its vinblastine resistant sub-cell line CCRF-CEM/VBL.

| Compounds | Formula | CCRF-CEM $IC_{50}$ (μM)[a] | CEM/VBL[b] |
|---|---|---|---|
| BO-2571 | Formula I-A | 0.76 ± 0.03 | 0.56 ± 0.06 [0.74×][c] |
| BO-2577 | Formula I-A | 3.04 ± 0.38 | 2.55 ± 0.12 [0.84×] |
| BO-2629 | Formula I-A | 6.63 ± 1.74 | 5.75 ± 0.62 [0.86×] |
| BO-2573 | Formula I-A | 0.69 ± 0.22 | 0.45 ± 0.03 [0.65×] |
| BO-2625 | Formula I-A | 3.44 ± 0.82 | 5.11 ± 0.91 [1.48×] |
| BO-2630 | Formula I-A | 6.12 ± 0.88 | 7.21 ± 0.25 [1.18×] |
| BO-2574 | Formula I-A | 1.17 ± 0.18 | 0.96 ± 0.16 [0.82×] |
| BO-2626 | Formula I-A | 3.68 ± 0.25 | 1.58 ± 0.20 [0.43×] |
| BO-2631 | Formula I-A | 2.85 ± 1.52 | 3.07 ± 0.43 [1.07×] |
| BO-2785 | Formula I-A | 3.33 ± 0.39 | 2.94 ± 0.26 [0.88×] |
| BO-2686 | Formula I-A | 0.92 ± 0.07 | 0.47 ± 0.05 [0.51×] |
| BO-2720 | Formula I-A | 1.04 ± 0.12 | 1.33 ± 0.13 [1.28×] |
| BO-2590 | Formula I-A | 0.23 ± 0.03 | 0.25 ± 0.04 [1.09×] |
| BO-2786 | Formula I-A | 0.73 ± 0.05 | 0.55 ± 0.06 [0.75×] |
| BO-2716 | Formula I-A | 1.42 ± 0.09 | 2.10 ± 0.09 [1.47×] |
| BO-2721 | Formula I-A | 1.28 ± 0.09 | 1.23 ± 0.20 [0.96×] |
| BO-2787 | Formula I-A | 1.54 ± 0.22 | 0.97 ± 0.17 [0.63×] |
| BO-2717 | Formula I-A | 4.11 ± 0.15 | 3.16 ± 0.18 [0.77×] |
| BO-2722 | Formula I-A | 1.92 ± 0.11 | 1.73 ± 0.09 [0.90×] |
| BO-2768 | Formula I-B | 0.19 ± 0.01 | 0.10 ± 0.01 [0.53×] |
| BO-2762 | Formula I-B | 0.19 ± 0.01 | 0.14 ± 0.02 [0.74×] |
| BO-2755 | Formula I-B | 0.80 ± 0.09 | 1.01 ± 0.11 [1.26×] |
| BO-2698 | Formula I-B | 0.38 ± 0.05 | 0.33 ± 0.03 [0.86×] |
| BO-2792 | Formula I-B | 0.017 ± 0.009 | 0.025 ± 0.005 [1.51×] |
| BO-2772 | Formula I-B | 0.138 ± 0.008 | 0.099 ± 0.006 [0.71×] |
| BO-2763 | Formula I-B | 0.42 ± 0.07 | 0.25 ± 0.06 [0.59×] |
| BO-2757 | Formula I-B | 0.95 ± 0.05 | 1.20 ± 0.14 [1.26×] |
| BO-2756 | Formula I-B | 0.31 ± 0.02 | 0.32 ± 0.04 [1.03×] |
| BO-2793 | Formula I-B | 0.057 ± 0.004 | 0.104 ± 0.028 [1.82×] |
| Cisplatin | | 16.53 ± 0.90 | 8.88 ± 1.86 [0.54×] |
| Vinblastine[d] | | 1.41 ± 0.10 | 392.48 ± 44.75 [278.3×] |

[a]Data represent the mean ± STDEV of three to six independent experiments for each compound.
[b]CCRF-CEM/VBL is a sub-cell line of CCRF-CEM.
[c]Numbers in brackets are resistance factors determined by comparison with the corresponding $IC_{50}$ of the parent cell line.
[d]$IC_{50}$ values in nM.

TABLE 2

In vitro cytotoxicity of 1,2-bis(hydroxymethyl)pyrrolo[2,1-a]phthalazine derivatives (Formula (I-A)) and benzo[g]pyrrolo[2,1-a]phthalazine derivatives (Formula (I-B)) to human solid tumor cell lines.

| Compounds/ | $IC_{50}$ (µM) | | | |
|---|---|---|---|---|
| Formula | HCT-116 | H460 | H526 | Paca SI |
| BO-2571 (I-A) | 1.67 ± 0.18 | 2.64 ± 0.52 | 0.10 ± 0.01 | 2.16 ± 0.09 |
| BO-2577 (I-A) | 11.53 ± 1.66 | 18.57 ± 0.18 | 0.75 ± 0.12 | 13.02 ± 0.93 |
| BO-2629 (I-A) | 5.20 ± 0.43 | 18.72 ± 1.81 | 1.95 ± 0.26 | 36.63 ± 1.04 |
| BO-2573 (I-A) | 1.70 ± 0.21 | 2.48 ± 0.73 | 0.21 ± 0.03 | 17.23 ± 3.48 |
| BO-2686 (I-A) | 3.96 ± 0.06 | 3.87 ± 0.73 | 0.30 ± 0.04 | 11.73 ± 1.16 |
| BO-2590 (I-A) | 0.40 ± 0.09 | 0.60 ± 0.11 | 0.014 ± 0.004 | 0.30 ± 0.08 |
| BO-2786 (I-A) | 2.45 ± 0.65 | 3.47 ± 0.47 | 0.57 ± 0.09 | 8.01 ± 1.40 |
| BO-2768 (I-B) | 0.65 ± 0.02 | 1.02 ± 0.16 | 0.05 ± 0.001 | 3.98 ± 1.04 |
| BO-2762 (I-B) | 0.93 ± 0.12 | 0.78 ± 0.24 | 0.05 ± 0.01 | 1.04 ± 0.08 |
| BO-2755 (I-B) | 4.13 ± 0.27 | 3.03 ± 0.48 | 0.12 ± 0.04 | 10.01 ± 1.64 |
| BO-2698 (I-B) | 1.13 ± 0.02 | 1.18 ± 0.10 | 0.04 ± 0.01 | 0.88 ± 0.26 |
| Cisplatin | 9.17 ± 0.67 | 5.11 ± 0.22 | 0.73 ± 0.07 | 27.04 ± 0.98 |

TABLE 3

Compared cytotoxicity of compounds of Formula I-B with therapeutic agents to a batch of human small cell lung cancer (SCLC) cells.

| Compounds | $IC_{50}$ (µM) | | | | |
|---|---|---|---|---|---|
| | H211 | H82 | H526 | H146 | H1417 |
| BO-2762 | 0.2 ± 0.12 | 0.41 ± 0.15 | 0.03 ± 0.01 | 1.01 ± 0.24 | 0.60 ± 0.34 |
| BO-2698 | 0.22 ± 0.07 | 0.40 ± 0.16 | 0.09 ± 0.06 | 1.02 ± 0.16 | 0.37 ± 0.01 |
| BO-2792 | 0.02 ± 0.02 | 0.04 ± 0.01 | 0.003 ± 0.003 | 0.20 ± 0.15 | 0.25 ± 0.05 |
| BO-2768 | 0.17 ± 0.07 | 0.31 ± 0.14 | 0.04 ± 0.005 | 1.17 ± 0.29 | 0.42 ± 0.19 |
| BO-2755 | 0.80 ± 0.33 | 1.48 ± 0.66 | 0.22 ± 0.06 | 2.65 ± 1.39 | 1.37 ± 0.03 |
| BO-2772 | 0.32 ± 0.20 | 0.52 ± 0.16 | 0.27 ± 0.31 | 1.67 ± 0.24 | 1.01 ± 0.49 |
| BO-2756 | 0.13 ± 0.10 | 0.74 ± 0.39 | 0.15 ± 0.087 | 1.51 ± 0.83 | 0.81 ± 0.02 |
| BO-2793 | 0.06 ± 0.02 | 0.09 ± 0.04 | 0.01 ± 0.003 | 0.31 ± 0.21 | 0.13 ± 0.09 |
| BO-2763 | 0.68 ± 0.59 | 1.58 ± 1.37 | 0.18 ± 0.06 | 2.16 ± 0.50 | 1.15 ± 0.15 |
| B0-2757 | 1.03 ± 0.25 | 1.58 ± 0.01 | 0.54 ± 0.18 | 4.19 ± 0.70 | 3.94 ± 0.11 |
| Irinotecan | 8.81 ± 0.46 | 2.26 ± 0.01 | 0.59 ± 0.30 | 11.51 ± 6.53 | 9.79 ± 0.84 |
| Etoposide | 0.07 ± 0.01 | 1.08 ± 0.42 | 0.20 ± 0.26 | 2.91 ± 0.17 | 4.53 ± 3.18 |
| Cisplatin | 0.78 ± 0.46 | 1.75 ± 0.39 | 1.75 ± 0.71 | 10.20 ± 2.99 | 40.81 ± 5.97 |
| Carboplatin | 13.87 ± 1.56 | N.D. | 6.43 ± 0.14 | 37.13 ± 6.38 | 8.64 ± 1.93 |

4.2 Compound of Formula (I) Induced DNA Interstrand Crosslinks

In the present example, BO-2590, BO-2577 (Formula I-A) and BO-2698, BO-2755, BO-2762 and BO-2768 (Formula I-B) were tested for their DNA crosslinking activity, in which the cross-linking was analyzed by alkaline agarose gel electrophoresis. In brief, purified pEGFP-N1 plasmid DNA (1,500 ng) was mixed with various concentrations (1-20 µM) of the tested compounds in 40 µL binding buffer (3 mM sodium chloride/1 mM sodium phosphate, pH 7.4, and 1 mM EDTA). The reaction mixture was incubated at 37° C. for 2 hrs. At the end of reaction, the plasmid DNA was linearized by digestion with BamHI and followed by precipitation with ethanol. The DNA pellets were dissolved and denatured in alkaline buffer (0.5 N NaOH-10mM EDTA). An aliquot of 20 µL of DNA solution (1,000 ng) was mixed with 4 µL of 6× alkaline loading dye and then electrophoretically resolved on a 0.8% alkaline agarose gel with NaOH-EDTA buffer at 4° C. The electrophoresis was carried out at 18V for 22 h. After staining the gels with an ethidium bromide solution, the DNA was visualized under UV light. Results are illustrated in FIG. 1.

As depicted in the photographs in FIG. 1, BO-2590, BO-2577, BO-2698, BO-2755, BO-2762 and BO-2768 respectively induced DNA interstrand crosslinks, and the effect appeared to be in a dose-dependent manner. Further, among the compounds that were tested, BO-2590 was found to be a relatively stronger cross-linker than that of melphalan.

Figure 2:
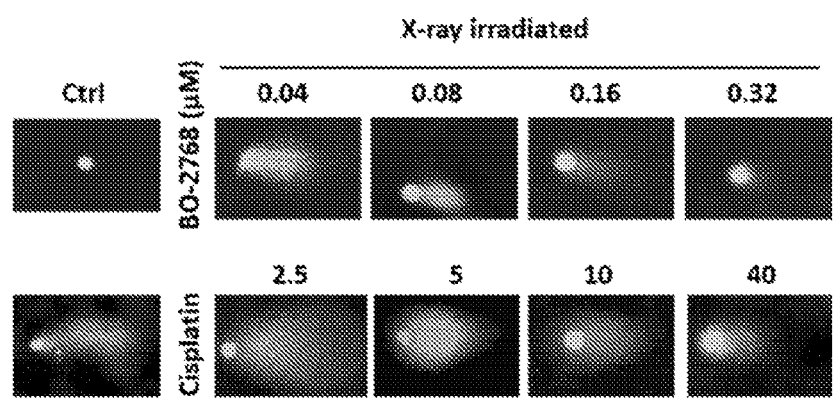
FIG. 2 illustrates the effect of BO-2768 or cisplatin on DNA interstrand cross-links in H526 cells in accordance with one embodiment of the present disclosure; in which (A) are representative images of individual cells showing comet tail by modified comet assay, and (B) are bar graphs depicting the tail moments in cisplatin or BO-2768 treated cells. The shorter tail moment indicates the stronger DNA interstrand crosslinks. The data is the average of 3 independent experiments.
Figure 2:
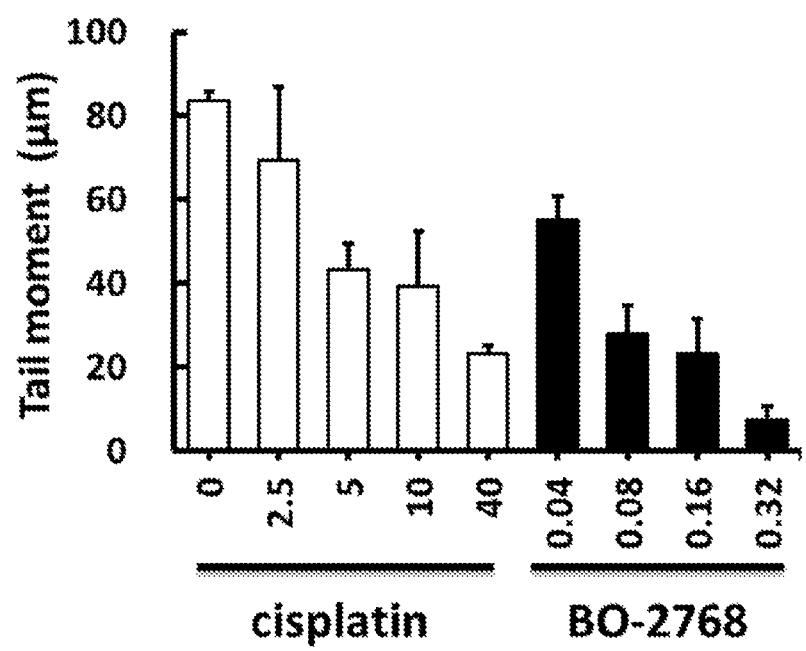

Further, the single cell electrophoresis assay (SCGE, also known as "comet assay") was preformed to assess DNA damage induced by BO-2768, which is a simple method for measuring DNA strand breaks in cells. To this purpose, cells were encapsulating in a low-melting-point agarose suspension on a microscope slide, then were lysed in neutral or alkaline (pH>13) condition, and electrophoresis of the suspended lysed cells. The term "comet" refers to the pattern of DNA migration through the electrophoresis gel, which often resembles a comet, and the intensity of the comet tail relative to the head reflects the number of DNA breaks. Results are depicted in FIG. 2, which confirms that BO-2768 was capable of inducing DNA breaks in a dose dependent manner as cisplatin.

4.3 BO-2590 and BO-2577 Inhibited Angiogenesis

In the present example, BO-2590 and BO-2577 were subject to the test of their activity in suppressing VEGFR-2 by western blotting analysis. Briefly, the endothelial EA.hy926 cells were incubated with BO-2590 or BO-2577 at various concentrations for 12 hr. The primary antibodies, anti-VEGFR-2 and anti-p-VEGFR-2, were used to blot the proteins of total VEGFR-2 and p-VEGFR-2, respectively. Results are illustrated in FIG. 3.

Figure 3:
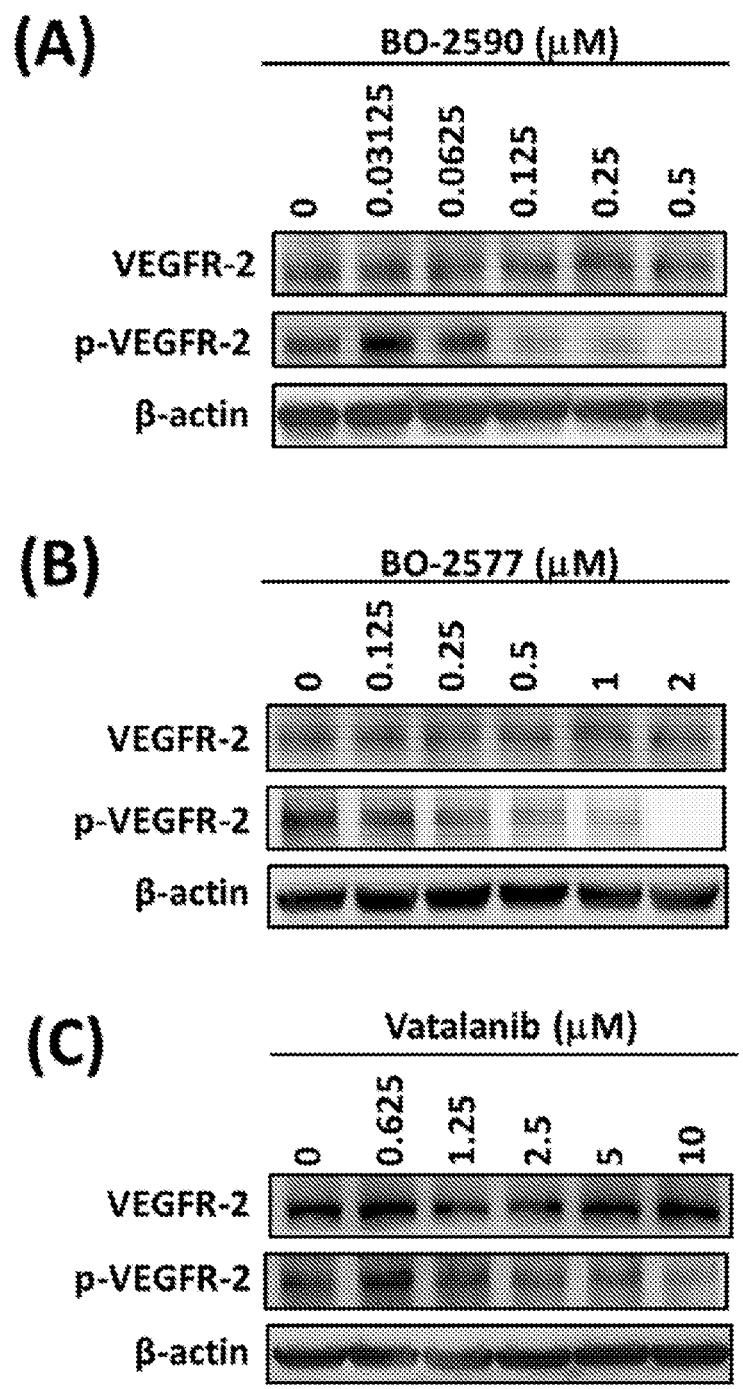
FIG. 3 are photographs illustrating the inhibitory effects of (A) BO-2590, (B) BO-2577 or (C) vatalanib on VEGFR-2 activation in accordance with one embodiment of the present disclosure.

As depicted in FIG. 3, treatment with BO-2590 or BO-2577 resulted in a marked suppression in p-VEGFR-2 protein levels, and BO-2590 was more potent that BO-2577 in decreasing p-VEGFR-2. Further, since BO-2590 or BO-2577 did not significantly change the total protein levels of VEGFR-2, we thus speculated that BO-2590 or BO-2577 might function as an inhibitor of VEGFR activation. Valatanib was therefore included as a control. Surprisingly, the dose of BO-2590 effective on suppression of p-VEGFR-2 was approximate 10 folds lower than that of Valatanib. It revealed that BO-2590 is a potent inhibitor of VEGFR-2.

4.4 BO-2590 Reduced the Migration of Endothelial Cells

In the present example, we explored whether compound BO-2590 was able to suppress the cell migration using transwell migration assay.

Figure 4:
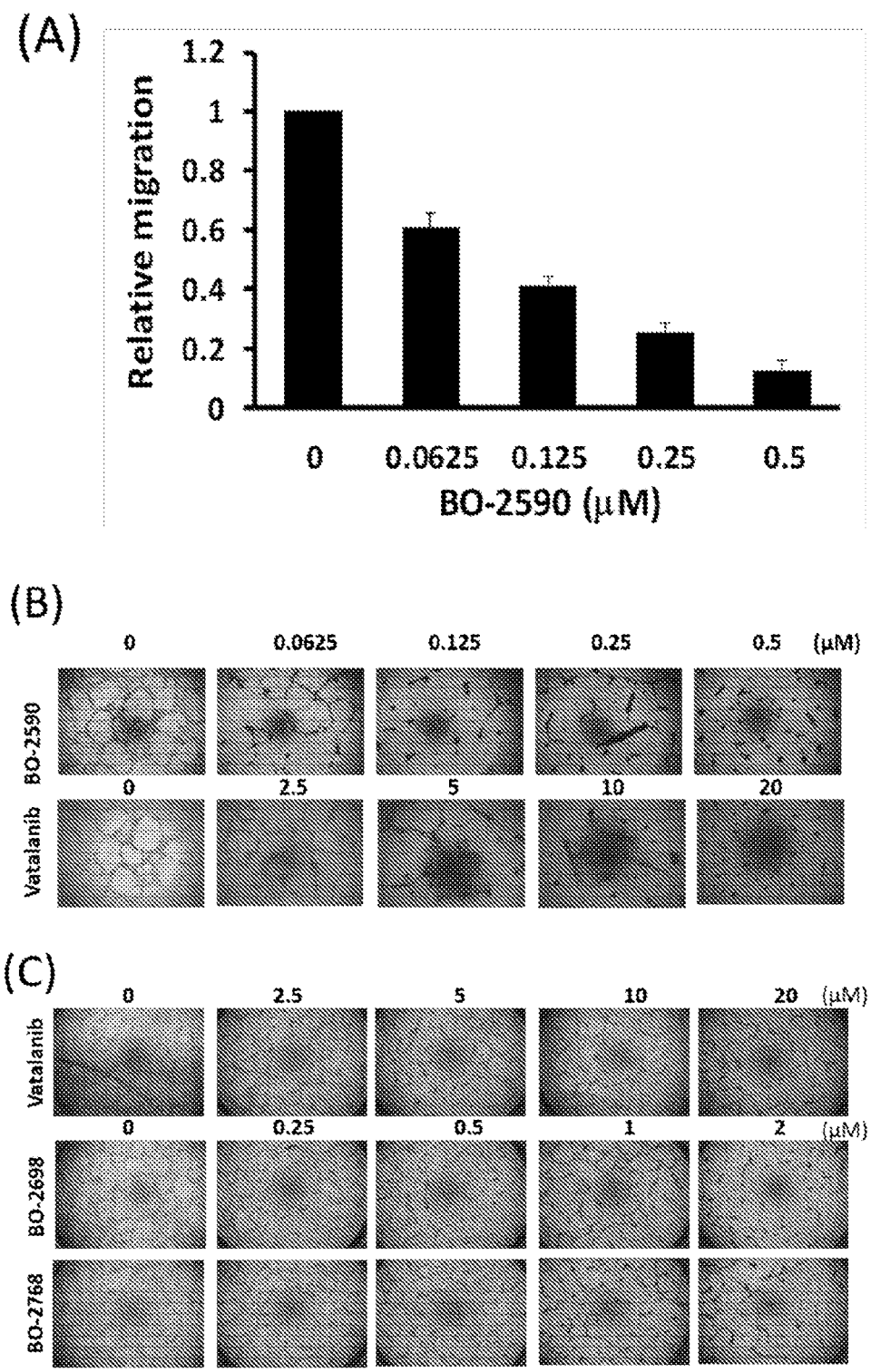
FIG. 4 illustrates anti-angiogenic effects of BO-2590, BO-2698, and BO-2768 on endothelial cells in accordance with one embodiment of the present disclosure, in which (A) is the inhibition on the migration of endothelial cells measured by transwell, (B) and (C) are photographs depicting the inhibition determined by tube formation, and (D) are lines graphs depicting the quantitated results of panels (A) and (B)
Figure 4:
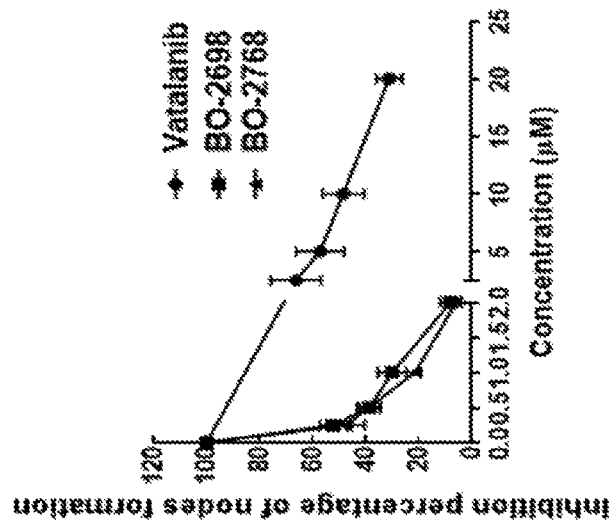
Figure 4:
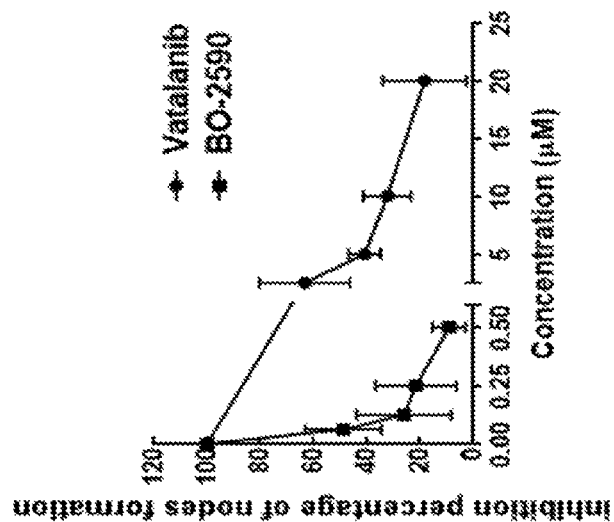

Briefly, the endothelial cells were placed on the upper layer of a cell permeable membrane and a solution containing BO-2590 was placed below the cell permeable membrane. Following an incubation period (8 hours), the cells that had migrated through the membrane were stained and counted under a fluorescence microscopy. Apparently, inhibition of VEGFR pathway by compound BO-2590 was accompanied by an impairment in cell migration (FIG. 4, panel A).

4.5 BO-2590 Interrupted Angiogenesis

Angiogenesis is the process of generating new blood vessels derived as extensions from the existing vasculature. Performance of vascular behavior or monitoring tube formation can determine whether the compound is capable of interrupting angiogenesis. In this example, whether the compound of formula (I) interrupted angiogenesis was investigated using Tube-Formation Assay.

Briefly, EA.hy926 cells were treated with various concentrations of BO-2590 for 24 hr. After that, cells ($5\times10^5$ cells/well) were suspended in 100 μl medium containing 1% FCS and subsequently seeded onto 96-well plate pre-coated with matrigel 1 h at 37° C. After a 48-hr incubation, tube-formation ability was examined under a phase microscope.

As the photos in FIG. 4 (panel B) indicated, robust tubular structures were formed in the absence of BO-2590, whereas pre-incubation with nM range of BO-2590 markedly and dose-dependently abolished tube formation of tubular structures. vatalanib also suppressed tube formation, but at much higher concentrations. The results indicated that the inhibition of tube formation by BO-2590 is closely correlated to BO-2590 induced VEGFR-2 inhibition. Therefore, it is reasonable to conclude that BO-2590 triggered the anti-angiogenesis activity via the inhibition of p-VEGFR2 expression. BO-2768 and BO-2698 also exhibited similar inhibitory effects on tube formation in dose-dependent manner (FIG. 4, panels C and D).

4.6 BO-2590 Interfered Cell Cycle

Figure 5:
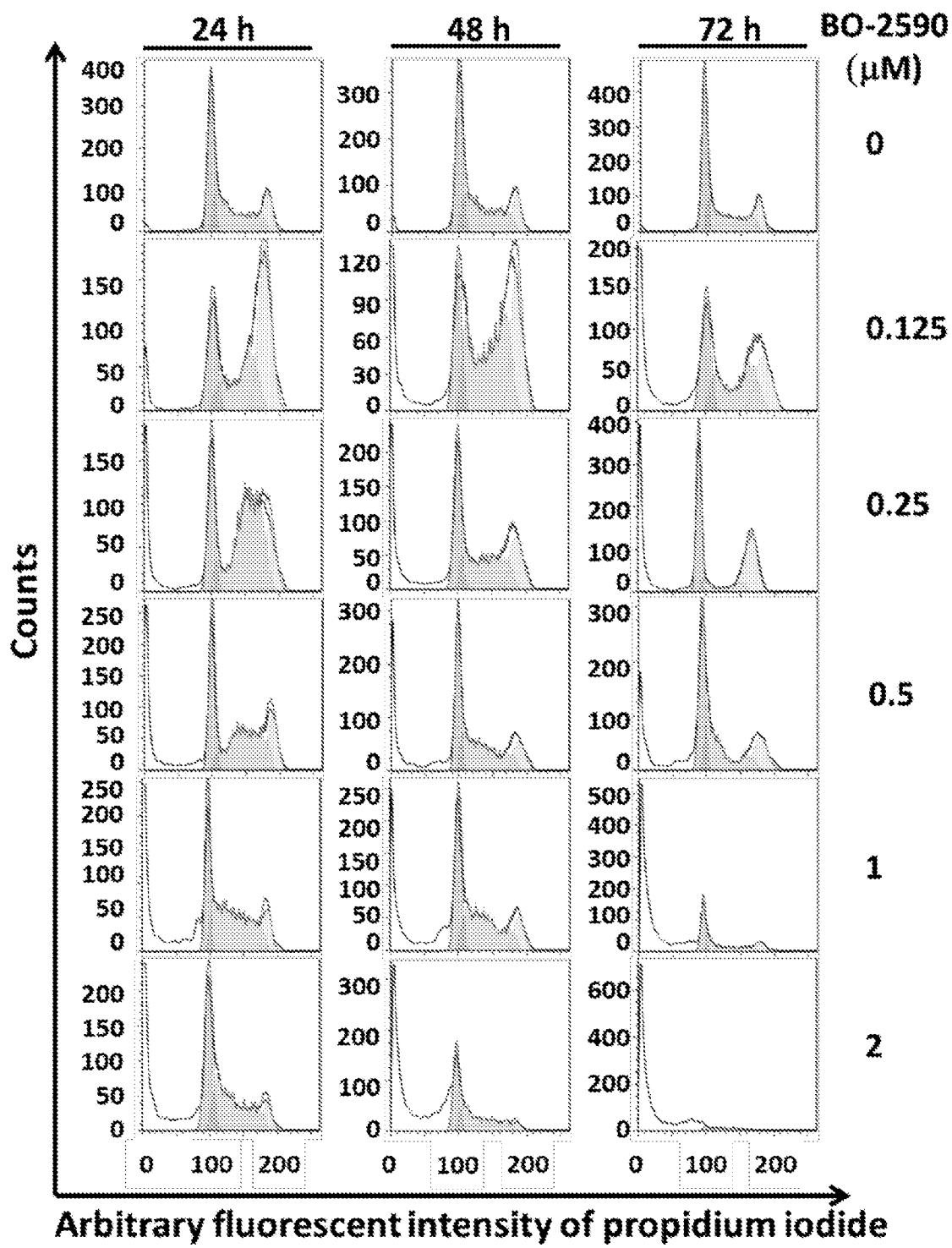
FIG. 5 illustrates cell cycle interference by BO-2590 in H460 human lung cancer cells in accordance with one embodiment of the present disclosure.
Figure 6:
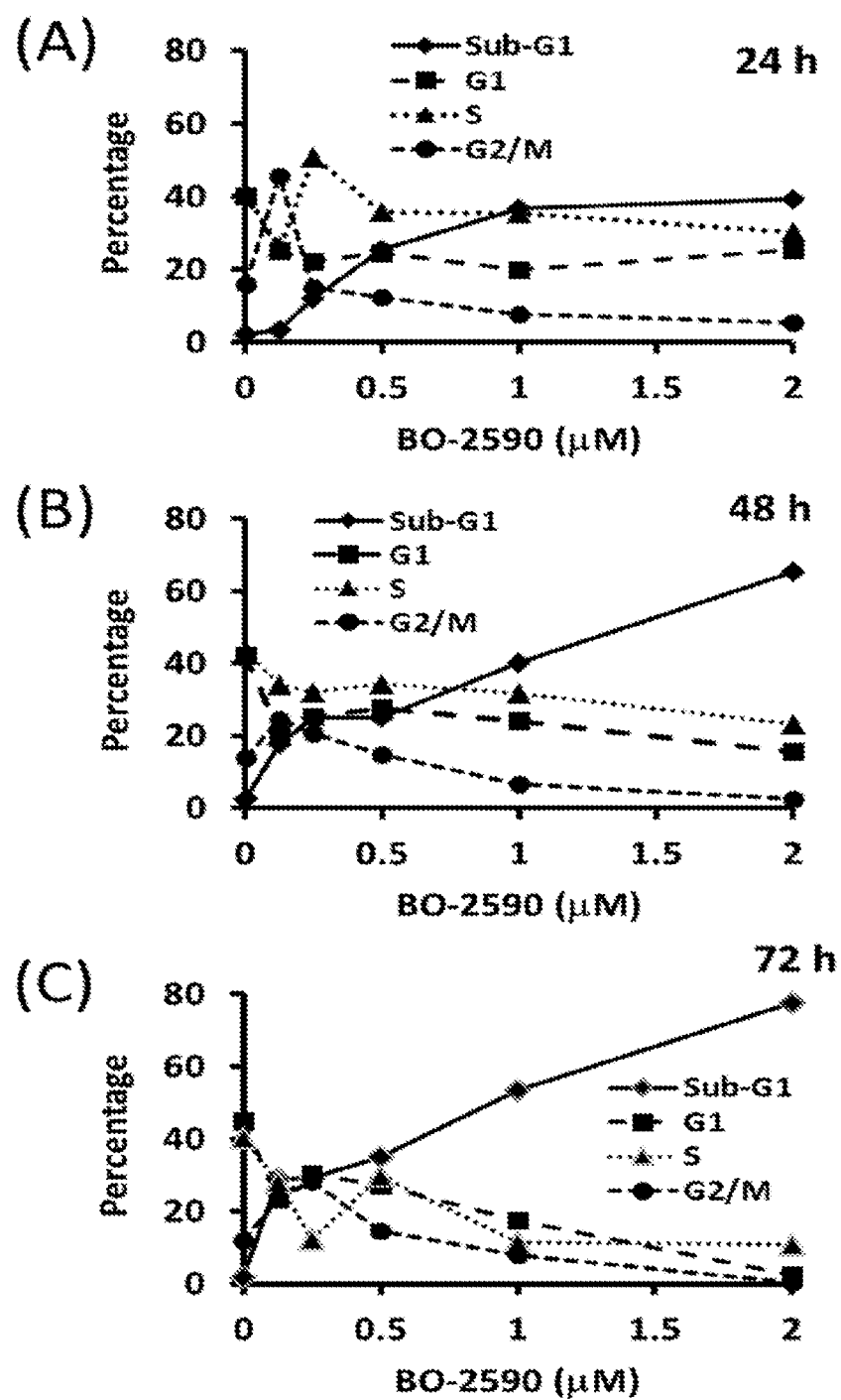
FIG. 6 illustrates the induction of apoptotic sub-G1 cells by BO-2590 in H460 human lung cancer cells at (A) 24 hr, (B) 48 hr or (C) 72 hr in accordance with one embodiment of the present disclosure.

We further investigated the effects of BO-2590 on cell cycle progression in H460 lung cancer cells at the concentrations of 0, 0.125, 0.25, 0.5, 1 and 2 μM for 24, 48 and 72 hr. The cell cycle distribution was analyzed by flow cytometry. As illustrated in FIG. 5, BO-2590 dose-dependently interfered with cell cycle progression. By increasing the concentration of BO-2590, significant arrest at the G2 phase was first observed, which was followed by the arrest of the S phase progression, and finally the G1 arrest appeared at 24 hr. However, following the incubation for 48 or 72 hr, while the cell cycle slowly processed, a significant amount of the sub-G1 cells started to appear (FIG. 6). The sub-G1 cells also represented apoptotic cells. Thus, the finding that BO-2590 dose-dependently induced the sub-G1 cells indicates that BO-2590 could trigger the apoptotic cell death via DNA damage.

4.7 BO-2590 Induced Apoptotic Cell Death

Figure 7:
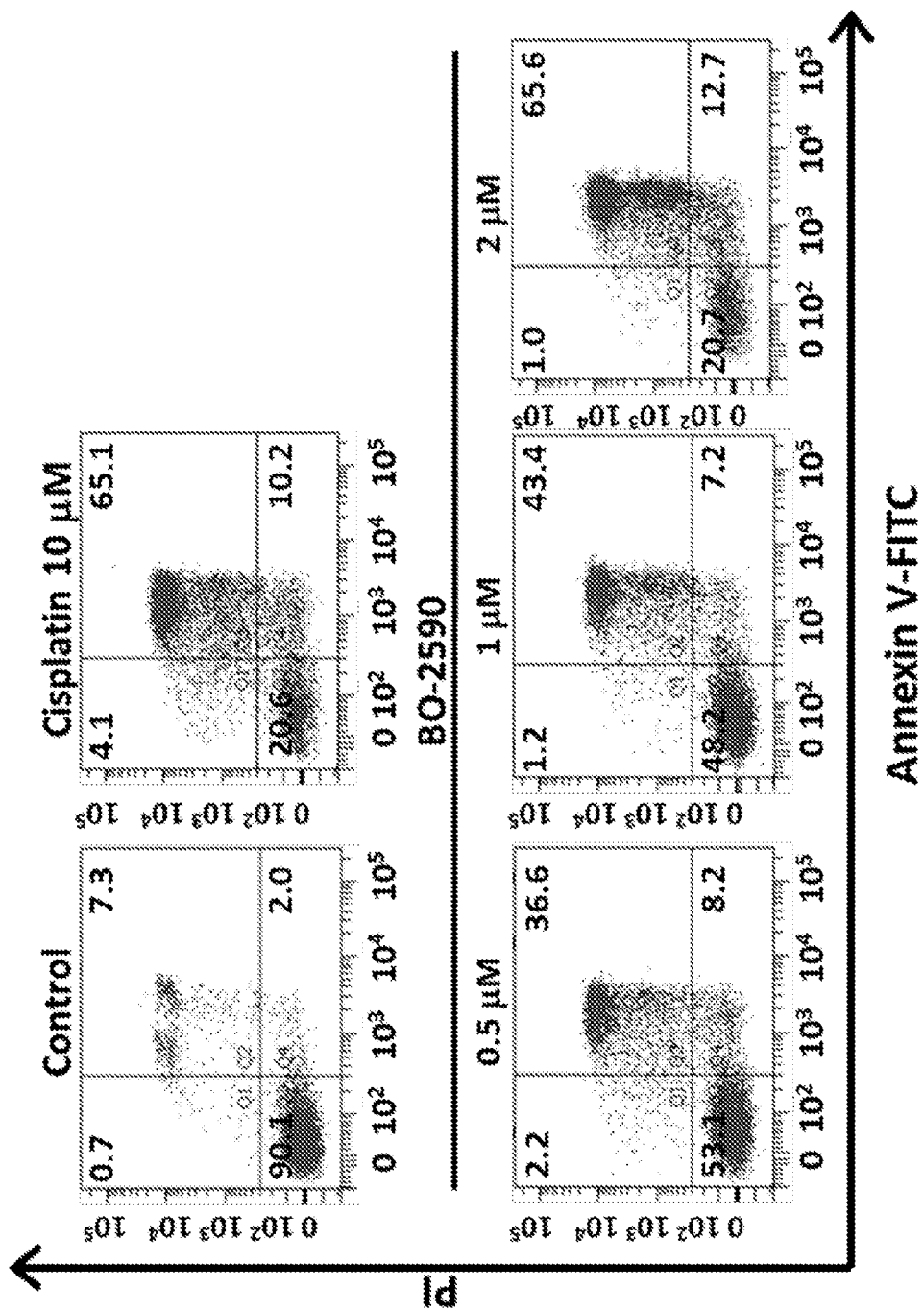
FIG. 7 illustrates the induction of Annexin V+apoptotic death by BO-2590 or cisplatin in accordance with one embodiment of the present disclosure.

In this example, Annexin V staining assay was used to assess BO-2590 induced apoptotic cell death in H460 cell lines. Briefly, H460 cells were treated with BO-2590 at the concentrations of 0.5, 1 and 2 μM for 48 hr and then stained with Annexin V-FITC and propidium iodide. The stained cells were analyzed by flow cytometry. After a 48-h treatment, it was found that BO-2590 significantly increased the proportion of Annexin $V^+$ cells in a dose-dependent manner (FIG. 7).

4.8 BO-2768 Induced Apoptotic Cell Death

Figure 8:
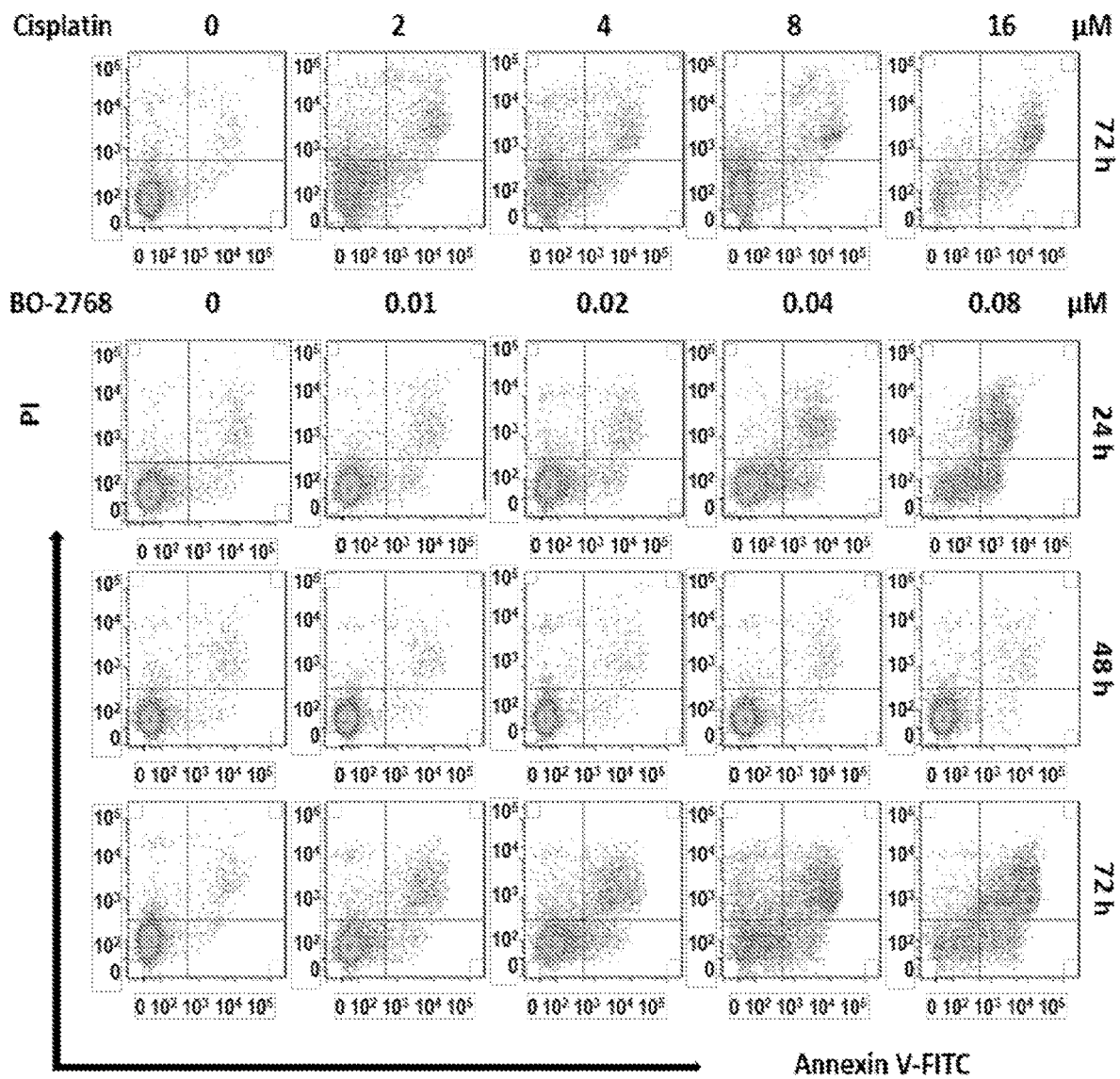
FIG. 8 illustrates the induction of apoptosis in H526 cells by BO-2768 in accordance with one embodiment of the present disclosure.

In this example, the effect of BO-2768 was assessed in accordance with procedures of Example 4.7 except apoptotic cell death was determined in H526 cell lines. Briefly, H526 cells were treated with BO-2768 at the concentrations of 0.01, 0.02, 0.04 and 0.08 μM or with cisplatin at the concentrations of 2, 4, 8 and 16 μM for 24, 48 or 72 hrs and then stained with Annexin V-FITC and propidium iodide. The stained cells were analyzed by flow cytometry. After 72-h treatment, it was found that BO-2768 significantly increased the proportion of Annexin $V^+$ cells in a dose-dependent manner (FIG. 8).

4.9 BO-2768 and Cisplatin Synergistically Suppressed Cell Proliferation

In this example, whether synergistic effect on the suppression of cell proliferation exists between BO-2768 and cisplatin was investigated. To this purpose, H211 cells were treated with BO-2768 or cisplatin, alone or in combination, and proliferation rate of H211 cells was analyzed by Presto-Blue assay. Results are depicted in FIG. 9.

Figure 9:
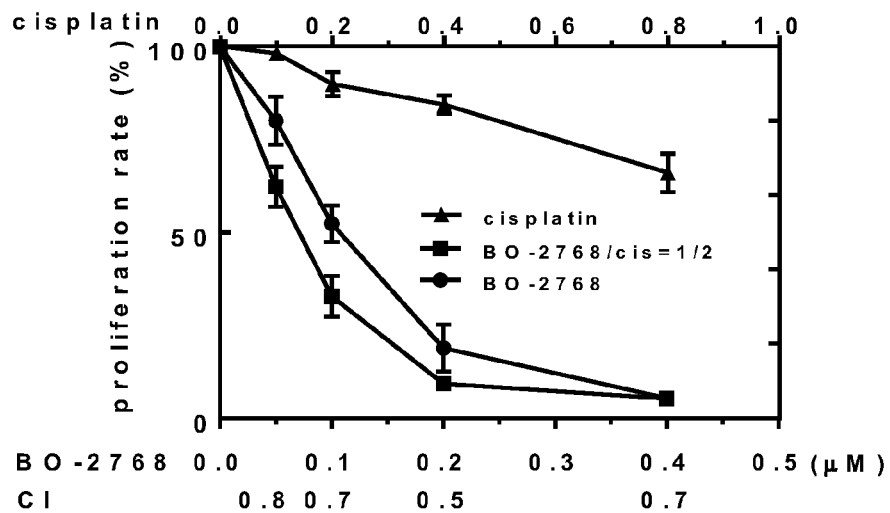
FIG. 9 are line graphs depicting the synergistic effect of BO-2768 and cisplatin in the ratio of (A) 1:2, (B) 1:4 (B), (C) 1:8, respectively on the suppression of proliferation of H211 cells in accordance with one embodiment of the present disclosure; the synergism or antagonism between different combined doses was calculated using combined index (CI), where CI=1 indicates that two drugs have additive effects, CI<1 indicates better than additive effects ("synergism"), and CI>1 indicates worse than additive effects (antagonism)
Figure 9:
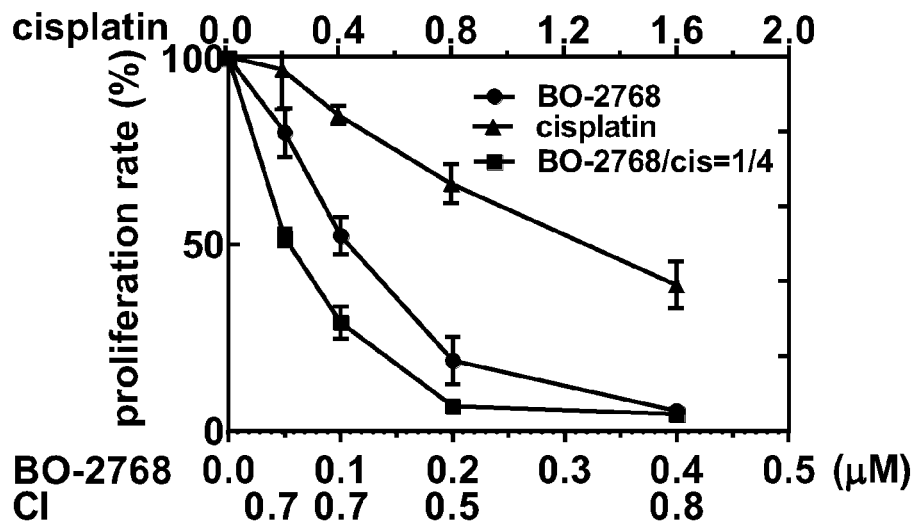
Figure 9:
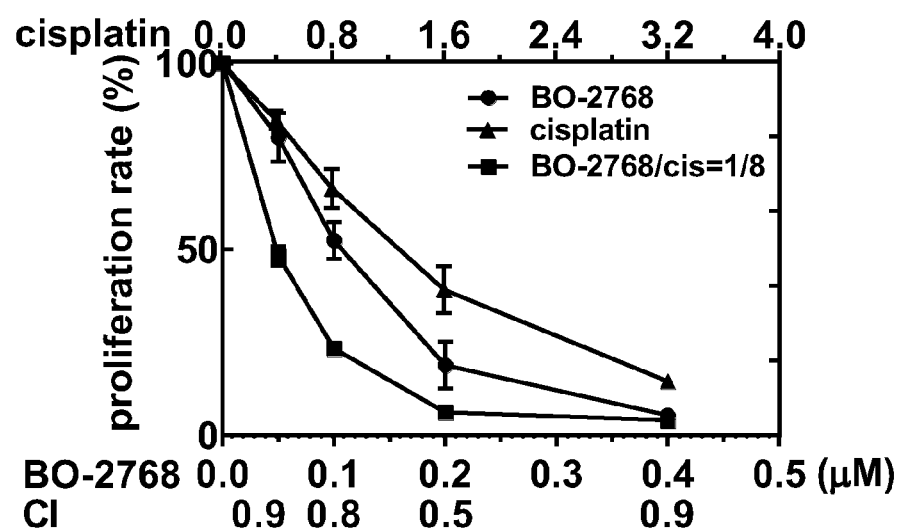

As the data in FIG. 9 indicated, co-administration of BO-2768 and cisplatin in a ratio of 1:2, 1:4 and 1:8 respectively resulted in synergistic reduction in the numbers of proliferated H211 cells.

Example 5 In Vivo Characterization of the Compounds of Formula (I)

As described previously in Example 4, the compounds of formula (I) were generally cytotoxic to the tumor cell lines tested. In the present example, the therapeutic efficacy of the selected compounds of formula (I) in nude mice bearing human SCLC were investigated.

5.1 liposomal BO-2590 (BO-2590L) of Example 3 Effectively Suppressed SCLC 11526 Xenografts Since the solubility of BO-2590 was poor, thus liposomal BO-2590 (BO-2590L) of example 3 was used in the present example to investigate its therapeutic efficacy on nude mice bearing human SCLC H526 xenografts.

Figure 10:
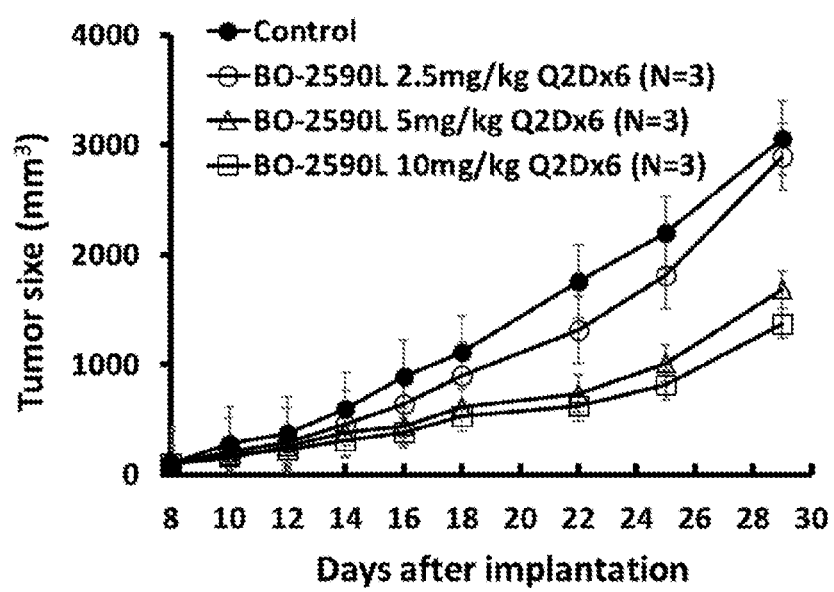
FIG. 10 illustrates the effects of liposomal BO-2590L on (A) tumor size, and (B) the body weight changes in H526 xenograft-bearing nude mice in according with one embodiment of the present disclosure.
Figure 10:
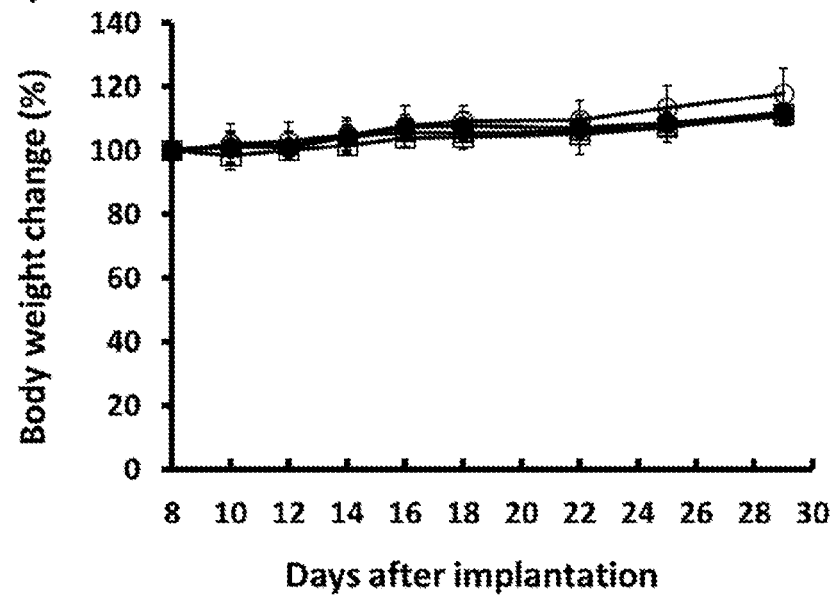

In all experiments, the tumor cells were subcutaneously implanted in nude mice, and the BO-2590L was administered via tail vein when the tumor size reaching approximate 100 $mm^3$. The H526 xenograft-bearing mice were first treated with BO-2590L at the dose of 2.5, 5 and 10 mg/kg, every other day for six times (Q2D×6). As illustrated in FIG. 10 (panel A), BO-2590L at 10 mg/kg suppressed H526 tumor volume by 55% on D30. At all the doses that were tested, BO-2590L did not cause lost in body weight, which indicated low toxicity of BO-2590L (FIG. 10, panel B).

To confirm the therapeutic activity of BO-2590L, comparative experiments carried out by known chemotherapeutic agents, such as vatalanib and cisplatin, were also performed. Briefly, the H526 xenograft-bearing mice were divided into 4 groups which were treated with vehicle, BO-2590L (10 mg/kg, QD×9), vatalanib (100 mg/kg, QD×9), and cisplatin (4 mg/kg, Q2D×3), respectively. Results are illustrated in FIG. 11.

Figure 11:
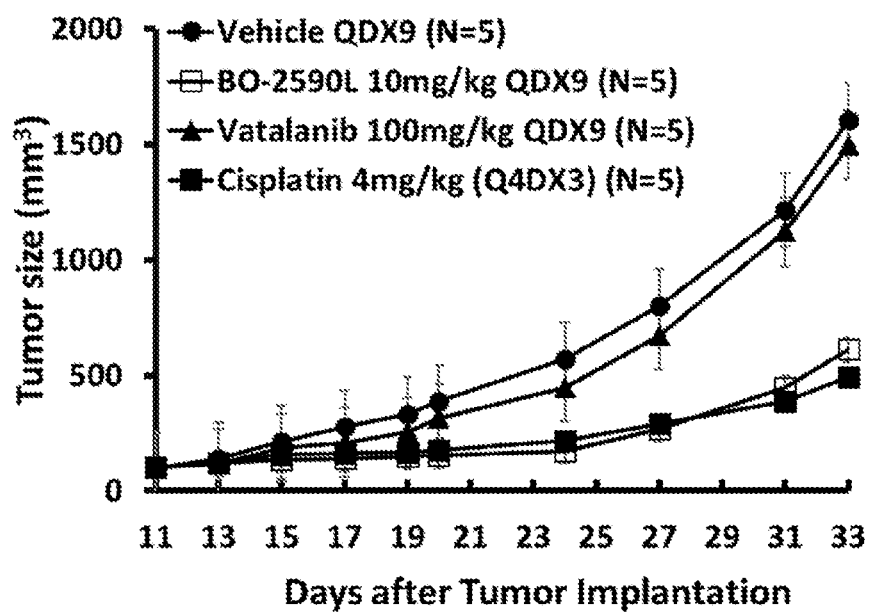
FIG. 11 illustrates the respective effects of liposomal BO-2590L, vatalanib, and cisplatin on (A) tumor size, and (B) the body weight changes in H526 xenograft-bearing nude mice in accordance with one embodiment of the present disclosure.
Figure 11:
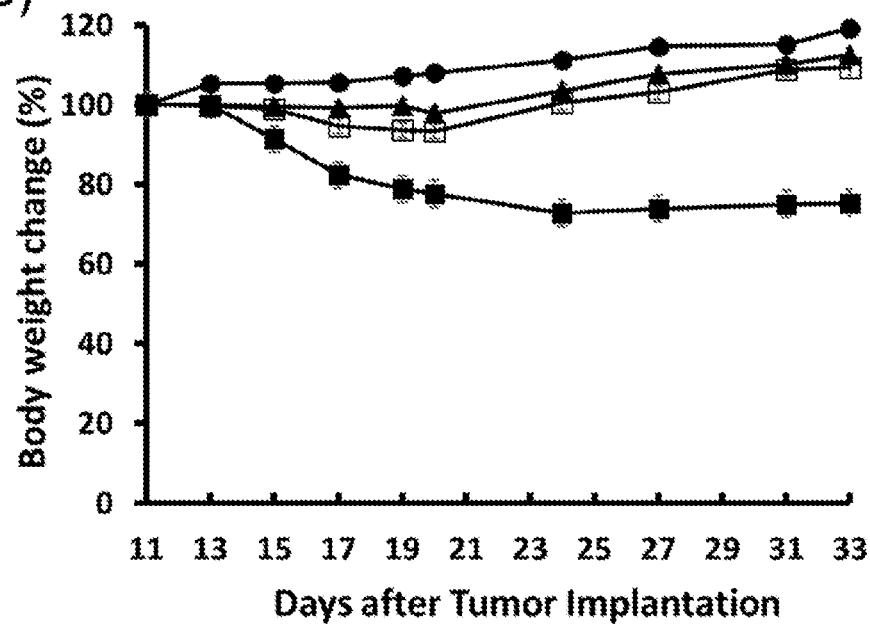

It was found that BO-2590L was far more potent than vatalanib and was almost as effective as cisplatin on D33 in suppressing the growth of H526 xenografts; approximately 60% tumor suppression was observed by BO-2590L (FIG. 11, panel A). Notably, BO-2590L given at 10 mg/kg for consecutive 9 days did not cause body weight lost (FIG. 11, panel B), supporting the previous finding that BO-2590L possessed low toxicity. By contrast, cisplatin at the dose of 4 mg/Kg used resulted in severe body weight lost in the test animals.

Figure 12:
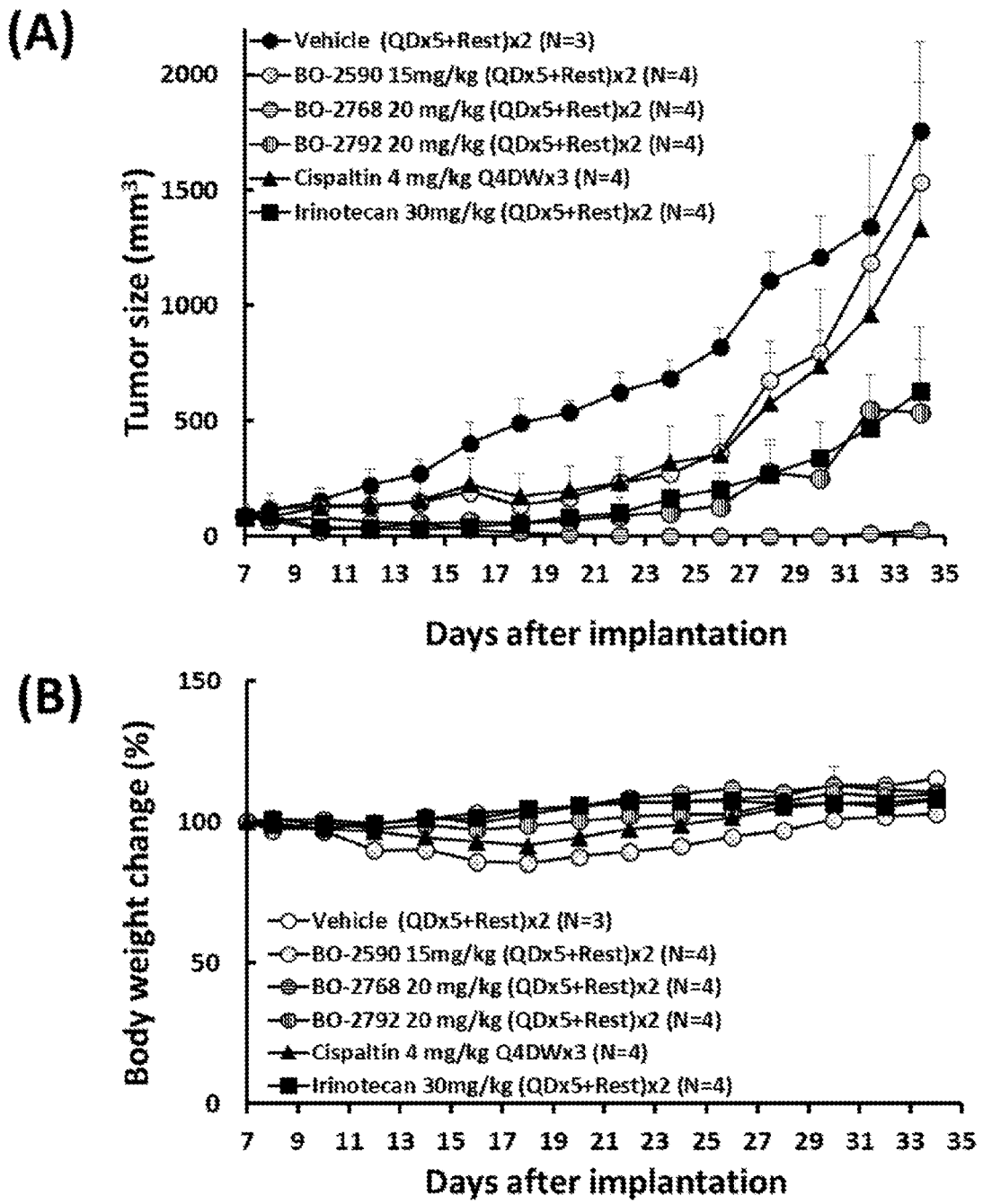
FIG. 12 illustrates the respective effects of micelle BO-2590, BO-2768, BO-2792, irinotecan, and cisplatin on (A) tumor size, and (B) the body weight changes in H526 xenograft-bearing nude mice in accordance with one embodiment of the present disclosure.

5.2 Micelle BO-2590, BO-2768, BO-2792 effectively Suppressed SCLC 11526 Xenografts The therapeutic efficacies of BO-2590, BO-2768, BO-2792, irinotecan, and cisplatin on nude mice bearing human SCLC H526 xenografts were investigated in accordance with similar procedures in Example 5.1. BO-2590, BO-2768, BO-2792, irinotecan, and cisplatin were formulated in a solution of 20% Kolliphor 15g, 10% TWEEN 80, 10% PEG400, 30% ethanol, and 40% D5W, respectively. Results are illustrated in FIGS. 12 and 13.

It was found that BO-2590 and BO-2792 were as effective as irinotecan and cisplatin in reducing the tumor size (FIG. 12, panel A); however, BO-2768 at the dose of 20 mg/kg (twice daily) was surprisingly more potent than any of BO-2590, BO-2792, irinotecan, or cisplatin, in which the growth of tumor was completely suppressed (i.e., no growing) throughout the entire time of this study, while the tumor in other groups (i.e., BO-2590, BO-2792, irinotecan, or cisplatin-treated groups) slowly increased in size along with an increased in time. Further, none of the test compounds (i.e., BO-2590, BO-2768, BO-2792, irinotecan, and cisplatin) exhibited any deleterious effects on the bodyweight of the test animals (FIG. 12, panel B).

5.3 BO-2768 Suppressed SCLC 11526 Xenografts in a Dose-Dependent Manner

Figure 13:
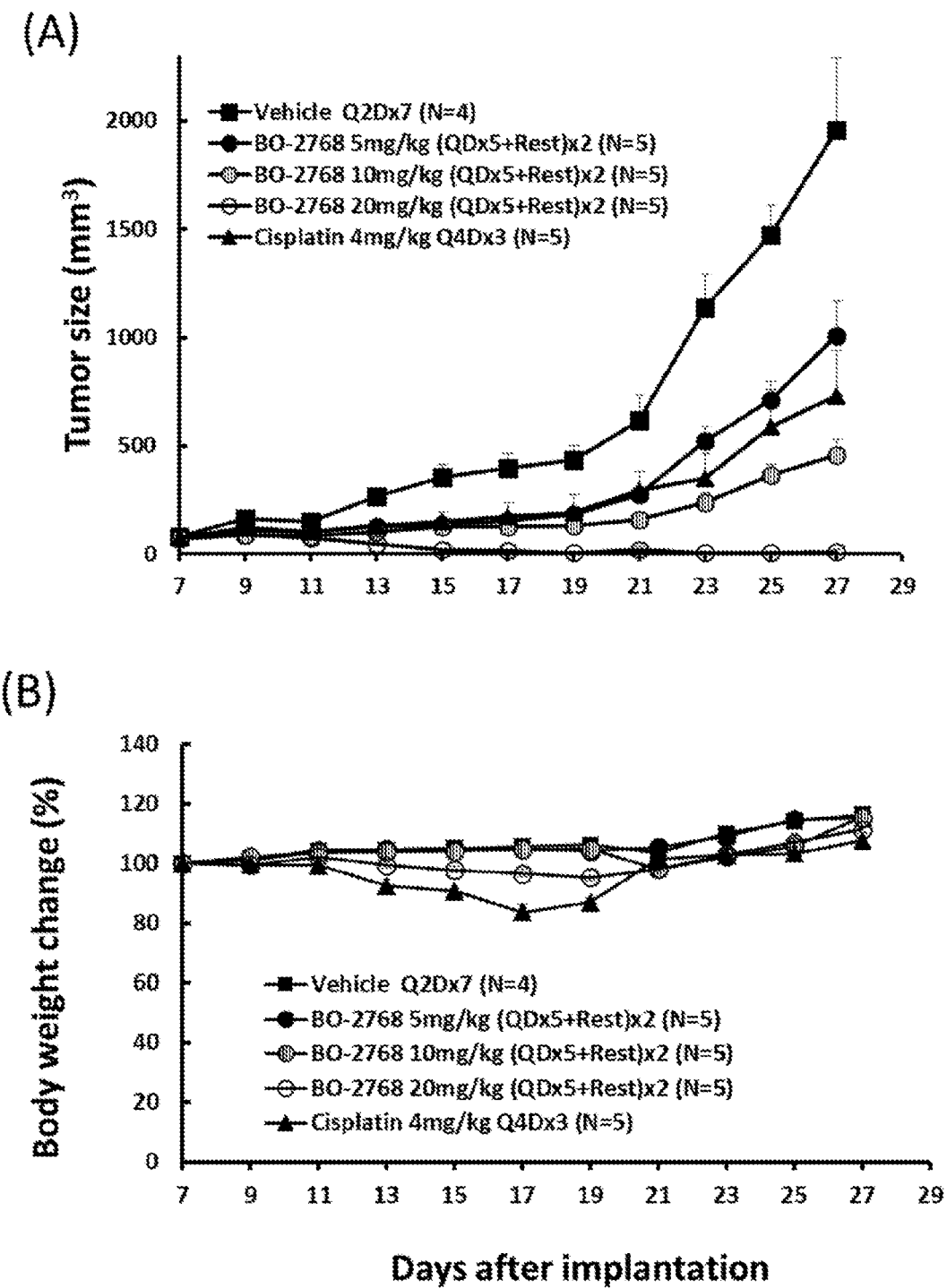
FIG. 13 are line graphs depicting dose-dependent inhibitory effect of BO-2768 on (A) tumor size, and (B) the body weight changes in H526 SCLC xenograft-bearing nude mice in accordance with one embodiment of the present disclosure.

In view of the finding in Example 5.2, the anti-tumor efficacy of BO-2768 was investigated in further detail, and as expected, BO-2768 suppressed tumor growth in a dose-dependent manner, and the dose of 20 mg/kg (twice per day) may completely suppress the growth of tumor throughout the entire time of the study (FIG. 13, panel A) without any deleterious effects on the bodyweight of the test animals (FIG. 13, panel B).

5.4 BO-2768 and Cisplatin Synergistically Reduced the Size of SCLC 11211 Xenografts Without Adversely Affecting the Body Weight of the Test Subjects In this example, the synergistic effect of BO-2768 and cisplatin on the suppression of tumor size and the body weight changes of the test subjects were investigated. To this purpose, an aliquot of H211 cells ($5\times10^6$, 50 µl) were implanted into nude mice subcutaneously. Then, the test animals were treated with BO-2768 or cisplatin, alone or in combination. BI-2768 (dissolved in 20% Kolliphor® HS 15, 10% Tween 80, 10% PEG400, 30% Ethanol, and 40% distilled water) was administered at the dose of 20 mg/kg in 100 pi for 5 consecutive days, then rest for one day; and the cycle was repeated once (i.e., a total of two cycles). Cisplatin was given at the dose of 2 or 4 mg/kg once every 4 days, for 3 times. Results are depicted in FIG. 14.

Figure 14:
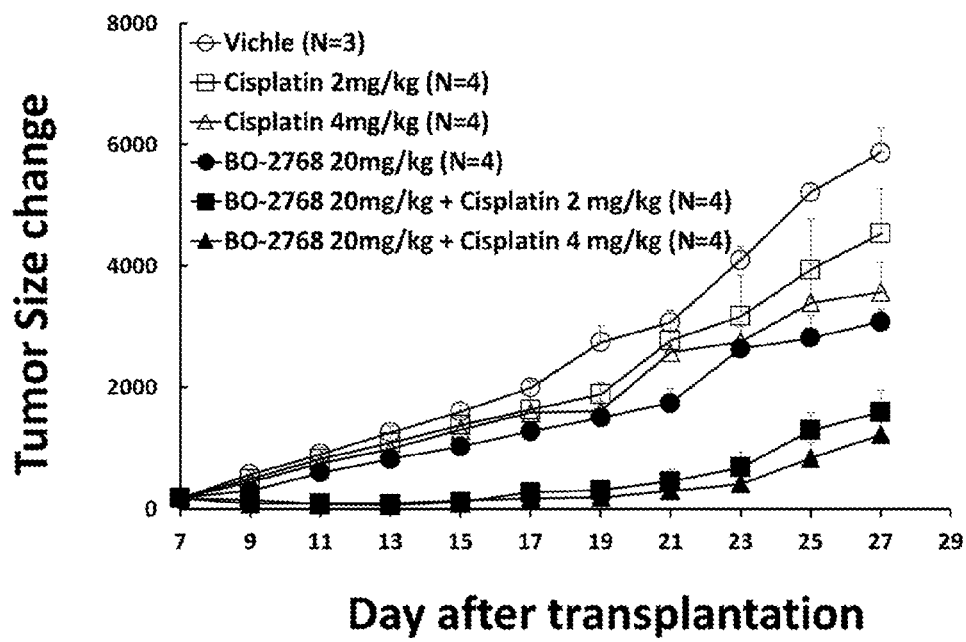
FIG. 14 illustrates the effects of combinational use of BO-2768 and cisplatin on (A) tumor size, and (B) the body weight changes in H211 SCLC xenograft-bearing nude mice in accordance with one embodiment of the present disclosure. The BO-2768 administered at the dose of 20 mg/kg in 100 µl for 5 consecutive days and one day rest in two cycles. Cisplatin was given at the dose of 2 or 4 mg/kg once every 4 day for 3 times. The body weight changes were observed after drug treatment.
Figure 14:
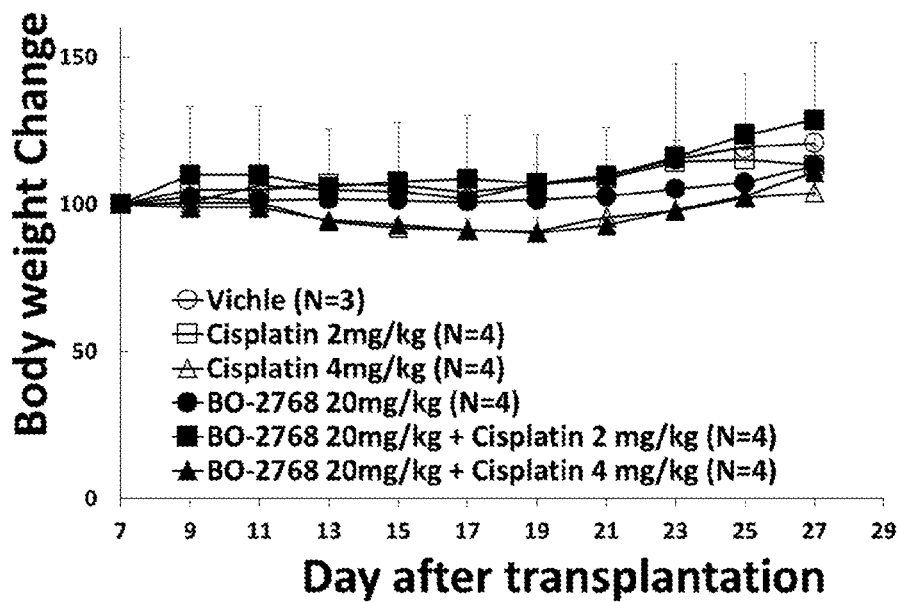

As the data in FIG. 14 indicated, co-administration of BO-2768 and cisplatin resulted in a synergistic reduction in the tumor size (FIG. 14, panel A), without adversely affecting the body weight of the test animals (FIG. 14, panel B).

5.5 Anti-Angiogenic and DNA Damage Activities of BO-2590L (Formula IA) in Tissue Sections of SCLC 11526 Demonstrated by Immunohistochemical Staining Tumor xenograft tissue sections on the slides were deparaffinized in xylene twice for 7 min each time. The slides were then rehydrated in graded ethanol, serially from 100% to 70%, followed by rinsing in $dH_2O$. Antigen retrieval was performed using citrate buffer (0.01M, pH 6.0) with incubation in a cooker for 50 mins followed by ambient temperature cooling for 30 min. and then $dH_2O$ rinsing. Later slides were subjected to immunohistochemical (IHC) staining with primary antibodies (anti-rabbit CD31 antibody and anti-mouse γ-$H_2$AX antibody) obtained from Abeam® following the manufacturer's instructions (Novolink Polymer Detection system, Leica Biosystems, Wetzlar, Germany).[11] After IHC processing, the slides were scanned digitally using the Panoramic 250 Flash II whole slide scanner and analyzed by 3DHISTECH Panoramic viewer software (3DHISTECH Ltd., Budapest, Hungary).

Figure 15:
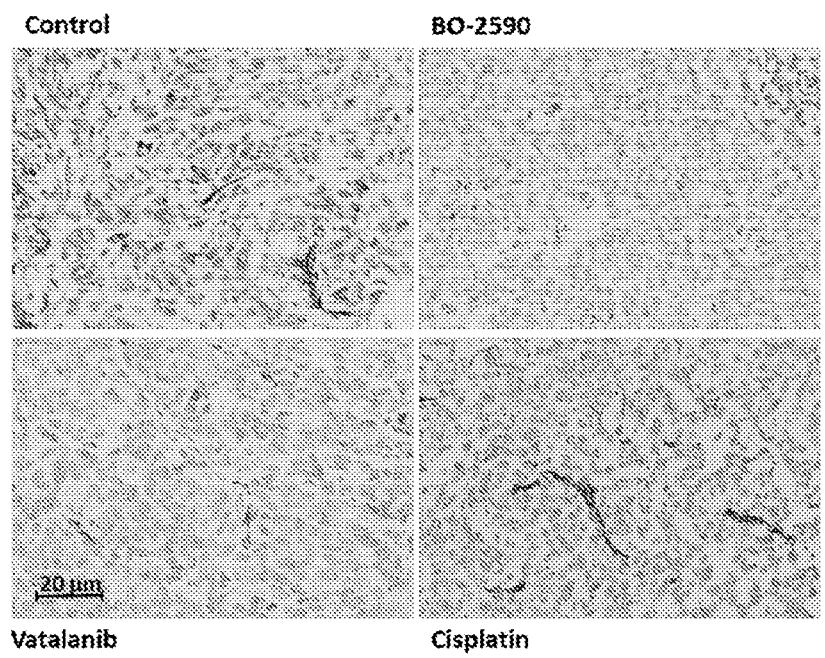
FIG. 15 illustrates effects of BO-2590L, cisplatin or vatalanib on the level of CD3 I marker in tumors in accordance with one embodiment of the present disclosure; in which (A) Representative IHC staining using antibody against CD3 I at day 6 after treatment, and (B) Quantitative signals of CD3 I in tumors. Data are represented as the mean±SD of 15 fields per group.
Figure 15:
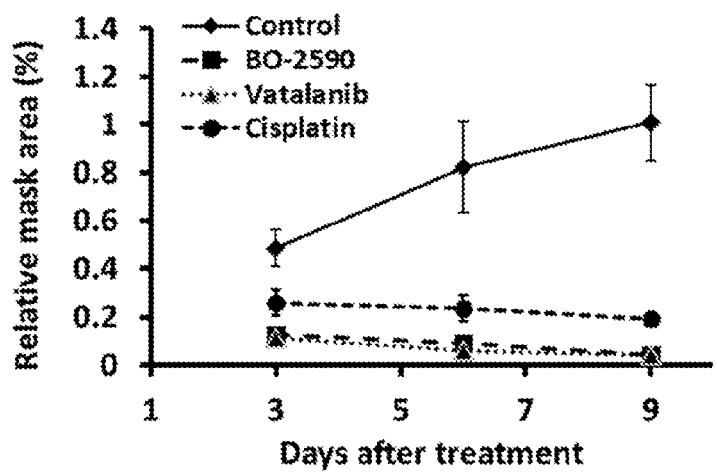

The density of blood vessels within the tumors was evaluated by immunofluorescence staining using anti-CD31 (a marker of endothelial cells) (FIG. 15, panel A). Compared to vehicle control, significantly reduced blood vessel was in general observed in tumors treated with BO-2590L, vatalanib, or cisplatin (FIG. 9, panel A). After IHC, slides were scanned by Panoramic 250 Flash II whole slide scanner. The expression of CD31 in tissue sections were determined from 15 different fields of 3 tumor sections and counts were averaged using 3DHISTECH Panoramic viewer software (3DHISTECH Ltd., Budapest, Hungary). As shown in FIG. 15(B), CD31 markers were time dependently increased in tumor without treatment. However, on day 9, CD31 marker intensity was reduced to 4% in tumors treated with BO-2590L or vatalanib compared to control (FIG. 15, panel B). Since cisplatin at the dose used significantly suppressed the tumor growth, decreased CD31 marker in cisplatin-treated tumor was also observed. On day 9, CD31 marker intensity in cisplatin-treated tumor was 19% of control, which was less extent than BO-2590L or vatalanib. These results indicated that BO-2590L was almost equally potent to vatalanib on inhibition of angiogenesis in in vivo system.

As BO-2590L is a DNA damaging agent, we thus investigated the effect of BO-2590L on the level of a DNA damage marker, γ-H2AX, via the use of immunohistochemical staining.

Figure 16:
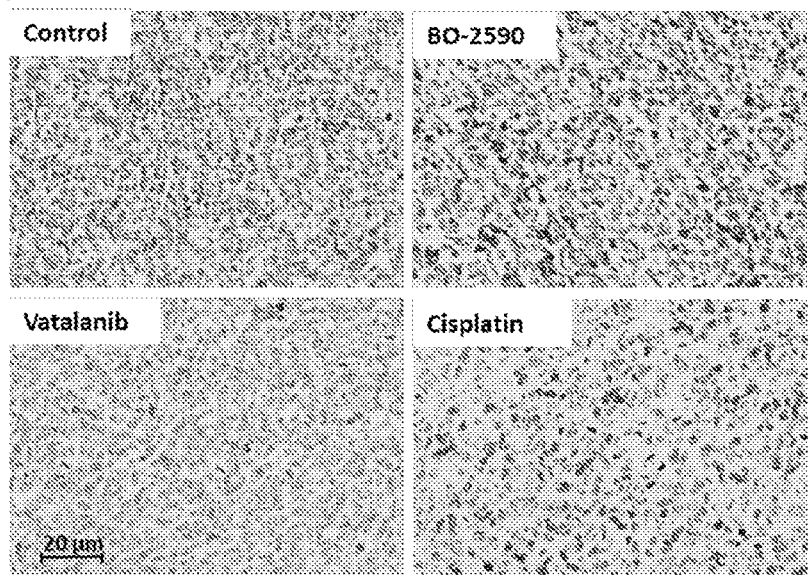
FIG. 16 illustrates effects of BO-2590L, cisplatin or vatalanib on γ-H2AX in tumors in accordance with one embodiment of the present disclosure; in which (A) Representative IHC staining using antibody against γ-H2AX at day 6 after treatment. (B) Quantitative signals of γ-H2AX in tumors. Data are represented as the mean±SEM of three mice per group.
Figure 16:
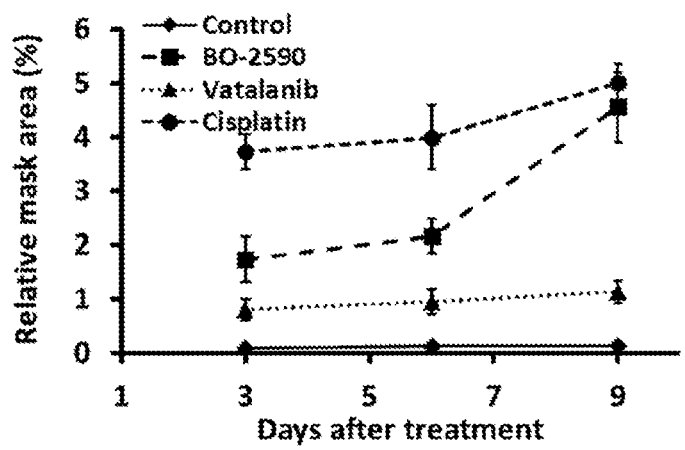

As expected, remarkably increased in γ-$H_2$AX was observed in tumors treated with cisplatin or BO-2590L, whereas much less level was observed in tumors treated with vatalanib (FIG. 16, panel A). Quantitative analysis revealed that almost no γ-$H_2$AX signals was found in control tumor. However, time-dependently increased in γ-$H_2$AX signals was found in tumor treated with cisplatin or BO-2590. In tumor treated with vatalanib, a moderate level of γ-$H_2$AX was observed (FIG. 16, panel B)

Taken together, BO-2590L may kill cancer cells via DNA damage and suppression of blood vessel.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A compound of formula (I):

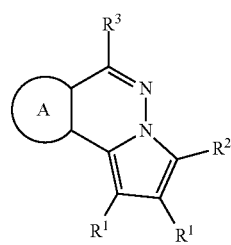

or a pharmaceutically acceptable salt or stereoisomer thereof,
wherein:

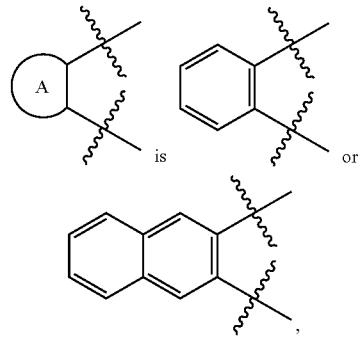

wherein A is optionally substituted with one or more substituents independently selected from the group consisting of halo, alkyl, haloalkyl, alkenyl, C(O)H, OH, O(alkyl), $O(CH_2)_xN(R_b)_2$, OC(O)alkyl, O(aryl), and aryl;

each $R^1$ is independently alkyl, wherein each alkyl is optionally and independently substituted with one or more substituents independently selected from the group consisting of halo, OR, $OC(O)CH_3$, OC(O)NHR, and $OS(O)_2R$;

$R^2$ is hydrogen, alkyl, cycloalkyl, aryl, or heteroaryl, wherein the aryl or heteroaryl is optionally substituted with one or more substituents independently selected from the group consisting of halo, CN, $C_{1-6}$ alkyl, $N(R_c)_2$, $NO_2$, O(alkyl), $-OCH_2O-$, $-O(CH_2)_2O-$, pyrrolidinyl, piperidinyl, piperazinyl, morpholino, and 4-(piperido)piperidinyl;

$R^3$ is $NR^AR^B$ or $NHPhR^c$;

each R is independently hydrogen, alkyl, cycloalkyl, or aryl;

$R^A$ is hydrogen or $C_{1-6}$ alkyl;

$R^B$ is hydrogen or $C_{1-6}$ alkyl; or $R^A$ and $R^B$, taken together with the nitrogen atom to which they are attached, form pyrrolidin-1-yl, piperidin-1-yl, piperazin-1-yl, morpholin-4-yl, 4-(piperidin-1-yl)piperidin-1-yl, or 4-(piperidin-4-yl) piperidin-1-yl, wherein the piperazin-1-yl or 4-(piperidin-4-yl)piperidin-1-yl is optionally substituted with one or more substituents independently selected from the group consisting of alkyl and $(CH_2)_nC(O)NH(CH_2)_mNR^AR^B$;

$R^c$ is hydrogen, halo, alkyl, alkenyl, alkynyl, $NHC(O)R_a$, $NHC(O)OR_a$, O(alkyl), heterocyclyl, or aryl, wherein the alkyl is optionally substituted with one or more substituents independently selected from the group consisting of halo, alkyl, haloalkyl, alkenyl, C(O)H, OC(O)alkyl, O(aryl), and aryl, and further wherein the aryl is optionally substituted with one or more substituents independently selected from the group consisting of halo, CN, $C_{1-6}$ alkyl, $N(R_c)_2$, $NO_2$, O(alkyl), $-OCH_2O-$, $-O(CH_2)_2O-$, pyrrolidinyl, piperidinyl, piperazinyl, morpholino, and 4-(piperido)piperidinyl;

$R_a$ is $C_{1-6}$ alkyl or aryl;

each $R_b$ is independently $C_{1-10}$alkyl, pyrrolidin-1-yl, piperidin-1-yl, piperazin-1-yl, morpholin-4-yl, 4-(piperidin-1-yl)piperidin-1-yl, or 4-(piperidin-4-yl)piperidin-1-yl;

each $R_c$ is independently hydrogen or $C_{1-10}$ alkyl;

m is 1, 2, 3, 4, or 5;

n is 1, 2, 3, 4, or 5; and x is 1, 2, 3, 4, or 5.

2. The compound of claim 1, or a pharmaceutically acceptable salt or stereoisomer thereof, wherein $R^3$ is $NH_2$, $NHCH_3$, or $N(CH_3)_2$.

3. The compound of claim 1, or a pharmaceutically acceptable salt or stereoisomer thereof, wherein:

$R^3$ is $NR^AR^B$; and $R^A$ and $R^B$, taken together with the nitrogen atom to which they are attached, form pyrrolidin-1-yl, piperidin-1-yl, piperazin-1-yl, morpholin-4-yl, 4-(piperidin-1-yl)piperidin-1-yl, or 4-(piperidin-4-yl) piperidin-1-yl.

4. The compound of claim 1, wherein the compound has formula (I-A):

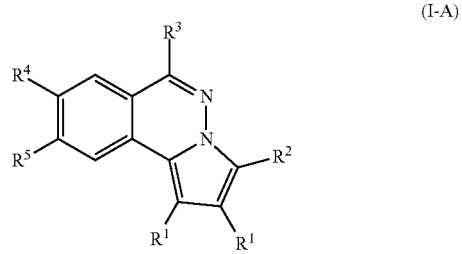

or a pharmaceutically acceptable salt or stereoisomer thereof, wherein:

$R^4$ is hydrogen, OH, O(alkyl), or $O(CH_2)_xN(R_b)_2$; and $R^5$ is hydrogen, OH, O(alkyl), or $O(CH_2)_xN(R_b)_2$.

5. The compound of claim 4, or a pharmaceutically acceptable salt or stereoisomer thereof, wherein:

each $R^1$ is independently $CH_2OH$;

$R^2$ is $CH_2CH_3$;

$R^3$ is $NR^AR^B$;

$R^A$ and $R^B$, taken together with the nitrogen atom to which they are attached, form morpholin-4-yl;

$R^4$ is hydrogen; and $R^5$ is hydrogen.

6. The compound of claim 4, or a pharmaceutically acceptable salt or stereoisomer thereof, wherein:
each $R^1$ is independently $CH_2OH$;
$R^2$ is $CH_3$;
$R^3$ is $NR^AR^B$;
$R^A$ and $R^B$, taken together with the nitrogen atom to which they are attached, form pyrrolidin-1-yl;
$R^4$ is hydrogen; and
$R^5$ is hydrogen.

7. The compound of claim 4, or a pharmaceutically acceptable salt or stereoisomer thereof, wherein:
each $R^1$ is independently $CH_2OH$;
$R^2$ is $CH_3$;
$R^3$ is $NR^AR^B$;
$R^A$ and $R^B$, taken together with the nitrogen atom to which they are attached, form 4-(piperidin-1-yl) piperidin-1-yl;
$R^4$ is hydrogen; and
$R^5$ is hydrogen.

8. The compound of claim 4, or a pharmaceutically acceptable salt or stereoisomer thereof, wherein:
each $R^1$ is independently $CH_2OC(O)NHCH_2CH_3$;
$R^2$ is $CH_3$;
$R^3$ is $NR^AR^B$;
$R^A$ and $R^B$, taken together with the nitrogen atom to which they are attached, form pyrrolidin-1-yl;
$R^4$ is hydrogen; and
$R^5$ is hydrogen.

9. The compound of claim 1, wherein the compound has formula (I-B):

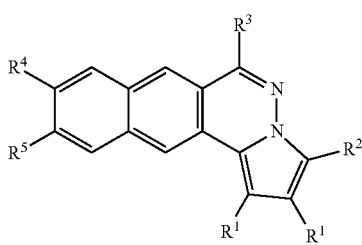

(I-B)

or a pharmaceutically acceptable salt or stereoisomer thereof, wherein:
$R^4$ is hydrogen, OH, O(alkyl), or $O(CH_2)_xN(R_b)_2$; and
$R^5$ is hydrogen, OH, O(alkyl), or $O(CH_2)_xN(R_b)_2$.

10. The compound of claim 9, or a pharmaceutically acceptable salt or stereoisomer thereof, wherein:
each $R^1$ is independently $CH_2OH$;
$R^2$ is $CH_3$;
$R^3$ is $N(CH_3)_2$;
$R^4$ is hydrogen; and
$R^5$ is hydrogen.

11. The compound of claim 9, or a pharmaceutically acceptable salt or stereoisomer thereof, wherein:
each $R^1$ is independently $CH_2OC(O)NHCH_2CH_3$;
$R^2$ is $CH_3$;
$R^3$ is $N(CH_3)_2$;
$R^4$ is hydrogen; and
$R^5$ is hydrogen.

12. The compound of claim 9, or a pharmaceutically acceptable salt or stereoisomer thereof, wherein:
each $R^1$ is independently $CH_2OC(O)NHCH_2CH_3$;
$R^2$ is $CH_3$;
$R^3$ is $NR^AR^B$;
$R^A$ and $R^B$, taken together with the nitrogen atom to which they are attached, form pyrrolidin-1-yl;
$R^4$ is hydrogen; and
$R^5$ is hydrogen.

13. A method for treating a cancer in a subject, comprising administering to the subject a therapeutically effective amount of the compound of claim 1, or a pharmaceutically acceptable salt or stereoisomer thereof.

14. The method of claim 13, wherein the cancer is selected from the group consisting of acute lymphoblastic leukemia, acute myelogenous leukemia, a bone tumor, brain cancer, breast cancer, a central nervous system neoplasm, cervical cancer, chronic myelogenous leukemia, colon cancer, esophageal cancer, Ewing's sarcoma, head and neck cancer, Hodgkin's disease, larynx cancer, melanoma, multiple myeloma, nasopharynx cancer, neuroblastoma, non-Hodgkin's lymphoma, a non-melanoma skin cancer, non-small-cell lung cancer, pancreatic cancer, prostate cancer, rectal cancer, retinoblastoma, small-cell lung cancer, testicular cancer, thyroid cancer, and Wilms' tumor.

15. The method of claim 13, wherein the compound has formula (I-A):

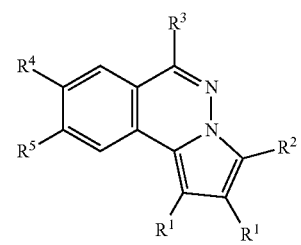

(I-A)

or a pharmaceutically acceptable salt or stereoisomer thereof,
wherein:
$R^4$ is hydrogen, OH, O(alkyl), or $O(CH_2)_xN(R_b)_2$; and
$R^5$ is hydrogen, OH, O(alkyl), or $O(CH_2)_xN(R_b)_2$.

16. The method of claim 5, wherein:
each $R^1$ is independently $CH_2OH$;
$R^2$ is $CH_2CH_3$;
$R^3$ is $NR^AR^B$;
$R^A$ and $R^B$, taken together with the nitrogen atom to which they are attached, form morpholin-4-yl;
$R^4$ is hydrogen; and
$R^5$ is hydrogen.

17. The method of claim 15, wherein:
each $R^1$ is independently $CH_2OH$;
$R^2$ is $CH_3$;
$R^3$ is $NR^AR^B$;
$R^A$ and $R^B$, taken together with the nitrogen atom to which they are attached, form pyrrolidin-1-yl;
$R^4$ is hydrogen; and
$R^5$ is hydrogen.

18. The method of claim 15, wherein:
each $R^1$ is independently $CH_2OH$;
$R^2$ is $C_3$;
$R^3$ is $NR^AR^B$;
$R^A$ and $R^B$, taken together with the nitrogen atom to which they are attached, form 4-(piperidin-1-yl) piperidin-1-yl;
$R^4$ is hydrogen; and
$R^5$ is hydrogen.

19. The method of claim 15, wherein:
each $R^1$ is independently $CH_2OC(O)NHCH_2CH_3$;
$R^2$ is $CH_3$;
$R^3$ is $NR^AR^B$;
$R^A$ and $R^B$, taken together with the nitrogen atom to which they are attached, form pyrrolidin-1-yl;
$R^4$ is hydrogen; and
$R^5$ is hydrogen.

20. The method of claim 13, wherein the compound has formula (I-B):

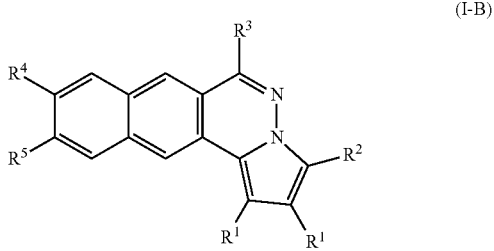

(I-B)

or a pharmaceutically acceptable salt or stereoisomer thereof,
wherein:
$R^4$ is hydrogen, OH, O(alkyl), or $O(CH_2)_xN(R_b)_2$; and
$R^5$ is hydrogen, OH, O(alkyl), or $O(CH_2)_xN(R_b)_2$.

21. The method of claim 20, wherein:
each $R^1$ is independently $CH_2OH$;
$R^2$ is $CH_3$;
$R^3$ is $N(CH_3)_2$;
$R^4$ is hydrogen; and
$R^5$ is hydrogen.

22. The method of claim 20, wherein:
each $R^1$ is independently $CH_2OC(O)NHCH_2CH_3$;
$R^2$ is $CH_3$;
$R^3$ is $N(CH_3)_2$;
$R^4$ is hydrogen; and
$R^5$ is hydrogen.

23. The method of claim 20, wherein:
each $R^1$ is independently $CH_2OC(O)NHCH_2CH_3$;
$R^2$ is $CH_3$;
$R^3$ is $NR^AR^B$;
$R^A$ and $R^B$, taken together with the nitrogen atom to which they are attached, form pyrrolidin-1-yl;
$R^4$ is hydrogen; and
$R^5$ is hydrogen.

24. The method of claim 13, wherein the method further comprises administering to the subject a chemotherapeutic agent before, together with, or after the administration of the compound of claim 1, or a pharmaceutically acceptable salt or stereoisomer thereof.

25. The method of claim 24, wherein the chemotherapeutic agent is selected from the group consisting of apomine, arsenic trioxide, betulinic acid, bortezomib, bosentan, capecitabine, carboplatin, carmustine, celecoxib, cisplatin, 4-S-cysteaminyl catechol, 4-S-cysteaminyl phenol, dacarbazine, docetaxel, doxorubicin, everolimus, imatinib mesylate, ipilimumab, lambrolizuma, lenalidomide, oxaliplatin, paclitaxel, sorafenib, tamoxifen, temozolomide, thalidomide, tremelimumab, valproic acid, vemurafenib (PLX4032), vinblastine, an anti-cytotoxic T-lymphocyte associated protein 4 drug, an anti-programmed death receptor-1 drug, a mammalian target of rapamycin inhibitor, a MEK inhibitor, a phosphoinositide 3-kinase inhibitor, and a poly (ADP-ribose) polymerase inhibitor.

* * * * *